(12) United States Patent
Cooper et al.

(10) Patent No.: US 10,947,271 B2
(45) Date of Patent: Mar. 16, 2021

(54) ANTIBACTERIAL AGENTS

(71) Applicant: THE UNIVERSITY OF QUEENSLAND, St Lucia (AU)

(72) Inventors: Matthew Cooper, Brisbane (AU); Mark Blaskovich, Brisbane (AU)

(73) Assignee: THE UNIVERSITY OF QUEENSLAND, St Lucia (AU)

( * ) Notice: Subject to any disclaimer, the term of this patent is extended or adjusted under 35 U.S.C. 154(b) by 182 days.

(21) Appl. No.: 15/117,704

(22) PCT Filed: Feb. 10, 2015

(86) PCT No.: PCT/AU2015/000071
§ 371 (c)(1),
(2) Date: Aug. 9, 2016

(87) PCT Pub. No.: WO2015/117196
PCT Pub. Date: Aug. 13, 2015

(65) Prior Publication Data
US 2017/0204138 A1 Jul. 20, 2017

(30) Foreign Application Priority Data
Feb. 10, 2014 (GB) .................................. 1402267

(51) Int. Cl.
| C07K 5/11 | (2006.01) |
| C07K 7/06 | (2006.01) |
| C07K 5/09 | (2006.01) |
| C07K 5/068 | (2006.01) |
| C07K 9/00 | (2006.01) |
| A61K 38/00 | (2006.01) |

(52) U.S. Cl.
CPC ........ *C07K 5/1019* (2013.01); *C07K 5/06086* (2013.01); *C07K 5/0815* (2013.01); *C07K 7/06* (2013.01); *C07K 9/008* (2013.01); *A61K 38/00* (2013.01)

(58) Field of Classification Search
CPC ............................. C07K 5/1019; A61K 38/00
See application file for complete search history.

(56) References Cited

U.S. PATENT DOCUMENTS

| 6,017,511 A | 1/2000 | Wong et al. |
| 7,078,380 B2 * | 7/2006 | Cooper ................ C07K 14/195 514/2.4 |

FOREIGN PATENT DOCUMENTS

| JP | 2001163898 | 6/2001 |
| WO | WO 199630401 | 10/1996 |
| WO | WO 199802454 | 1/1998 |
| WO | 1998010651 | 3/1998 |
| WO | 1999042136 | 8/1999 |
| WO | WO 200183520 | 11/2001 |
| WO | WO 2002005837 | 1/2002 |
| WO | WO-0236612 A1 * | 5/2002 ............. C07K 9/008 |
| WO | WO 2002036612 | 5/2002 |
| WO | WO 2004022101 | 3/2004 |
| WO | WO 2004044222 | 5/2004 |
| WO | WO 2007047608 | 4/2007 |
| WO | 2007103548 | 6/2007 |
| WO | 2010046900 | 4/2010 |
| WO | WO 2011019839 | 2/2011 |

OTHER PUBLICATIONS

Infante, et al (Lipopeptidic Surfactants. II. Acidic and Basic Nα-Lauroyl-L-Arginine Dipeptides from Pure Amino Acids, JAOCS 1992, 69(7):647-652) (Year: 1992).*
Zeppieri, et al (Interfacial Tension of Alkane + Water Systems, J. Chem. Eng. Data 2001, 46:1086-1088) (Year: 2001).*
Van 't Veen, et al (Exogenous pulmonary surfactant as a drug delivering agent: influence of antibiotics on surfactant activity, British Journal of Pharmacology 1996, 118:593-598). (Year: 1996).*
Cruciani (Introduction, Penetration of vancomycin into human lung tissue, Journal of Antimicrobial Chemotherapy 1996, 38:865-869 ) (Year: 1996).*
Infante et al. ("Lipopeptidic Surfactants. II. Acidic and Basic N-Lauronyl-L-Arginine Dipeptides from Pure Amino Acids", JAOCS, 1992, pp. 647-652 (Year: 1992).*
Albada et al. "Potential scorpionate antibiotics: Targeted hydrolysis of lipid II containing model membranes by vancomycin—TACzyme conjugates and modulation of their antibacterial activity by Zn-ions" Bioorganic & Med Chem Letters (2009) 19:3721-3724 (with 14 additional pages of supporting information).
Allen et al. "Inhibition of Peptidoglycan Biosynthesis in Vancomycin-Susceptible and -Resistant Bacteria by a Semisynthetic Glycopeptide Antibiotic" Antimicrobial agents and chemotherapy (1996) 40(10):2356-2362.
Blais et al. "Antistaphylococcal Activity of TD-1792, a Multivalent Glycopeptide-Cephalosporin Antibiotic" Antimicrob. Agents Chemother. (2012) 56(3):1584-1587.
Chang et al. "Design, Synthesis, and Antibacterial Activity of Demethylvancomycin Analogues against Drug-Resistant Bacteria" Chem Med Chem (2013) 8:976-984.
Cooper et al. "Reductive Alkylation of Glycopeptide Antibiotics: Synthesis and Antibacterial Activity" J Antibiot (1996) 49(6):575-581.
Crane et al. "Synthesis and Evaluation of Vancomycin Aglycon Analogues That Bear Modifications in the N-Terminal D-Leucyl Amino Acid" J Med Chem (2009) 52:1471-1476.
Crane et al. "Synthesis and Evaluation of Selected Key Methyl Ether Derivatives of Vancomycin Aglycon" J Med Chem (2010) 53:7229-7235.

(Continued)

*Primary Examiner* — Lianko G Garyu
(74) *Attorney, Agent, or Firm* — Carol L. Francis; Rudy J. Ng; Bozicevic, Field & Francis LLP

(57) ABSTRACT

The invention concerns agents with antibacterial activity, their production and use in the treatment of bacterial infections in animals, including man. The agents are derivatives of vancomycin-type antibiotics, of structure X—W-L-V, wherein X is hydrogen, acetyl or a lipophilic membrane-insertive element, W is a basic peptide or basic amino acid; L is a linking group and V is a glycopeptide moiety which inhibits peptidoglycan biosynthesis in bacteria.

23 Claims, 5 Drawing Sheets

Specification includes a Sequence Listing.

(56) References Cited

OTHER PUBLICATIONS

Dong et al. "Strategies for targeting complement inhibitors in ischaemia/reperfusion injury" Mol. Immunol. (1999) 36:957-963.
Ge et al. "Vancomycin Derivatives That Inhibit Peptidoglycan Biosynthesis Without Binding D-Ala-D-Ala" Science (1999) 284:507-511.
Jarrad et al. "Supercharged vancomycin analogues beat the superbug *Clostridium difficile*" Institute for Molecular Bioscience (2013) 1 page.
Malabarba et al. "Structural Modifications of Glycopeptide Antibiotics" Medicinal Research Reviews (1997) 17:69-137.
Nakama et al. "Discovery of a Novel Series of Semisynthetic Vancomycin Derivatives Effective against Vancomycin-Resistant Bacteria" J Med Chem (2010) 53:2528-2533.
Nicas et al. "Semisynthetic Glycopeptide Antibiotics Derived from LY264826 Active against Vancomycin-Resistant Enterococci" Antimicrob Agents Chemother. (1996) 40(9):2194-2199.
Pinchman et al. "Probing the Role of the Vancomycin E-Ring Aryl Chloride: Selective Divergent Synthesis and Evaluation of Alternatively Substituted E-Ring Analogues" J Med Chem (2013) 56:4116-4124.
Printsevskaya et al. Synthesis and study of antibacterial activities of antibacterial glycopeptide antibiotics conjugated with benzoxaboroles Future Med Chem (2013) 5(6):641-652.
Rodriguez et al. "Novel Glycopeptide Antibiotics: N-Alkylated Derivatives Active Against Vancomycin-Resistant Enterococci" J. Antibiot (1998) 51(6):560-569.
Sundram & Griffin "General and Efficient Method for the Solution- and Solid-Phase Synthesis of Vancomycin Carboxamide Derivatives" J Org Chem (1995) 60:1102-1103.
Xie et al. "Total Synthesis of [Ψ[C(=S)NH]Tpg4]Vancomycin Aglycon, [Ψ[C(=NH)NH]Tpg4]Vancomycin Aglycon, and Related Key Compounds: Reengineering Vancomycin for Dual D-Ala-D-Ala and D-Ala-D-Lac Binding" J Am Chem Soc (2012) 134:1284-1297.
Xie et al. A Redesigned Vancomycin Engineered for Dual D-Ala-D-Ala and D-Ala-D-Lac Binding Exhibits Potent Antimicrobial Activity Against Vancomycin-Resistant Bacteria: J Am Chem Soc (2011) 133:13946-13949.
Yarlagadda et al. "Membrane Active Vancomycin Analogues: A Strategy to Combat Bacterial Resistance" J Med Chem (2014) 57:4558-4568.
Yasukata et al. "An Efficient and Practical Method for Solid-Phase Synthesis of Tripeptide-Bearing Glycopeptide Antibiotics: Combinatorial Parallel Synthesis of Carboxamide Derivatives of Chloroorienticin B" Bioorganic & Med Chem Letters 12 (2002) 3033-3036.
Zhanel et al. "New Lipoglycopeptides: A Comparative Review of Dalbavancin, Oritavancin and Televancin" Drugs (2010) 70(7):859-886.
Zhang et al. "Synthesis and antibacterial activity against Clostridium difficile of novel demethylvancomycin derivatives" Bioorg Med Chem Lett (2012) 22:4942-4945.
Blaskovich et al., (2018) "Protein-inspired antibiotics active against vancomycin- and daptomycin-resistant bacteria," Nature Communications 9(22): 1-17.
Kharasch et al., (1991) "Pulmonary Surfactant as a Vehicle for Intratracheal Delivery of Technetium Sulfur Colloid and Pentamidine in Hamster Lungs," Am Rev Respir Dis 144: 909-913.
Lachmann and Gommers (1993) "Is it rational to treat pneumonia with exogenous surfactant?" Eur Respir J., 6: 1427-1428.

\* cited by examiner

Figure 1: Comparison of Stability of S-S linked (MCC535) and C-linked (MCC223) Analogues in the presence of glutathione
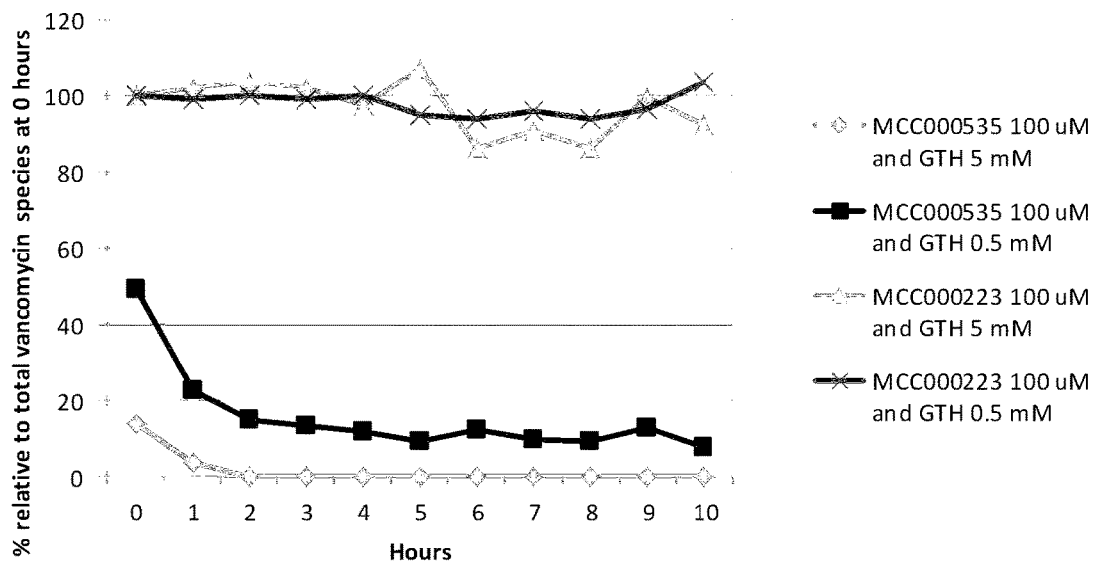

Figure 2: Pharmacokinetic Profiles of MCC080, MCC174, MCC229, MCC310, MCC455, MCC520, MCC939 MCC4815, MCC4829, MCC4966, MCC5145, MCC5226 and MCC5362
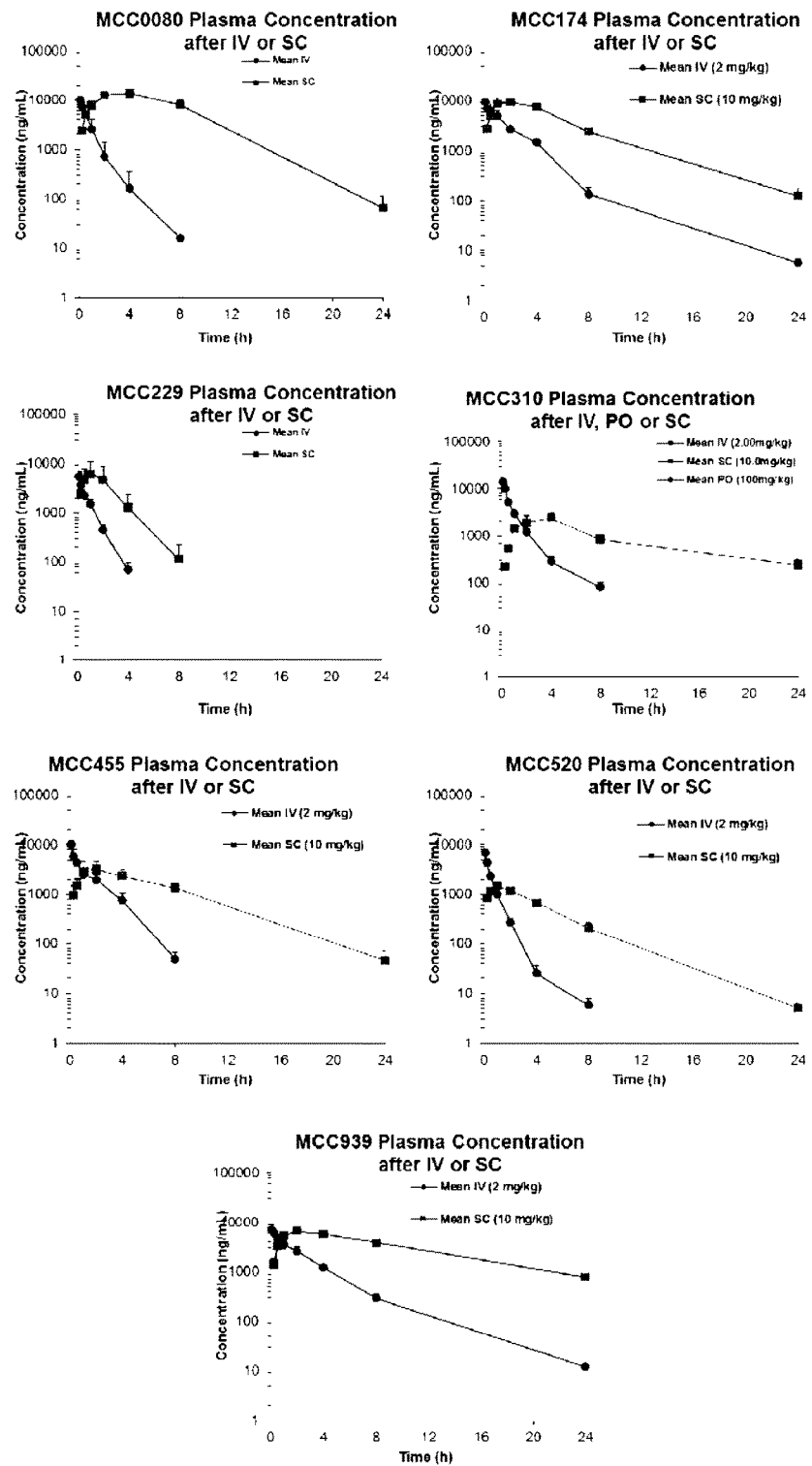

Figure 3: Efficacy of MCC080, MCC 174, MCC 310, MCC 344, MCC 455 and MCC742 against MRSA in Mouse Thigh Infection Model.
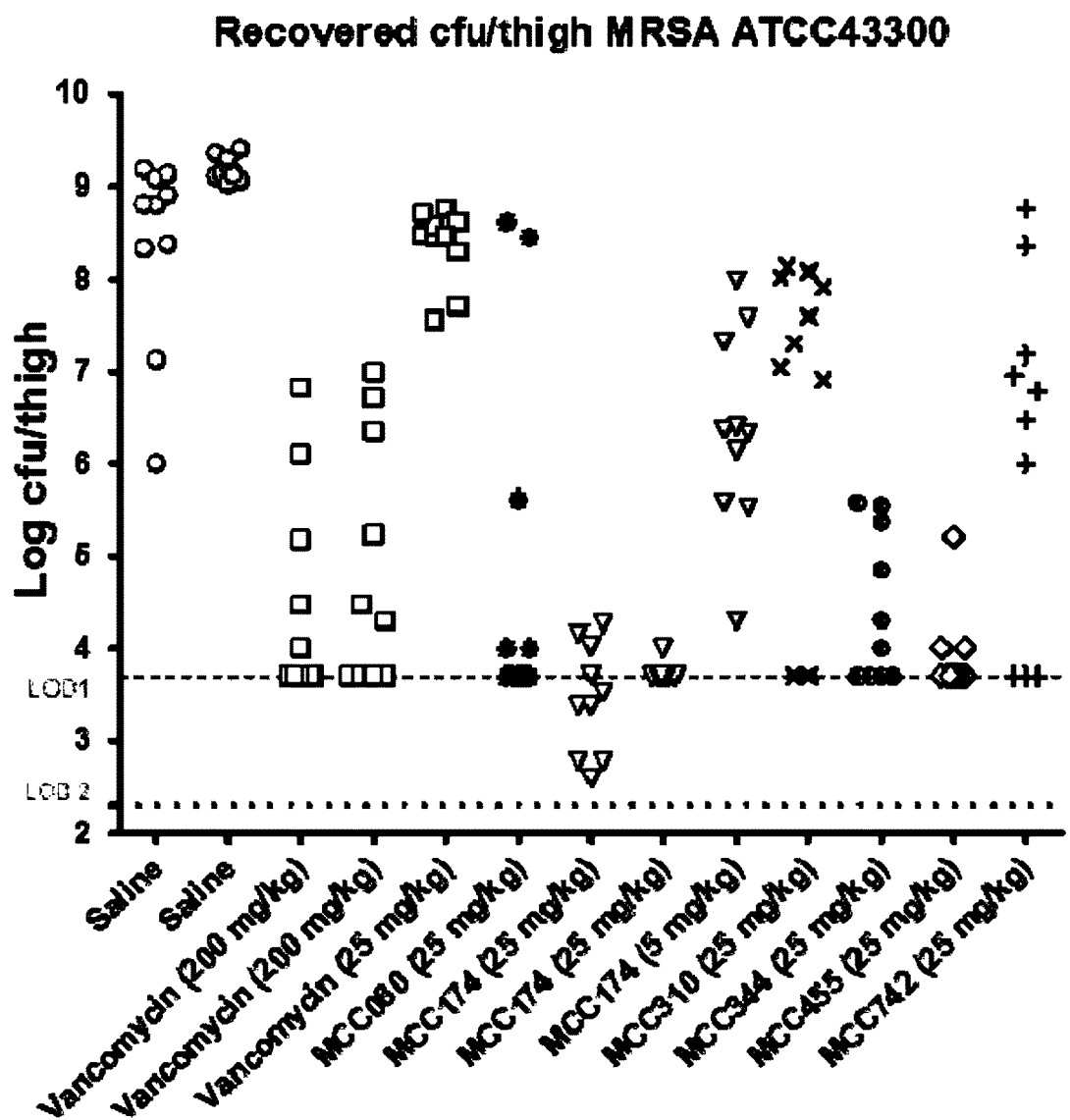

Figure 4: Efficacy of MCC 174, MCC 310, MCC 455 and MCC939 against S. pneumoniae in Mouse Lung Infection Survival Model.
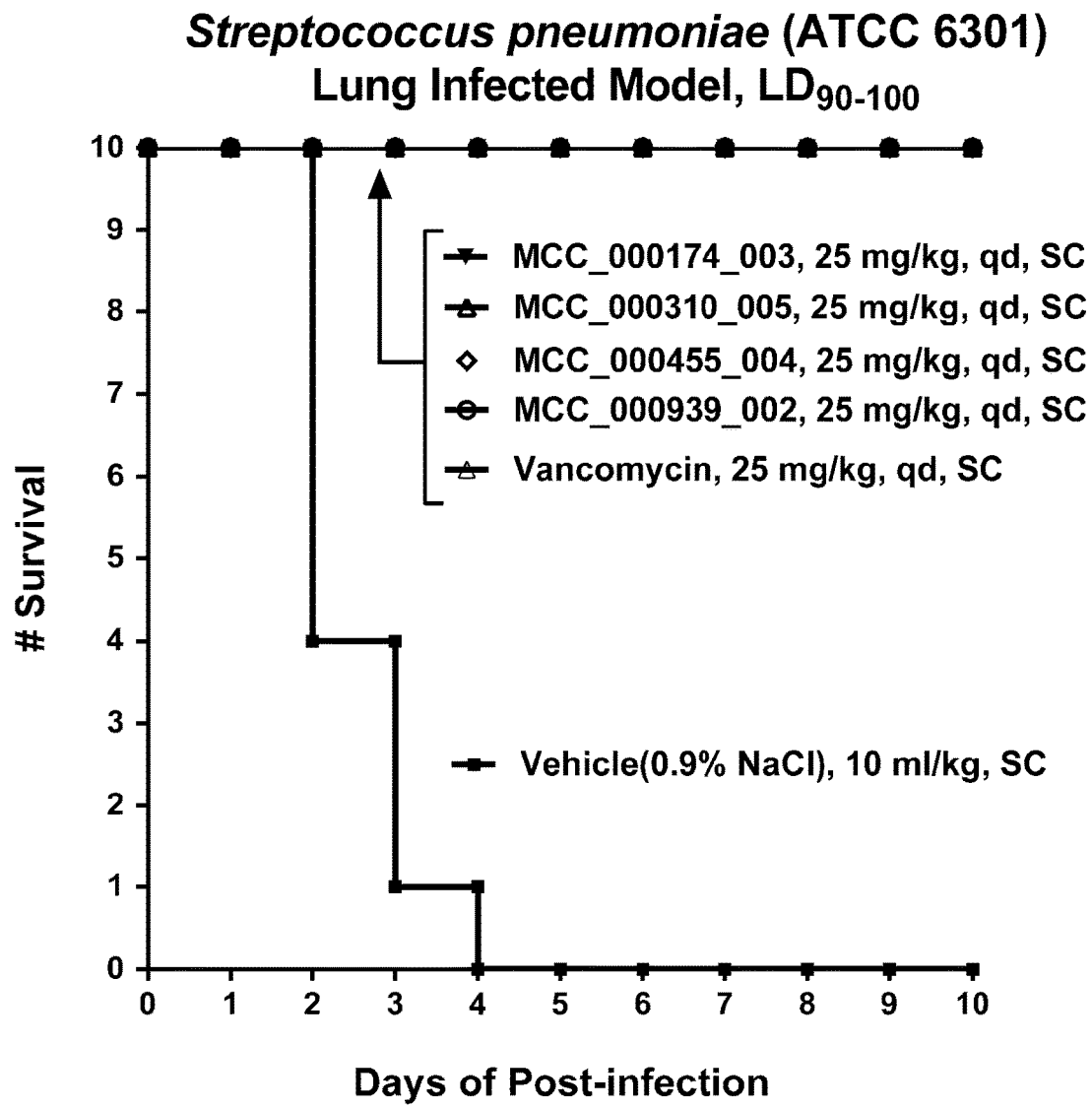

ANTIBACTERIAL AGENTS

The present invention concerns agents with anti-bacterial activity and improved physiological stability and methods and intermediates for their production. The present invention further concerns the use of such agents for the treatment of bacterial infections in animals, including man.

BACKGROUND TO THE INVENTION

Diseases caused by bacterial infections have significant morbidity and mortality in man and other mammals. Gram positive bacteria have a typical lipid bilayer cytoplasmic membrane surrounded by a rigid cell wall. The cell wall is composed mainly of peptidoglycan, a polymer of N-acetyl-glucosamine and N-acetyl muramic acid cross-linked by a peptide comprising alternating D- and L- amino acids.

The glycopeptide group of antibiotics, most commonly represented by vancomycin inhibit the synthesis of the cell wall in sensitive bacteria by blocking the cross-linking of the sugar and peptidic components of peptidoglycans during the synthesis of the bacterial cell wall. Without sufficient cross-linking, the cell wall becomes mechanically fragile and the bacteria lyse when subjected to changes in osmotic pressure. Vancomycin binds with high affinity to the D-alanyl-D-alanine (D-Ala-D-Ala) terminus of the pentapeptide portion of the peptidoglycan precursor before cross-linking. The D-Ala-D-Ala dipeptide forms complementary hydrogen bonds with the peptide backbone of vancomycin. It is thought that the vancomycin-peptidoglycan complex physically blocks the action of the transpeptidase enzyme and thereby inhibits the formation of the peptide cross-bridges that strengthens the peptidoglycan. This activity also leads to the accumulation of peptidoglycan precursors in the bacterial cytoplasm.

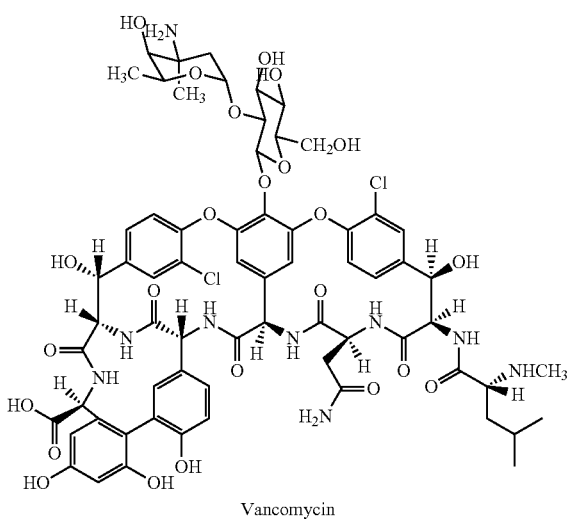

Vancomycin

Resistance to antibiotics is well documented and the resistant strains are a potential major threat to the well-being of mankind. Several types of resistance have been described for vancomycin, due to modifications to the Lipid Ii peptide structure, or alterations to the bacterial cell wall composition.

Approaches that have been used to combat the emergence of antibiotic resistant strains include the modification of existing antibiotics to improve their potency against resistant organisms, or the discovery of new peptide antibiotics which kill their targets by permeabilizing the bacterial plasma membrane. Examples of the first approach have recently focussed on creating derivatives of glycopeptides such as vancomycin.

Functionalisation of the carboxyl terminal of vancomycin using the coupling agent 2-(1-hydroxybenzotriazol-1-yl)-1,1,3,3-tetramethyl-uronium hexafluorophosphate (HBTU) has been successful in attaching short peptide sequences, both in solution and solid phases (Sundram, U. N. and Griffin, J. H. (1995) General and Efficient Method for the Solution- and Solid-Phase Synthesis of Vancomycin Carboxamide Derivatives J. Org. Chem. 60 1102-1103). The aminosugar and terminal amine moieties of vancomycin and related antibiotics have also been derivatised. In a reductive alkylation approach, a series of compounds alkylated on the vancosamine sugar was created, some of which showed greatly improved activity vs vancomycin resistant bacterial strains (Cooper R D G, Snyder N J, Zweifel M J, Staszak M A, Wilkie S C, Nicas T I, Mullen D L, Butler T F, Rodriguez M J, Huff B E, Thompson R C. Reductive alkylation of glycopeptide antibiotics: synthesis and antibacterial activity. J Antibiot 49 (1996): 575-581; and Rodriguez, M. J., N. J. Snyder, M. J. Zweifel, S. C. Wilkie, D. R. Stack, R. D. Cooper, T. I. Nicas, D. L. Mullen, T. F. Butler, and R. C. Thompson. 1998. Novel glycopeptide antibiotics: N-alkylated derivatives active against vancomycin-resistant enterococci J. Antibiot. (Tokyo), 51, 560-569).

One modified glycopeptide derivative, telavancin, was approved for clinical use in 2009, while two other derivatives, dalbavancin and oritavancin, have been tested in large clinical trials (Zhanel G G, Calic D, Schweizer F, Zelenitsky S, Adam H, Lagacé-Wiens P R, Rubinstein E, Gin A S, Hoban D J, Karlowsky J A. New lipoglycopeptides: a comparative review of dalbavancin, oritavancin and telavancin. Drugs. 2010 70:859-886). Another modified glycopeptide, TD-1792, links a glycopeptide antibiotic to a cephalosporin (Blais, J; Stacey R. Lewis, Kevin M. Krause and Bret M. Benton Antistaphylococcal Activity of TD-1792, a Multivalent Glycopeptide-Cephalosporin Antibiotic Antimicrob. Agents Chemother. 2012 56 1584-1587).

WO-A-98/02454 describes polypeptide derivatives in which a soluble therapeutic polypeptide is modified with an entity of general structure:

-(L-[W])$_n$BX    (I)

in which each L is independently a flexible linker group, each W is independently a peptidic membrane-binding element, n is an integer greater than or equal to one, and X is a peptidic or non-peptidic membrane-binding or insertive element.

Structures of type (I) represent a combinatorial array of membrane-interactive elements whose attachment to soluble polypeptides was found to mediate binding of those polypeptides to the outer cell membrane of mammalian cells. This gave rise to therapeutic benefits, particularly in the case of regulators of complement activation acting as cytoprotectants and anti-inflammatory agents (e.g. J. Dong, J R Pratt, R A Smith, I. Dodd and SH Sacks, Strategies for targeting complement inhibitors in ischaemia/reperfusion injury. Mol. Immunol. 36 (1999), pp. 957-963).

WO 02/36612 describes general structures:

V-L-W—X (II)

wherein
V is a glycopeptide moiety which inhibits peptidoglycan biosynthesis in bacteria;
L is a linking group;
W is a peptidic membrane-associating element; and
X is hydrogen or a membrane-insertive element.

In WO 02/36612 whereas the broad definition of the linking group L includes "-alkylene of $C_1$-$C_3$, —O-alkylene of C1-C6, -alkylene of $C_1$-$C_6$—O—, —O—, —N(H or lower alkyl of $C_1$-$C_3$)—, —S—, —SO—, —$SO_2$, —XH—C(O)—, —C(O)—NH—, —CH=CH—, —C≡C—, —N=N—, —O—C(O)— and —C(O)—O—", exemplification in structures 1 to 16 on page 50-51 thereof is only of compounds in which the linking group L contains a disulphide bond.

Furthermore, in WO 02/36612, whereas the broad definition of W is as a "peptidic membrane-associating element", later defined either as a membrane-binding peptide comprising from 2 to 10 contiguous residues selected from lysine or arginine, the membrane-binding peptide itself comprising from 7 to 30 amino acids, or a membrane-inserting peptide, exemplification of the membrane-binding peptide in structures 1 to 16 on page 50-51 thereof is limited to SEQ ID NO:4 to SEQ ID NO:8, which contain 14, 16 or 20 amino acids, each of which comprising 6 contiguous lysine and/or arginine residues.

WO 04/022101 describes a modified therapeutic agent comprising three or more membrane binding elements, of which at least two are lipophilic elements and the third is generally an amino acid sequence comprising basic amino acids, covalently associated with a soluble agent, e.g. protein, an anti-cancer agent or an antibacterial agent. The anti-bacterial agent may be vancomycin, and when this is the case, the amino acid sequence(s) typically contain(s) from 6 to 20 amino acids and is/are linked to the N or C terminus of the vancomycin by linker groups resulting that contain a disulphide bond.

Compounds based on these general structures demonstrated improved antibacterial activity against a range of organisms.

Given the ability of Gram positive bacteria to develop resistance to glycopeptide antibiotics, there remains a need for new anti-bacterial agents with good physiological stability and methods for controlling bacterial infections.

SUMMARY OF THE INVENTION

The present inventors have discovered that structures of the prior art containing a link between the glycopeptide and membrane-binding element, in e.g. structure II above, that includes a disulphide bond can undergo disulphide exchange with other thiols under physiological conditions, leading to degradation of the compounds and a resulting loss of activity. Furthermore, the long peptide sequences described in the prior art are both difficult to synthesise on the scale required for a commercial antibiotic and are subject to proteolysis under physiological conditions.

Accordingly, the present inventors have focussed on the production of novel glycopeptide derivatives having a similar structure to those of formula II, above, but in which the linking group L is specifically selected to provide compounds which display better stability under physiological conditions while retaining antimicrobial activity. Further selection within the group W provides advantages in terms of the ease of synthesis of the compounds as well as a reduced potential for proteolysis.

Accordingly, in a first aspect the present invention provides compounds of formula (III):

X—W-L-V (III)

wherein:
X is a lipophilic group attached to the N-terminus of W, is based on carbon atoms and has the following parameters;
  having from 3 to 60 carbon atoms including those of any aromatic rings, if present;
  being straight or branched, and in the case of the latter containing one to six branch points;
  being saturated or unsaturated, in the case of the latter containing one to eight double or triple bonds;
  optionally having up to 6 heteroatoms (in addition to those, if present, in aromatic rings, if present), independently selected from S, O or N, not contained in an acidic substituent;
  optionally containing one or more, for example two, three, four, five or six, aromatic rings, which may be fused and each of which may contain 1, 2 or 3 heteroatoms which, if present, are independently selected from N, O or S; and
  optionally having from one to six substituents selected from hydroxy, amino, methyl, methylamino and halo;
W is a basic amino acid or a basic peptide consisting of from 2 to 10 amino acids, provided that W is not or does not contain any amino acids with a sulphur-containing side chain;
L is a linking group of the formula —NH—$(CR^1R^2)_m$—Z—$(CR^3R^4)_n$—NH— wherein:
  Z is oxygen or an optionally substituted moiety selected from the group consisting of —NH—, —CONH—, —NHCO—, —$(OCH_2CH_2)_p$—, $C_1$-$C_{12}$alkyl, $C_2$-$C_{12}$alkenyl, $C_2$-$C_{12}$alkynyl, $C_1$-$C_{12}$heteroalkyl, $C_1$-$C_{10}$heteroalkenyl, $C_3$-$C_{12}$cycloalkyl, $C_1$-$C_{12}$heterocycle, $C_6$-$C_{18}$aryl, or $C_1$-$C_{12}$heteroaryl; and
  $R^1$, $R^2$, $R^3$, and $R^4$ are each independently selected from the group consisting of H, halogen, optionally substituted $C_1$-$C_{12}$alkyl, optionally substituted $C_2$-$C_{12}$alkenyl, optionally substituted $C_2$-$C_{12}$alkynyl, optionally substituted $C_1$-$C_{12}$heteroalkyl, optionally substituted $C_1$-$C_{10}$heteroalkenyl, optionally substituted $C_3$-$C_{12}$cycloalkyl, optionally substituted $C_1$-$C_{12}$heterocycle, optionally substituted $C_6$-$C_{18}$aryl, optionally substituted $C_1$-$C_{18}$heteroaryl, optionally substituted carboxy, optionally substituted carboxamide; and
  m is an integer selected from the group consisting of 0, 1, 2, and 3; and
  n is an integer selected from the group consisting of 0, 1, 2, and 3;
  provided that both of m and n are not 0; and
  p is an integer selected from the group consisting of 1-10;
or
L is selected from one of the formulae:

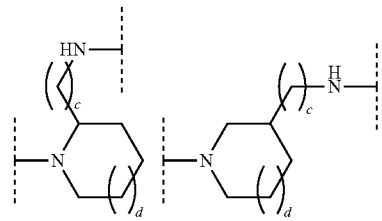

-continued

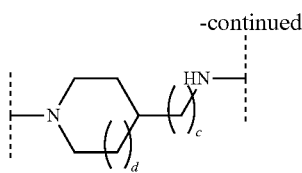

wherein c and d are integers selected from the group consisting of 0, 1, and 2; and the dotted lines show points of attachment to V and W; and V is a glycopeptide moiety which inhibits peptidoglycan biosynthesis in bacteria; or a pharmaceutically acceptable salt or prodrug thereof.

The present invention also provides a pharmaceutically acceptable salt or prodrug of a compound of formula (III) as defined above.

In a further aspect, the present invention provides a composition comprising a compound of formula (III) as defined above and a pharmaceutically acceptable carrier, diluent or excipient.

In another aspect, the present invention provides a compound of formula (III) as defined above for use in a method of treatment of the human or animal body.

In yet a further aspect, the present invention provides a method of treating a bacterial infection in a subject which method comprises administering to a subject an effective amount of a compound of formula (III) as defined above or a composition comprising said compound.

Definitions

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an anti-bacterial agent" includes a plurality of such agents and reference to "the pharmaceutical composition" includes reference to one or more pharmaceutical compositions and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

"Treating" or "treatment" of a condition or disease includes: (1) preventing at least one symptom of the conditions, i.e., causing a clinical symptom to not significantly develop in a mammal that may be exposed to or predisposed to the disease but does not yet experience or display symptoms of the disease, (2) inhibiting the disease, i.e., arresting or reducing the development of the disease or its symptoms, or (3) relieving the disease, i.e., causing regression of the disease or its clinical symptoms.

A "therapeutically effective amount" or "efficacious amount" means the amount of a compound that, when administered to a mammal or other subject for treating a disease, is sufficient, in combination with another agent, or alone in one or more doses, to effect such treatment for the disease. The "therapeutically effective amount" will vary depending on the compound, the disease and its severity and the age, weight, etc., of the subject to be treated.

The terms "subject," "individual," and "patient" are used interchangeably herein to a member or members of any mammalian or non-mammalian species that may have a need for the pharmaceutical methods, compositions and treatments described herein. Subjects and patients thus include, without limitation, primate (including humans), canine, feline, ungulate (e.g., equine, bovine, swine (e.g., pig)), avian, and other subjects. Humans and non-human mammals having commercial importance (e.g., livestock and domesticated animals) are of particular interest.

"Mammal" refers to a member or members of any mammalian species, and includes, by way of example, canines; felines; equines; bovines; ovines; rodentia, etc. and primates, particularly humans. Non-human animal models, particularly mammals, e.g. a non-human primate, a murine (e.g., a mouse, a rat), etc. may be used for experimental investigations.

A "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

"Prodrugs" means any compound that releases an active parent drug according to formula III shown herein in vivo when such prodrug is administered to a mammalian subject. Prodrugs of a compound of formula III herein are prepared by modifying functional groups present in the compound of the generic formula in such a way that the modifications may be cleaved in vivo to release the parent compound. Prodrugs include compounds of formula III shown herein wherein a hydroxy, amino, or sulfhydryl group in one or more of the generic formulas shown below is bonded to any group that may be cleaved in vivo to regenerate the free hydroxyl, amino, or sulfhydryl group, respectively. Examples of prodrugs include, but are not limited to esters (e.g., acetate, formate, and benzoate derivatives), carbamates (e.g., N,N-dimethylaminocarbonyl) of hydroxy functional groups in compounds of one or more of the generic formulas shown below, and the like.

A compound of the present invention, or a component part thereof, may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see, e.g., the discussion in Chapter 4 of "Advanced Organic Chemistry", 4th edition J. March, John Wiley and Sons, New York, 1992).

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DESCRIPTION OF THE FIGURES

FIG. 1: MCC223 and MCC535 Stability in the Presence of Glutathione: this figure illustrates a comparison of the stability of a compound of the prior art, MCC535 (in which V is vancomycin, X is $nC_{13}CO$, W is —KKK— and L is (S)—NHCH($CO_2H$) $CH_2$—SS—$(CH_2)_2$—NH—) with compound MCC223, as described in the following.

FIG. 3: Efficacy of MCC080, MCC174, MCC310, MCC344, MCC455 and MCC742 against MRSA in Mouse Thigh Infection Model. This figure demonstrates the reduction in log cfu (colony forming units) in each thigh of immunocompromised mice that have been injected in each thigh with $10^5$ cfu of MRSA (ATCC 34400).

DETAILED DESCRIPTION OF THE INVENTION

Figure 2:
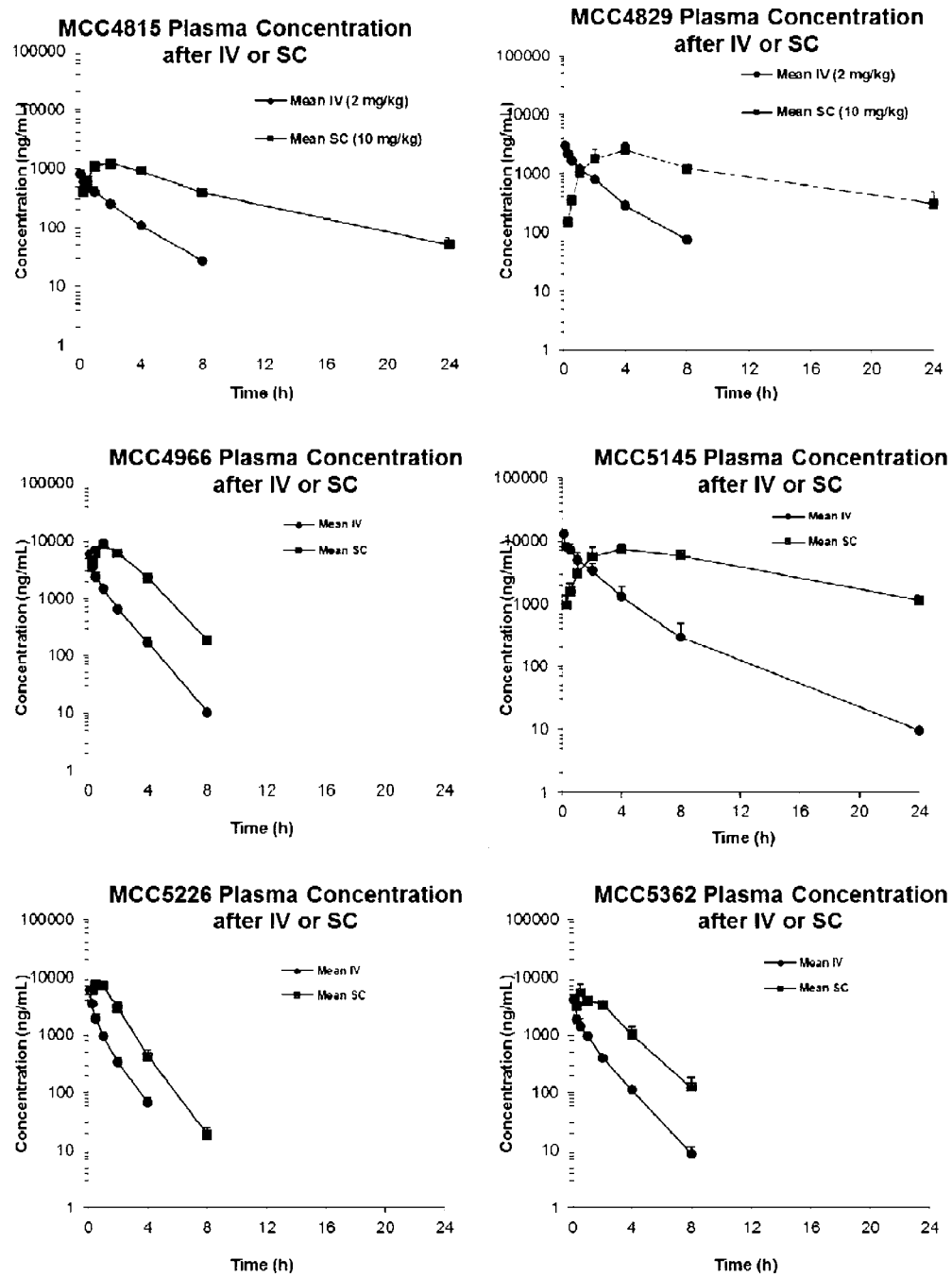
FIG. 2: Pharmacokinetic Profiles of MCC174, MCC310, MCC455, MCC520, MCC939 and MCC4815. This figure illustrates the in vivo stability of several compounds in mice, tested by both intravenous (iv) and subcutaneous (sc) administration (n=3 for each route, 2 mg/kg iv and 10 mg/kg sc).

Compounds of the present invention are glycopeptide antibiotics of formula (III). The compounds show good antibacterial activity, as is illustrated below, as well as better stability in the presence of glutathione and better stability in vivo than prior art compounds of formula (II) illustrated above.

Element X

In the compounds of the invention, X is a lipophilic group attached to the N-terminus of W, is based on carbon atoms and has the following parameters:

having from 3 to 60 atoms including those of any alicyclic or aromatic rings, if present;

being straight or branched, and in the case of the latter containing one or more, for example two, three, four, five or six branch points;

being saturated or unsaturated, in the case of the latter containing one to eight, for example 1, 2, 3, 4, 5, 6, 7 or 8 double or triple bonds;

optionally having up to 6, e.g. 1, 2, 3, 4, 5 or 6 heteroatoms (in addition to those, if present, in aromatic rings, if present), independently selected from O, S or N, not contained in an acidic substituent;

optionally containing one or more, for example two, three, four, five or six, aromatic rings, which may be fused and each of which may contain from 1, 2 or 3 heteroatoms which, if present, are independently selected from N, O or S; and optionally having from one to six, (such as 1, 2, 3, 4, 5 or 6) substituents independently selected from hydroxy, amino, methyl, methylamino and halo.

If necessary, X may include a functional group allowing for attachment to W. Appropriate functional groups are known in the art and include, for example, a carbonyl group, e.g. derived from an activated carboxylic acid, or a sulphone group derived from a sulphonyl chloride.

In a particular aspect, group X is a lipophilic group comprising, and attached to the N-terminus of W via, a carbonyl group, a $CH_2$ group or an $SO_2$ group, most preferably a carbonyl group.

In one embodiment, X is of formula (IV):

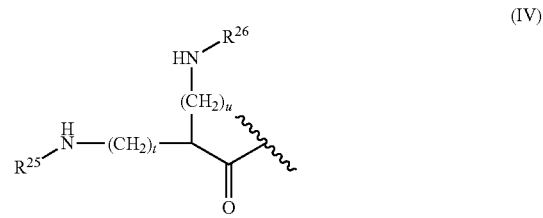

(IV)

wherein each $R^{25}$ and $R^{26}$ is a lipophilic group which has the following parameters:

having from 3 to 30 carbon atoms including those of any alicyclic or aromatic rings, if present;

being straight or branched, and in the case of the latter containing one to three branch points;

being saturated or unsaturated, in the case of the latter containing one to four double or triple bonds;

optionally having 1, 2 or 3 heteroatoms (in addition to those, if present, in aromatic rings, if present), independently selected from S, O or N;

optionally containing one or more, for example two or three, aromatic rings, which may be fused and each of which may contain 1, 2 or 3 heteroatoms which, if present, are independently selected from N, O or S; and optionally having from one to three substituents selected from hydroxy, amino, methyl, methylamino and halo;

t is an integer selected from the group consisting of 0, 1, 2, 3, 4, and 5; and u is an integer selected from the group consisting of 0, 1, 2, 3, 4, and 5;

provided that when one of t or u is 0, the other of t or u is not 0.

When the substituent is halo, this is selected from fluoro, chloro, bromo or iodo.

In one embodiment are groups X having from 3 to 30, preferably 3 to 24, more preferably from 3 to 15 carbon atoms, including those of any alicyclic or aromatic rings, if present. Such groups are straight or branched, and in the case of the latter contain one or more, for example two or three branch points and are saturated or unsaturated, in the case of the latter containing one to four, for example 1, 2, 3 or 4, double or triple bonds.

In one embodiment X is of formula $R^{27}CO$— wherein $R^{27}$ is a lipophilic group having from 3 to 15 carbon atoms, wherein said lipophilic group is:

straight or branched and may include an alicyclic or aromatic ring, the total number of carbon atoms in the group including those of any such ring;

is saturated or unsaturated, in the case of the latter containing one to four double or triple bonds;

optionally having 1 or 2 heteroatoms (in addition to those, if present, in aromatic rings, if present), independently selected from O or N;

optionally containing one or two aromatic rings, either or both of which may contain 1 nitrogen heteroatom; and optionally having from one to three substituents selected from hydroxyl, amino, methyl, methylamino and halo.

In one embodiment X is an alkanoic acid of formula $C_jH_{(2j+1)}CO$—, wherein j is selected from 7, 8, 9, 10, 11, 12 or 13, exemplary such groups being $nC_7CO$-$(nC_7H_{15}CO$—); $nC_8CO$-$(nC_8H_{17}CO$—); $nC_9CO$-$(nC_9H_{19}CO$—); $nC_{10}CO$-$(nC_{10}H_{21}CO$—); $nC_{11}CO$-$(nC_{11}H_{23}CO$—), $nC_{12}CO$-$(nC_{12}H_{25}CO$—) and $nC_{13}CO$-$(nC_{13}H_{27}CO$—).

In one embodiment X is selected from:
$nC_{10}CO$—; $nC_{13}CO$—; 4-PhO-PhCO—; [(4-PhO-PhCO)Lys(4-PhO-PhCO)—; $(nC_{10}CO)Lys(COnC_{10})$—; $nC_{10}CO$-Gly-; $nC_{11}CO$—; $nC_{12}CO$—; (4-PhO-PhCO)-Gly-; $nC_7CO$—; $nC_8CO$—; $nC_9CO$—; (2-Bu-$nC_7CO$)—; [(2-Bu-$nC_7CO$—)Lys(2-Bu-$nC_7CO$)]—; (9Z-9,10-dehydro-$nC_{13}CO$)—; $C_6PhCO$—; $C_7PhCO$—; $C_5OPhCO$—; $(C_5OPhCO)Lys(C_5OPhCO)$—; $C_7OPhCO$—; $C_9OPhCO$—; $PhOC_3CO$—; [$PhOC_3CO$-Lys($PhOC_3CO$)]—; $PhC_5CO$—; [$PhC_5CO$-Lys($PhC_5CO$)]—; $PhC_8CO$—; $PhC_9CO$—; $PhC_{11}CO$—; (4-Ph-PhC1CO)—; [(4-Ph-$PhC_1CO$)-Lys(4-Ph-$PhC_1CO$)]—; [4-(4-F-PhO)-PhCO]—; {[4-(4-Cl-PhO)-PhCO-Lys[4-(4-F-PhO)-PhCO]}—; [4-(4-Cl-PhO)-PhCO]—; {[4-(4-Cl-PhO)-PhCO-Lys[4-(4-Cl-PhO)-PhCO]}—; (4-BnO-PhCO)—; [(4-BnO-PhCO)-Lys(4-BnO-PhCO)]—; ($nC_9$-pip-4-CO)—; [$nC_7CO$-Lys($COnC_7$)]—; [($C_9OPhCO$)-Lys($C_9OPhCO$)]—; [($PhOC_3CO$)-Lys($PhOC_3CO$)]—; {[4-(4-F-PhO)-PhCO-Lys[4-(4-F-PhO)-PhCO]}—; [$PhC_{11}CO$-Lys($PhC_{11}CO$)]—; $nC_{10}CH_2$—; 4-PhO-$PhCH_2$—; $CH_3Ph$-$SO_2$—; [$nC_{12}CO$-Lys($nC_{12}CO$)]—; [$nC_{13}CO$-Lys($nC_{13}CO$)]—; (2-Bu-$C_7CO$)-Lys(2-Bu-$C_7CO$)—; $(nC_9CH_2)_2$—; $nC_{13}CH_2$—; $PhCH_2$—; ($nC_{11}$-Pip-4-CO)—; ($nC_7$-Pip-4-CO)—; (1-$nC_9$-Pro)-; ($nC$-Pip-2-CO)—; (4-$NH_2$-PhCO)—; (4-MeNH-PhCO)—; (4-$nC_7$NH-PhCO)—; $(nC_4CH_2$—$)_2$; $nC_8CH_2$—; (2-$NH_2$-$nC_9CO$)—, 3,5-$Me_2C_7CO$—; 3-OH—$C_9CO$—; (4-Cl-PhCO)—; $cHexCH_2CO$— and 4-$nC_5$-cHexCO—.

Element W

In the compounds of the present invention, W is a basic amino acid or a basic peptide consisting of from 2 to 10 amino acids, provided that W is not or does not contain any amino acids with a sulphur-containing side chain.

Thus, W may be a single basic amino acid or a basic peptide consisting of 2, 3, 4, 5, 6, 7, 8, 9 or 10 amino acids.

In a particular embodiment W is a basic amino acid or a basic peptide consisting of from 2 to 5 amino acids, provided that W is not or does not contain any amino acids with a sulphur-containing side chain, that is W may be a single basic amino acid or a basic peptide consisting of 2, 3, 4 or 5 amino acids.

W is not or does not contain any amino acids with a sulphur-containing side chain. W thus does not contain any Met or Cys residues.

In a particular embodiment, W consists of one, two or three basic amino acids.

A basic peptide is a peptide containing side chains with a net overall positive charge under physiological conditions (e.g approximately pH 5-8). The exact nature of the amino acids is not essential, so long as the net overall charge of the peptide formed therefrom is positive under physiological conditions. This is readily recognised as a peptide containing at least one basic residue (e.g. Arg, Lys, Orn, Dab, Dap, His). The peptide may contain other amino acids, such as Gly or Ser, or one or more acidic residues (e.g. Asp, Glu) provided that any such acidic residue is offset by an additional basic residue, i.e. such that the total number of acidic residues in the peptide is less than the total number of basic residues and the resulting peptide has a net overall positive charge under physiological conditions.

In the compounds of the invention, the N-terminus of W is attached to X and the C-terminus of W is attached to L.

Peptides may be prepared recombinantly or synthetically, e.g. by step-wise synthesis. Alternatively, the peptides may be recovered from cultures of cells which naturally produce the peptide, e.g. in the case of membrane associating peptides produced by bacteria.

Peptides produced by synthetic means will generally be composed of natural L-amino acids (i.e. those encoded by the genetic code, the so-called proteinogenic amino acids), although D-amino acids or racemic amino acids may also be used. Non-proteinogenic amino acids, isolated from natural sources or prepared by synthetic methods, may also be used. In this invention, the group W may be or consist of either proteinogenic or non-proteinogenic amino acids, or a mixture thereof.

In every case, side chain modifications may be performed, for example in order to enhance in vivo half-life or improve stability. Side chain modifications include for example, modifications of amino groups by reductive alkylation by reaction with an aldehyde followed by reduction with sodium borohydride, alkylation by nucleophilic displacement of an alkyl bromide, amidination with methylacetimidate or acylation with acetic anhydride.

The guanidine groups of arginine residues may be modified by alkylation or by the formation of heterocyclic condensation products with reagents such as 2,3-butanedione or glyoxal. Tryptophan residues may be modified by oxidation or alkylation of the indole ring and the imidazole ring of histidine residues may be modified by alkylation.

Any other carboxy side chains may be blocked in the form of an ester group, e.g. a C1-6 alkyl ester or in the form of an amide.

The above examples of modifications to amino acids are not exhaustive. Those of skill in the art may modify amino acid side chains where desired using chemistry known per se in the art.

Peptides recovered from naturally occurring sources may contain non-proteinogenic amino acids, which are produced either by post translational modification of proteinogenic amino acids, or by biosynthesis.

In a particular embodiment of the invention, W consists of 1 residue or 2 to 10 contiguous residues, more preferably 1 residue or from 2 to 5 contiguous residues of the formula (V):

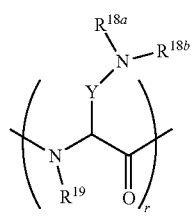

(V)

in which:

Y is a group of formula —$(CR^{20}R^{21})_g$—;

$R^{18a}$ is selected from the group consisting of H, optionally substituted $C_1$-$C_{12}$alkyl, optionally substituted $C_2$-$C_{12}$alkenyl, optionally substituted $C_2$-$C_{12}$alkynyl, optionally substituted $C_1$-$C_{12}$heteroalkyl, optionally substituted $C_3$-$C_{12}$cycloalkyl, optionally substituted $C_2$-$C_{12}$heterocycloalkyl, optionally substituted $C_6$-$C_{18}$aryl, optionally substituted $C_1$-$C_{18}$heteroaryl, —C(=$NR^{22}$)—$NR^{23}R^{24}$, and $OR^{22}$, $R^{18b}$ is selected from the group consisting of H, optionally substituted $C_1$-$C_{12}$alkyl, optionally substituted $C_2$-$C_{12}$alkenyl, optionally substituted $C_2$-$C_{12}$alkynyl, optionally substituted $C_1$-$C_{12}$heteroalkyl, optionally substituted $C_3$-$C_{12}$cycloalkyl, optionally substituted $C_2$-$C_{12}$heterocycloalkyl, optionally substituted $C_6$-$C_{18}$aryl, and optionally substituted $C_1$-$C_{18}$heteroaryl, or $R^{18a}$ and $R^{18b}$ when taken together with the nitrogen atom to which they are attached form an optionally substituted heterocyclic moiety, or one of $R^{18a}$ and $R^{18b}$ when taken together with any $R^{20}$ or $R^{21}$ and the atoms to which they are attached forms an optionally substituted heterocyclic moiety;

$R^{19}$ is selected from the group consisting of H and optionally substituted $C_1$-$C_{12}$alkyl;

$R^{20}$ and $R^{21}$ are each independently selected from the group consisting of H, halogen, OH, $C_1$-$C_{12}$alkyl, $C_6$-$C_{18}$aryl, $C_1$-$C_{12}$haloalkyl, $C_1$-$C_{12}$hydroxyalkyl, $C_1$-$C_{12}$alkyloxy and $C_1$-$C_{12}$haloalkyloxy, or when taken together with the carbon to which they are attached $R^{20}$ and $R^{21}$ form an optionally substituted $C_3$-$C_{12}$cycloalkyl, or an optionally substituted $C_1$-$C_{12}$heterocycloalkyl group, or one of $R^{20}$ and $R^{21}$ when taken together with one of $R^{18a}$ and $R^{18b}$ and the atoms to which they are attached form an optionally substituted heterocyclic moiety;

each $R^{22}$, $R^{23}$, and $R^{24}$ is independently selected from the group consisting of H, optionally substituted $C_1$-$C_{12}$alkyl, optionally substituted $C_1$-$C_{12}$heteroalkyl, optionally substituted $C_3$-$C_{12}$cycloalkyl, optionally substituted $C_6$-$C_{18}$aryl, and optionally substituted $C_1$-$C_{18}$heteroaryl, or any two of $R^{22}$, $R^{23}$ and $R^{24}$ when taken together with the atoms to which they are attached form an optionally substituted cyclic group;

g is an integer selected from the group consisting of 1, 2, 3, 4, and 5;

r is an integer selected from the group consisting of 1, 2, 3, 4, 5, 6, 7, 8, 9 and 10.

In a particular embodiment, in formula (V) Y is $(CH_2)_g$, wherein g is as defined above.

In a particular embodiment, W is an amino acid or is a peptide comprising or consisting of amino acids selected from optionally substituted D- or L-lysine, ornithine, 2,4-diaminobutyric acid, 2,3-diaminopropionic acid and arginine.

In a particular embodiment, W is selected from the group consisting of -Lys-, -Lys-Lys-, -Lys-Lys-Lys-, -Orn-, -Orn-Orn-, -Orn-Orn-Orn-, -Lys-Orn-, -Orn-Lys, -Dab-, -Dab-Dab-, -Lys-Dab-, -Dab-Lys-, -Dab-Orn-, -Orn-Dab-, -Dap-, -Dap-Dap-, -Dap-Lys-, -Lys-Dap, -Dap-Orn, -Orn-Dap, -Dap-Dab-, and -Dab-Dap-, in which any of the amino acids may be of the -L- or -D- configuration.

It will be understood that unless indicated to the contrary, amino acid sequences are represented herein using standard notation and in the N- to C-terminal direction.

Linking Group L

In the compounds of the invention, L is a linking group of the formula:

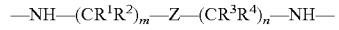

wherein:

Z is oxygen or an optionally substituted moiety selected from the group consisting of —NH—, —CONH—, —NHCO—, —$(OCH_2CH_2)_p$—, $C_1$-$C_{12}$alkyl, $C_2$-$C_{12}$alkenyl, $C_2$-$C_{12}$alkynyl, $C_1$-$C_{12}$heteroalkyl, $C_1$-$C_{10}$heteroalkenyl, $C_3$-$C_{12}$cycloalkyl, $C_1$-$C_{12}$heterocycle, $C_6$-$C_{18}$aryl, or $C_1$-$C_{12}$heteroaryl; and $R^1$, $R^2$, $R^3$, and $R^4$ are each independently selected from the group consisting of H, halogen, optionally substituted $C_1$-$C_{12}$alkyl, optionally substituted $C_2$-$C_{12}$alkenyl, optionally substituted $C_2$-$C_{12}$alkynyl, optionally substituted $C_1$-$C_{12}$heteroalkyl, optionally substituted $C_1$-$C_{10}$heteroalkenyl, optionally substituted $C_3$-$C_{12}$cycloalkyl, optionally substituted $C_1$-$C_{12}$heterocycle, optionally substituted $C_6$-$C_{18}$aryl, optionally substituted $C_1$-$C_{18}$heteroaryl, optionally substituted carboxy, optionally substituted carboxamide; and m is an integer selected from the group consisting of 0, 1, 2, and 3; and n is an integer selected from the group consisting of 0, 1, 2, and 3;

provided that both of m and n are not 0; and p is an integer selected from the group consisting of 1-10; or L is selected from one of the formulae:

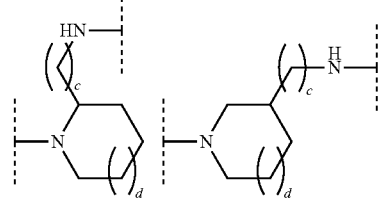

-continued

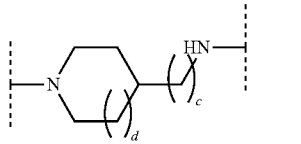

wherein c and d are integers selected from the group consisting of 0, 1, and 2; and the dotted lines show points of attachment to V and W.

When L is of formula —NH—$(CR^1R^2)_m$—Z—$(CR^3R^4)_n$—NH—, one amine is attached to the C-terminus carboxyl of W via an amide linkage and attachment to V is via an amide linkage to the glycopeptide free carboxyl group.

When L is selected from one of the formulae illustrated above, particular compounds are those in which the ring amine is bonded to group W and the exocyclic amine group is bonded to group V.

In a particular aspect, -L- is of the formula —NH—$(CH_2)_m$—Z—$(CH_2)_n$—NH—; wherein Z, m and n are as defined above.

When -L- is of the formula —NH—$(CH_2)_m$—Z—$(CH_2)_n$—NH—, particular compounds are those in which Z is selected from the group consisting of $C_1$-$C_{12}$ alkyl, NH, O, $C_1$-$C_{12}$heterocycle, $C_6$-$C_{18}$aryl or $C_3$-$C_{12}$cycloalkyl, more preferably $C_1$-$C_6$alkyl, NH, O, phenyl or cyclohexyl.

In this aspect, particular groups -L- are of the formula —NH—$(CH_2)_2$—NH—, —NH—$(CH_2)_3$—NH—, —NH—$(CH_2)_4$—NH—, —NH—$(CH_2)_2$—NH—$(CH_2)_2$—NH—, —NH—$(CH_2)_4$—O—$(CH_2)_2$—NH—, —NH—$(CH_2)_3$—O—$(CH_2)_3$—NH—, —NH-(1,4-Ph)-$CH_2$—NH—, —NH-(1,3-Ph)-$CH_2$—NH—, —NH-(1,4-cHex)-$CH_2$—NH—, or —NH—$CH_2$-(1,4-cHex)-$CH_2$—NH—.

Alternatively, -L- is of the formula —NH—$CH(R^1)$—Z—$(CH_2)_n$—NH— wherein:

$R^1$ is —(CO)OH, —(CO)OMe, —$(CO)NH_2$, —(CO)NHNH_2, —(CO)NHMe, —(CO)NHEt, —(CO)N(Me)_2, —(CO)NHBn or —(CO)$R^5$ or an optionally substituted $C_1$-$C_{12}$heterocycle or an optionally substituted $C_1$-$C_{18}$heteroaryl moiety; and $R^5$ is an optionally substituted $C_1$-$C_{12}$heterocycle or an optionally substituted $C_1$-$C_{18}$heteroaryl moiety; and Z and n are as defined above.

In this aspect, particular compounds are those in which -L- is of the formula —NH—$CH(R^1)$—$(CH_2)_q$—NH— wherein:

q is an integer selected from the group consisting of 0, 1, 2, 3, 4, and 5; and $R^1$ is —(CO)OH, —(CO)OMe, —$(CO)NH_2$, —(CO)NHNH_2, —(CO)NHMe, —(CO)NHEt, —(CO)N(Me)_2, —(CO)NHBn or —(CO)$R^5$ or an optionally substituted $C_1$-$C_{12}$heterocycle or an optionally substituted $C_1$-$C_{18}$heteroaryl moiety.

When -L- is of the formula —NH—$CH(R^1)$—$(CH_2)_q$—NH—, particular compounds are those in which q is an integer selected from the group consisting of 2, 3 or 4 and/or $R^1$ is selected from the group consisting of —CO(OH), —$CO(NH_2)$ and —CO(NHMe).

Particular compounds of this invention are those in which -L- is selected from:

(R)— or (S)—NHCH(COOH)$(CH_2)_4$NH—;
(R)— or (S)—NHCH(CONHMe)$(CH_2)_4$NHCOCH$_2$NH—;
(R)— or (S)—NHCH(COOH)$(CH_2)_4$NHCOCH$_2$NH—;
(R)— or (S)—NHCH$_2$CO—NH$(CH_2)_2$NH—;
(R)— or (S)—NHCH(CONH$_2$)—CH$_2$-(1,3-triazole)-(CH$_2)_3$—NH—;
(R)— or (S)—NHCH(CONH$_2$)$(CH_2)_4$NH—;
(R)— or (S)—NHCH(CONHMe)$(CH_2)_4$NH—;
(R)— or (S)—NHCH(COOMe)$(CH_2)_4$NH—;
(R)— or (S)—NHCH(CONHMe)$(CH_2)_3$NH—;
(R)— or (S)—NHCH(CONHMe)$(CH_2)_2$NH—;
(R)— or (S)—NHCH(CONH$_2$)$(CH_2)_3$NH—;
(R)— or (S)—NHCH(CONH$_2$)$(CH_2)_2$NH—;
(R)— or (S)—NHCH(COOH)$(CH_2)_3$NH—;
(R)— or (S)—NHCH(COOH)$(CH_2)_2$NH—;
(R)— or (S)—NHCH$_2$CO—NH$(CH_2)_3$NH—;
(R)— or (S)—NHCH(CONHnC14)$(CH_2)_4$NH—;
(R)— or (S)—NHCH(CONHEt)$(CH_2)_4$NH—;
(R)— or (S)—NHCH(CONHBn)$(CH_2)_4$NH—;
—NH$(CH_2)_2$NH—;
—NH$(CH_2)_3$NH—;
—NH$(CH_2)_4$NH—;
—NH$(CH_2)_5$NH—;
—NH$(CH_2)_6$NH—;
—NH$(CH_2)_2$NH$(CH_2)_2$NH—;
—NH$(CH_2)_2$O$(CH_2)_2$NH—;
—NH$(CH_2)_2$O$(CH_2)_2$O$(CH_2)_2$NH—;
—NHCH$_2$(1,3-Ph) CH$_2$NH—;
—NHCH$_2$(1,4-Ph)CH$_2$NH—;
—NH(1,4-cHex)NH—;
—NHCH$_2$ (1,4-cHex) CH$_2$NH—;
-1-piperidine-4-CH$_2$NH—;
-1-piperidine-2-CH$_2$NH—; and
-1-piperidine-2-NH—.

More particularly, -L- is selected from:
(R)— or (S)—NHCH(CONHMe)$(CH_2)_4$NH—;
(R)— or (S)—NHCH(CONH$_2$)$(CH_2)_4$NH—;
(R)— or (S)—NHCH(COOH)$(CH_2)_4$NH—;
—NH$(CH_2)_2$NH—; and
—NH$(CH_2)_3$NH—.

Element V.

In the compounds of the present invention, V is a glycopeptide moiety which inhibits peptidoglycan synthesis in bacteria.

The first two stages of peptidoglycan occur inside the bacterial cell. Stage 1 involves the assembly of an N-acetylmuramic acid based lipid with a linked pentapeptide, the peptide being: L-Alanine-γ-D-Glutamate-m-Xaa-D-Alanine-D-Alanine, where Xaa is usually D-amino-pimelic acid but in some species (e.g. Staph aureus) is L-lysine. The γ-D-Glutamate residue can also be modified by amidation of the α-acid group.

In the second stage, the lipid is extended by N-acetyl glucosamine. This lipid is subsequently transported across the cell membrane.

The third stage, which takes place on the exterior surface of the bacterial membrane, involves the polymerization of the lipid-linked GlcNAc-MurNAC-disaccharide by a transglycolase and the cross-linking of the peptide side chains by a transpeptidase.

The best known compound of the class of inhibitors of this biosynthesis pathway is vancomycin, which, as discussed above, is known to inhibit peptidoglycan biosynthesis by binding to the D-Ala-D-Ala dipeptide terminus of the pentapeptide of the bacterial cell wall peptidoglycan precursors, preventing their further processing into peptidoglycan.

Derivatives of vancomycin also act by inhibiting the biosynthesis of peptidoglycan. A series of compounds alkylated on the vancosamine sugar has been shown to have activity against vancomycin resistant bacteria, along with analogous compounds derivatized with a further sugar (Cooper, R. D. G. et al. 1996, supra; Rodriguez, M. J. et al., 1998, supra; and Ge, M., Chen, Z., Onishi, H. R., Kohler, J., Silver, L. L., Kerns, R., Fukuzawa, S., Thompson, C., and Kahne, D. (1999) Vancomycin derivatives that inhibit peptidoglycan biosynthesis without binding D-Ala-D-Ala, Science 284, 507-511).

In general terms, those of skill in the art are familiar with glycopeptides which inhibit peptidoglycan biosynthesis in bacteria and may select suitable glycopeptides for use in the present invention. Such glycopeptides are typically of a molecular weight of from 1000 to 3000 Da, are capable of interaction with individual components of the Lipid II or bacterial peptidoglycan structure such as the Lys-D-Ala-D-Ala peptide, the Lys-D-Ala-D-Lactate depsipeptide, and components of the lipid GlcNAc-MurNAC-pentapeptide, and are active against vancomycin-susceptible reference strains (e.g. selected from any one of reference strains *S. aureus* NCTC (National Collection of Type Cultures) 6571, *S. aureus* ATCC 25923 (NCTC 12981), *S. aureus* ATCC 29213 (NCTC 12973), *Streptococcus pneumoniae* ATCC 49619 (NCTC 12977) and *Enterococcus faecalis* ATCC 29212 (NCTC 12697)) at a MIC of less than or equal to 4 µg/ml. Accepted standard methods for MIC testing include the agar dilution method or the broth dilution method, with both methods contained within the reference standard document Clinical and Laboratory Standards Institute (CLSI) M07-A9 (Methods for Dilution Antimicrobial Susceptibility Tests for Bacteria that Grow Aerobically; Approved Standard—Ninth Edition) and published in J. Antimicrob. Chemother. (2001) 48 (suppl 1): 5-16.

In a particular embodiment herein, element V is a derivative of vancomycin. Particular vancomycin derivatives which are contemplated as the element or moiety V include compounds based on the glycopepeptides disclosed in WO 96/30401 and WO 98/00153, and salts thereof, the disclosures of which are herein incorporated by reference.

In a particular embodiment, V is selected from vancomycin, vancomycin aglycon, vancomycin desvancosamine, desmethyl vancomycin, chloroeremomycin, teicoplanain-$A_2$-2, ristocetin A, eremomycin, balhimycin, actinoidin A, complestatin, chloropeptin 1, kistamycin A, avoparcin, telavancin, A40926 and oritavancin, and any one thereof optionally substituted on a primary amine with $R^{17}$, wherein $R^{17}$ is an organic side chain moiety selected from the group consisting of hydrogen, optionally substituted $C_1$-$C_{12}$alkyl, optionally substituted $C_2$-$C_{12}$alkenyl, optionally substituted $C_2$-$C_{12}$alkynyl, optionally substituted $C_1$-$C_{12}$ heteroalkyl, optionally substituted $C_1$-$C_{10}$ heteroalkenyl, optionally substituted $C_3$-$C_{12}$cycloalkyl, optionally substituted $C_2$-$C_{12}$ heterocycloalkyl, optionally substituted $C_6$-$C_{18}$aryl, and optionally substituted $C_1$-$C_{18}$heteroaryl.

In a more particular embodiment, V is selected from vancomycin, vancomycin aglycon, desvancosamine vancomycin, or telavancin. Most particularly, V is vancomycin.

In the invention, the X—W-L- component of the compound of formula (III) is attached via an amide linkage between the group L and the glycopeptide free carboxyl group.

In one aspect of this invention, X—W-L-V is of formula (VI):

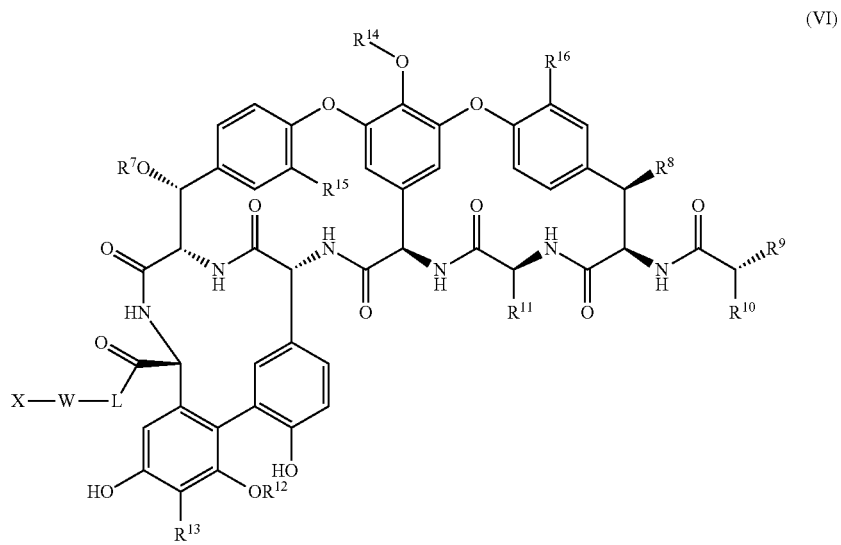

(VI)

in which: X, W and L are as defined above;
$R^7$ is hydrogen, a carbohydrate, or an amino carbohydrate;
$R^8$ is hydrogen, OH, or —O-mannose;
$R^9$ is —NH$_2$, —NHCH$_3$, or —N(CH$_3$)$_2$;
$R^{10}$ is —CH$_2$CH(CH$_3$)$_2$, [p-OH, m-Cl]phenyl, p-rhamnose-phenyl, [p-rhamnose-galactose]phenyl, [p-galactose-galactose]phenyl, [p-CH$_3$O-rhamnose]phenyl, or is linked to $R^{11}$ via [p-OH,m-(O-{m-OH,m-$R^{11}$}-phenyl)]phenyl to form a cyclic ring system;
$R^{11}$ is —CH$_2$—(CO)NH$_2$, benzyl, [p-OH]phenyl, [p-OH, m-Cl]phenyl; [p-OH, m-Cl]phenyl, or is linked to $R^{10}$ via [m-OH,m-(O-{o-OH,m-$R^{10}$}phenyl)]-phenyl to form a cyclic ring system;
$R^{12}$ is hydrogen, or mannose;
$R^{13}$ is hydrogen, OH, or CH$_2$NHCH$_2$PO$_3$H$_2$;
$R^{14}$ is hydrogen, beta-D-glucopyranose, beta-D-glucosamine, 2-O-(alpha-L-vancosaminyl)-beta-D-glucopyranose, 2-O-(alpha-L-4-epi-vancosaminyl)-beta-D-glucopyranose, (alpha-actinosaminyl)-beta-D-glucopyranose, (alpha-ristosaminyl)-beta-D-glucopyranose, or (alpha-acosaminyl)-beta-D-glucopyranose; or any one of said glucosamine or glucopyranose groups optionally substituted on a primary amine thereof with $R^{17}$, wherein $R^{17}$ is as defined above; and
$R^{15}$ and $R^{16}$ are independently hydrogen or chloro.

In a particular aspect, in compounds of formula (VI) $R^7$ is H, 4-epi-vancosaminyl, actinosaminyl, or ristosaminyl.

A particular group of compounds of the present invention are compounds of formula (III), above, in which:
  X is of formula $R^{27}CO$— wherein $R^{27}$ is a lipophilic group having from 3 to 15 carbon atoms, wherein said lipophilic group is:
    straight or branched and may include an alicyclic or aromatic ring, the total number of carbon atoms in the group including those of any such ring;
    is saturated or unsaturated, in the case of the latter containing one to four double or triple bonds;
    optionally having 1 or 2 heteroatoms (in addition to those, if present, in aromatic rings, if present), independently selected from O or N;
    optionally containing one or two aromatic rings, either or both of which may contain 1 nitrogen heteroatom; and
    optionally having from one to three substituents selected from hydroxyl, amino, methyl, methylamino and halo;
  W is an amino acid or is a peptide consisting of from 2 to 5 proteinogenic or non-proteinogenic amino acids selected from optionally substituted D- or L- lysine, ornithine, 2,4-diaminobutyric acid, 2,3-diaminopropionic acid and arginine;
  L is of the formula —NH—$(CH_2)_m$—Z—$(CH_2)_n$—NH—; wherein Z, m and n are as defined above; and
  V is selected from vancomycin, vancomycin aglycon, vancomycin desvancosamine, desmethyl vancomycin, chloroeremomycin, teicoplanain-$A_2$-2, ristocetin A, eremomycin, balhimycin, actinoidin A, complestatin, chloropeptin 1, kistamycin A, avoparcin, telavancin, A40926 and oritavancin, and any one thereof optionally substituted on a primary amine with $R^{17}$, wherein $R^{17}$ is an organic side chain moiety selected from the group consisting of hydrogen, optionally substituted $C_1$-$C_{12}$alkyl, optionally substituted $C_2$-$C_{12}$alkenyl, optionally substituted $C_2$-$C_{12}$alkynyl, optionally substituted $C_1$-$C_{12}$ heteroalkyl, optionally substituted $C_1$-$C_1$ heteroalkenyl, optionally substituted $C_3$-$C_{12}$cycloalkyl, optionally substituted $C_2$-$C_{12}$ heterocycloalkyl, optionally substituted $C_6$-$C_{18}$aryl, and optionally substituted $C_1$-$C_{18}$heteroaryl.

Another particular group of compounds of the present invention are compounds of formula (III), above, in which:
  X is an alkanoic acid of formula $C_jH_{(2j+1)}CO$—, wherein j is selected from 7, 8, 9, 10, 11, 12 or 13;
  W is a basic amino acid or a basic peptide consisting of two or three amino acid residues, wherein each amino acid as or within W is selected from the group consisting of L-lysine, D-lysine, ornithine, 2,4-diaminobutyric acid and 2,3-diaminopropionic acid;
  L is selected from the group consisting of:
    (R)— or (S)—NHCH(CONHMe)$(CH_2)_4$NH—;
    (R)— or (S)—NHCH(CONH$_2$)$(CH_2)_4$NH—;
    (R)— or (S)—NHCH(COOH)$(CH_2)_4$NH—;
    —NH$(CH_2)_2$NH—; or
    —NH$(CH_2)_3$NH—; and
  V is selected from the group consisting of vancomycin, vancomycin aglycon, vancomycin desvancosamine and desmethyl-vancomycin.

Particular compounds may be any one or more of the compounds illustrated in Table 2, below.

In the compounds of the invention, reference is made to optional substituents. When any substituent is present, each is independently selected from the group consisting of: halogen (e.g. chlorine, fluorine, bromine or iodine), =O, =S, —CN, —NO$_2$, —CF$_3$, —OCF$_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, cycloalkylalkyl, heterocycloalkylalkyl, heteroarylalkyl, arylalkyl, cycloalkylalkenyl, heterocycloalkylalkenyl, arylalkenyl, heteroarylalkenyl, cycloalkylheteroalkyl, heterocycloalkylheteroalkyl, arylheteroalkyl, heteroarylheteroalkyl, hydroxy, hydroxyalkyl, alkyloxy, alkyloxyalkyl, alkyloxycycloalkyl, alkyloxyheterocycloalkyl, alkyloxyaryl, alkyloxyheteroaryl, alkyloxycarbonyl, alkylaminocarbonyl, alkenyloxy, alkynyloxy, cycloalkyloxy, cycloalkenyloxy, heterocycloalkyloxy, heterocycloalkenyloxy, aryloxy, phenoxy, benzyloxy, heteroaryloxy, arylalkyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, alkylsulfinyl, arylsulfinyl, aminosulfinylaminoalkyl, —C(=O)OH, —C(=O)Ra, C(=O)OR$_a$, C(=O)NR$_a$R$_b$, C(=NOH)R$_a$, C(=NR$_a$)NR$_b$R$_c$, NR$_a$R$_b$, NR$_a$C(=O)R$_b$, NR$_a$C(=O)OR$_b$, NR$_a$C(=O)NR$_b$R$_c$, NR$_a$C(=NR$_b$)NR$_c$R$_d$, NR$_a$SO$_2$R$_b$, —SRa, SO$_2$NRaRb, —OR$_a$, OC(=O)NR$_a$R$_b$, OC(=O)R$_a$ and acyl,
  wherein R$_a$, R$_b$, R$_c$ and R$_d$ are each independently selected from the group consisting of H, $C_1$-$C_{12}$ alkyl, $C_1$-$C_{12}$ haloalkyl, $C_2$-$C_{12}$ alkenyl, $C_2$-$C_{12}$ alkynyl, $C_1$-$C_{10}$ heteroalkyl, $C_3$-$C_{12}$ cycloalkyl, $C_3$-$C_{12}$ cycloalkenyl, $C_1$-$C_{12}$ heterocycloalkyl, $C_1$-$C_{12}$ heterocycloalkenyl, $C_6$-$C_{18}$aryl, $C_1$-$C_{18}$heteroaryl, and acyl, or any two or more of R$_a$, R$_b$, R$_c$ and R$_d$, when taken together with the atoms to which they are attached form a heterocyclic ring system with 3 to 12 ring atoms.

In the present invention, when a group is a $C_1$-$C_{12}$ alkyl, this is a saturated linear or branched hydrocarbon group or chain including, for example, methyl, ethyl, isopropyl, tert-butyl, heptyl, isopropyl, n-octyl, dodecyl, octadecyl, amyl, 2-ethylhexyl, and the like.

In the present invention, when a group is a $C_2$-$C_{12}$ alkenyl, this is an unsaturated linear or branched hydrocarbon group with one or more carbon-carbon double bonds, such as ethenyl, propenyl, butenyl, 1-methyl-2-butenyl, octenyl and the like.

In the present invention, when a group is a $C_2$-$C_{12}$ alkynyl, this is an unsaturated, linear or branched hydrocarbon group with one or more carbon-carbon triple bonds, such as ethynyl, 1-propynyl, 1-butynyl, heptynyl, octynyl and the like.

In the present invention, when a group is a haloalkyl, haloalkenyl or haloalkynyl group, this may be an alkyl group, alkenyl group or alkynyl group as defined above, substituted from one to three times by a halogen atom, such as fluorine, chlorine, bromine or iodine.

When more than one halogen atom is present, these may be the same or different.

In the present invention, when a group is a $C_1$-$C_{10}$ heteroalkyl, this is an alkyl group as defined above in which one or more, particularly 1 to 3 of the carbon atoms is replaced with a heteroatom selected from N, S and O, such as methoxyethyl, ethoxyethyl, N-ethylpropylamine and the like.

In the present invention, when a group is a $C_1$-$C_{10}$ heteroalkenyl, this is an alkenyl group as defined above in which one or more, particlarly 1 to 3 of the carbon atoms is replaced with a heteroatom selected from N, S and O, such as methoxyethenyl, ethoxyethenyl, N-ethylpropenylamine and the like.

In the present invention, when a group is a $C_3$-$C_{12}$ cycloalkyl, this is a closed ring hydrocarbon group, such as cylopropyl, cyclobutyl, cyclopentyl, cyclohexyl and the like.

In the present invention, when a group is a $C_3$-$C_{12}$ cycloalkenyl, this is a closed ring hydrocarbon ring having at least one carbon-carbon double bond, such as cyclopropenyl, cyclobutenyl, cyclopentenyl, cyclohexenyl and the like.

In the present invention, when a group is a $C_1$-$C_{12}$ heterocycle, this is particularly a cycloalkyl group as defined above in which one or more, particularly 1 to 3, of the ring carbon atoms is replaced with a heteroatom selected from N, S and O, such as piperidinyl, morpholino, tetrahydropyranyl, tetrahydrofuranyl, and the like. In the present application, the terms heterocycloalkyl and heterocycle can be used interchangeably.

In the present invention, when a group is a $C_1$-$C_{12}$ heterocycloalkenyl, this is a cycloalkenyl group as defined above in which one or more, particularly 1 to 3 of the ring carbon atoms is replaced with a heteroatom selected from N, S and O, such as 1,2,3,4-tetrahydropyridinyl, 1,2-dihydropyridinyl, 2-pyrrilinyl, 2-imidazolinyl, 2-pyrazolinyl and the like.

In the present invention, when a group is a $C_6$-$C_{18}$aryl, this is a mono- bi- or tri-cyclic carbon ring system having one or two aromatic rings, such as phenyl, naphthyl, tetrahydronaphthyl, indanyl and the like.

In the present invention, when a group is a $C_1$-$C_{18}$heteroaryl, this is an aryl group as defined above in which one or more of the ring carbon atoms has been replaced with one or more, particularly from 1 to 3, heteroatoms selected from N, S and O, such as, thienyl, furyl, pyrrolyl, pyrrolidinyl, imidazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, oxazinyl, triazinyl, thiadiazinyl tetrazolo, 1,5-[b]pyridazinyl and purinyl, as well as benzo-fused derivatives, for example, benzoxazolyl, benzthiazolyl, benzimidazolyl and indolyl and the like.

In the present invention, when a group is a cycloalkylalkyl group, this is an alkyl group as defined above substituted with at least one cycloalkyl group (as defined above), such as n-butylcyclohexyl and the like.

In the present invention, when a group is a heterocycloalkylalkyl group, this is an alkyl group as defined above substituted with at least one heterocycloalkyl group (as defined above), such as n-butylpiperidinyl and the like.

In the present invention, when a group is a heteroarylalkyl group, this is an alkyl group as defined above substituted with at least one heteroaryl group (as defined above), such as 4-pyridylbutyl and the like.

In the present invention, when a group is an arylalkyl group, this is an alkyl group as defined above substituted with at least one aryl group (as defined above), such as 4-phenylbutyl and the like.

In the present invention, when a group is a cycloalkylalkenyl group, this is an alkenyl group as defined above substituted with at least one cycloalkyl group (as defined above), such as 4-cyclohexyl-2-butenyl and the like.

In the present invention, when a group is a heterocycloalkylalkenyl group, this is an alkenyl group as defined above substituted with at least one heterocycloalkyl group (as defined above), such as 4-furanyl-2-butenyl and the like.

In the present invention, when a group is an arylalkenyl group, this is an alkenyl group as defined above substituted with at least one aryl group (as defined above), such as 4-phenyl-2-butenyl and the like.

In the present invention, when a group is a heteroarylalkenyl group, this is an alkenyl group as defined above substituted with at least one heteroaryl group (as defined above), such as 4-pyridyl-2-butenyl and the like.

In the present invention, when a group is a cycloalkylheteroalkyl group, this is a heteroalkyl group as defined above substituted with at least one cycloalkyl group (as defined above), such as 2-cyclohexyl-2-ethoxyethyl and the like.

In the present invention, when a group is a heterocycloalkylheteroalkyl group this is a heteroalkyl group as defined above substituted with at least one heterocycloalkyl group (as defined above), such as 2-piperidine-2-ethoxyethyl and the like.

In the present invention, when a group is arylheteroalkyl group, this is a heteroalkyl group as defined above substituted with at least one aryl group (as defined above), such as 2-phenyl-2-ethoxyethyl and the like.

In the present invention, when a group is a heteroarylheteroalkyl group, this is a heteroalkyl group as defined above substituted with at least one heteroaryl group (as defined above), such as 2-pyridyl-2-ethoxyethyl and the like.

In the present invention, when a group is a hydroxyalkyl, this is an alkyl group as defined above substituted with at least one hydroxyl group, such as 4-hydroxypentyl and the like.

In the present invention, when a group is an alkyloxy, this is an oxygen substituted an alkyl group as defined above, such as methoxy, ethoxy, propoxy, butoxy and the like.

In the present invention, when a group is an alkyloxyalkyl, this is an alkyl group as defined above substituted with at least one alkyloxy group (as defined above), such as 4-methoxypentyl and the like.

In the present invention, when a group is an alkyloxycycloalkyl, this is a cycloalkyl group as defined above substituted with at least one alkyloxy group (as defined above), such as 4-methoxy-cyclohexyl and the like.

In the present invention, when a group is an alkyloxyheterocycloalkyl, this is a heterocycloalkyl group as defined above substituted with at least one alkyloxy group (as defined above), such as 3-methoxypiperidinyl and the like.

In the present invention, when a group is an alkoxyaryl, this is an aryl group as defined above substituted with at least one alkyloxy group (as defined above), such as 4-methoxyphenyl and the like.

In the present invention, when a group is an alkoxyheteroaryl, this is a heteroaryl group as defined above substituted with at least one alkyloxy group (as defined above), such as 4-methoxypyridinyl and the like.

In the present invention, when a group is an alkoxycarbonyl, this is a carbonyl group substituted with an alkoxy group as defined above, such as methoxycarbonyl and the like.

In the present invention, when a group is an alkylaminocarbonyl, this is a carbonyl group substituted with an alkylamino group, such as N-butyl carboxamide and the like.

In the present invention, when a group is an alkenyloxy, this is an oxygen substituted with an alkenyl group as defined above, such as but-2-enyloxy and the like.

In the present invention, when a group is an alkynyloxy, this is an oxygen substituted with an alkynyl group as defined above, such as but-2-ynyloxy and the like.

In the present invention, when a group is a cycloalkyloxy, this is an oxygen substituted with a cycloalkyl group as defined above, such as cyclohexyloxy and the like.

In the present invention, when a group is a cycloalkenyloxy, this is an oxygen substituted with a cycloalkenyl group as defined above, such as cyclohex-3-enyloxy and the like.

In the present invention, when a group is a heterocycloalkyloxy, this is an oxygen substituted with a heterocycloalkyl group as defined above, such as 3-piperidinyloxy and the like.

In the present invention, when a group is a heterocycloalkenyloxy, this is an oxygen substituted with a heterocycloalkenyyl group as defined above, such as 4,5-dehydro-3-piperidinyloxy and the like.

In the present invention, when a group is an aryloxy, this is an oxygen substituted with an aryl group as defined above, such as phenyloxy and the like.

In the present invention, when a group is a heteroaryloxy, this is an oxygen substituted with a heteroaryl group as defined above, such as 3-pyridinyloxy and the like.

In the present invention, when a group is an arylalkyloxy, this is an oxygen substituted with an arylalkyl group as defined above, such as 4-phenylbutoxy and the like.

In the present invention, when a group is an alkylamino, this is an amine substituted with an alkyl group as defined above, such as 4-butylamino and the like.

In the present invention, when a group is an acylamino, this is an amine substituted with an acyl group as defined above, such as acetamide and the like.

In the present invention, when a group is an aminoalkyl, this is an alkyl group as defined above substituted with an amine, such as 4-aminobutyl and the like.

In the present invention, when a group is an arylamino, this is an amine substituted with an aryl group as defined above, such as phenylamino and the like.

In the present invention, when a group is an alkylsulfonyl, this is a sulfonyl group substituted with an alkyl group as defined above, such as butylsulfonyl and the like.

In the present invention, when a group is an arylsulfonyl, this is a sulfonyl group substituted with an aryl group as defined above, such as phenylsulfonyl and the like.

In the present invention, when a group is an alkylsulfinyl, this is a sulfinyl group substituted with an alkyl group as defined above, such as butylsulfinyl and the like.

In the present invention, when a group is an arylsulfinyl, this is a sulfonyl group substituted with an aryl group as defined above, such as phenylsulfinyl and the like.

In the present invention, when a group is an aminosulfinylaminoalkyl, this is an aminoalkyl group substituted on the amine with an aminosulfinyl group, such as aminosulfinylaminopropyl and the like.

In the present invention, when a group is an acyl, this is a group of formula RCO—, wherein R represents an alkyl or aromatic group that is attached to the CO with a single bond, such as formyl, acetyl, propionyl, benzoyl and the like.

Administration of Drug

A further aspect of the present invention is a pharmaceutical composition comprising a compound of formula (III) and a pharmaceutically acceptable carrier.

The formulations optionally comprise other therapeutic ingredients, or diluents. The carrier or carriers must be "acceptable" in the sense of being compatible with the other ingredients of the formulation and not deleterious to the recipients thereof.

Formulations suitable for parenteral or intramuscular administration include aqueous and non-aqueous sterile injection solutions which may contain anti-oxidants, buffers, and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water, for injections, immediately prior to use. Injection solutions and suspensions may be prepared extemporaneously from sterile powders, granules and tablets.

It should be understood that in addition to the ingredients particularly mentioned above, the formulations may include other agents conventional in the art having regard to the type of formulation in question. Of the possible formulations, sterile pyrogen-free aqueous and non-aqueous solutions are preferred.

Alternatively the composition may be formulated for topical application for example in the form of ointments, creams, lotions, eye ointments, eye drops, ear drops, mouthwash, impregnated dressings and sutures, and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

Alternatively the composition may be formulated for inhalational routes for administration (e.g. intranasal, intrapulmonary and the like). Such means include inhalation of aerosol suspensions or insufflation of the compounds of the invention. Nebulizer devices, metered dose inhalers and the like suitable for delivery of the compounds of the invention to the nasal mucosa, trachea and bronchiole are well known in the art and will therefore not be described in detail here. Solid particulate compositions containing respirable dry particles of micronized compositions containing a compound of the invention can be prepared by standard techniques. A solid particulate composition can optionally contain a dispersant which serves to facilitate the formation of an aerosol. A suitable dispersant is lactose, which can be blended with the compound in any suitable ratio, such as a 1 to 1 ratio by weight. The active ingredient can be delivered as a suspension or solution formulation and may involve the use of a liquefied propellant, e.g. a chlorofluorocarbon compound such as dichloroflouromethane, trichlorofluoromethane, dichlorotetrafluoroethane and mixtures thereof. Aerosol formulations can additionally contain one or more co-solvents, for example ethanol, emulsifiers and other formulation surfactants, such as oleic acid or sorbitan trioleate, anti-oxidants and suitable flavouring agents.

Alternatively the composition may be formulated for oral administration. Oral administration can be accomplished using pharmaceutical compositions containing a compound of the invention formulated as tablets, lozenges, aqueous or oily suspensions, dispersible powders or granules, emulsions, hard or soft capsules or syrups or elixirs. Such oral compositions can contain one or more sweetening agents, flavouring agents, colouring agents or preservative agents in order to provide pharmaceutically elegant and palatable preparations. Tablets, which can be coated or uncoated, can be formulated to contain the active ingredient in admixture with non-toxic pharmaceutically acceptable excipients, e.g. inert diluents, such as calcium carbonate, sodium carbonate, lactose, calcium phosphate or sodium phosphate, granulating or disintegrating agents, for example corn starch or alginic acid; binding agents, such as starch, gelatin or acacia; and lubricating agents, for example magnesium stearate, stearic acid or talc. Where a coating is used, the coating delays disintegration and absorption in the gastrointestinal tract and thereby provides a sustained action over a longer period.

When the formulation is an aqueous suspension, such can contain the active agent in a mixture with a suitable excipient. Such excipients can be, as appropriate, suspending agents (e.g. sodium carboxymethylcellulse, methylcellulose, hydropropyl-methylcellulose, sodium alginate, polyvinylpyrrolidone, gum tragacanth and gum acacia); dispersing or wetting agents; preservatives; colouring agents and/or flavouring agents.

The composition of the invention may be administered by injection to achieve a systemic effect against relevant bacteria shortly before insertion of an in-dwelling device. Treatment may be continued after surgery during the in-body time of the device. In addition, the composition could also be used to broaden perioperative cover for any surgical technique to prevent bacterial wound infections.

Many orthopaedic surgeons consider that patients with prosthetic joints should be considered for antibiotic prophylaxis before dental treatment that could produce a bacteraemia. Late deep infection is a serious complication sometimes leading to loss of the prosthetic joint and is accompanied by significant morbidity and mortality. It is therefore possible to extend the use of the peptide or peptide/drug conjugate as a replacement for prophylactic antibiotics in this situation.

Bacterial infections cause one of the major complications associated with the clinical use of implanted materials and in-dwelling devices. In particular, staphylococci have frequently been implicated in medical device-related infections (Dankert et al 1986, CRC Rev Biocompatability 2, 219-301). Once established, the infection is virtually impossible to treat resulting in implant failure. Attempts to combat staphylococcal adhesion to implants have involved modification of the surface of the prosthetic material to discourage adhesion of proteins; e.g. coating with a "non-stick" material such as PTFE, or bonding antibiotics to the surface (Kamal et al., 1991, J. Amer. Med. Assoc. 265, 2364-2368). In addition, there have also been proposals to use non-steroidal anti-inflammatory drugs to prevent adhesion of staphylococci to medical polymers (Farber and Wolff 1992, J. Infect. Dis. 166: 861-865).

For administration to human patients, it is expected that the daily dosage level of the active agent will be from 0.01 to 50 mg/kg, typically around 1 mg/kg. The physician in any event will determine the actual dosage most suitable for an individual patient, and will vary with the age, weight, and response of the particular patient. The above dosages are exemplary of the average case. There can, of course, be individual instances where higher or lower dosage ranges are merited, and such are within the scope of this invention.

In addition to the therapy described above, the compositions of this invention may be used generally as a wound treatment agent to prevent adhesion of bacteria to matrix proteins, especially fibronectin, exposed in wound tissue and for prophylactic use in dental treatment as an alternative to, or in conjunction with, antibiotic prophylaxis.

Alternatively, the composition of the invention may be used to bathe an indwelling device immediately before insertion. The active agent will preferably be present at a concentration of 0.1 µg/ml to 10 mg/ml for bathing of wounds or indwelling devices.

Compositions of the invention may be used for, but are not restricted to, the treatment of bacterial infections caused by the following organisms: *Mycobacterium* sp.; *Enterococcus* sp.; *Staphylococcus* sp.; *Streptococcus* sp.; *Borrelia* sp.; *Clostridium* sp.; *Actinomyces* sp.; and *Pneumococcus* sp.

In a further aspect of the present invention, compounds of formula (III) may be used as a pharmaceutical or in methods of treatment of the animal or human body, and in particular for treatment of bacterial infections caused by the above listed organisms. Compounds of formula (III) may also be used in the manufacture of a medicament for the treatment of bacterial infections, particularly those caused by the above listed organisms.

Synthesis of Compounds

The routes by which compounds of the invention can be synthesised are well known in the art. Generally, compounds may be synthesised by coupling protected element W to element L and then attaching element X thereto. Finally X—W-L is coupled with V and any protecting groups are removed. The resulting compounds may be modified in e.g. the L group to achieve further compounds. In an alternative synthetic route, L is coupled to V and X is coupled to W and as a final step, X—W is coupled to L-V.

EXAMPLES

Embodiments of the present invention will now be described in detail by way of example.

Example 1. General Synthetic Route to Compounds with Lys-OH, Lys-OMe or Lys-NHMe Linker: Solid Phase Synthesis with Solution Phase Glycopeptide Coupling Scheme A

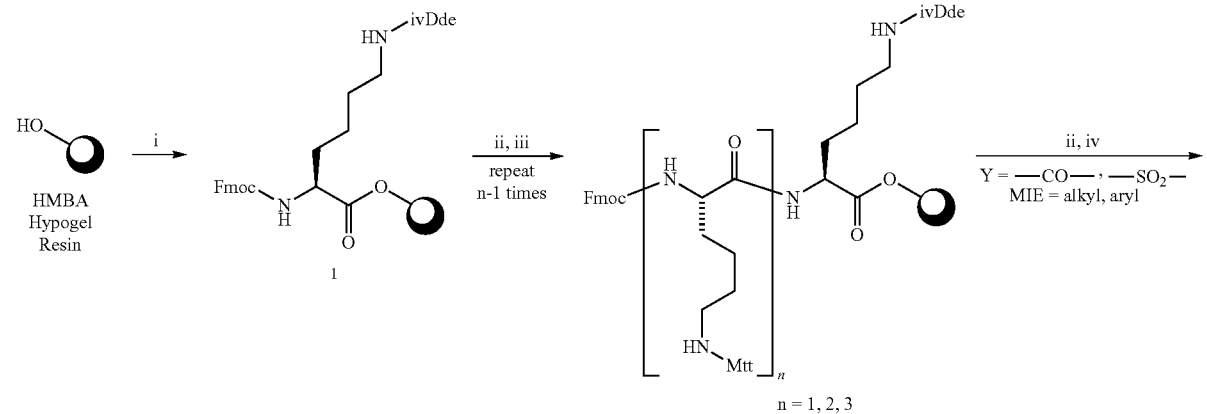

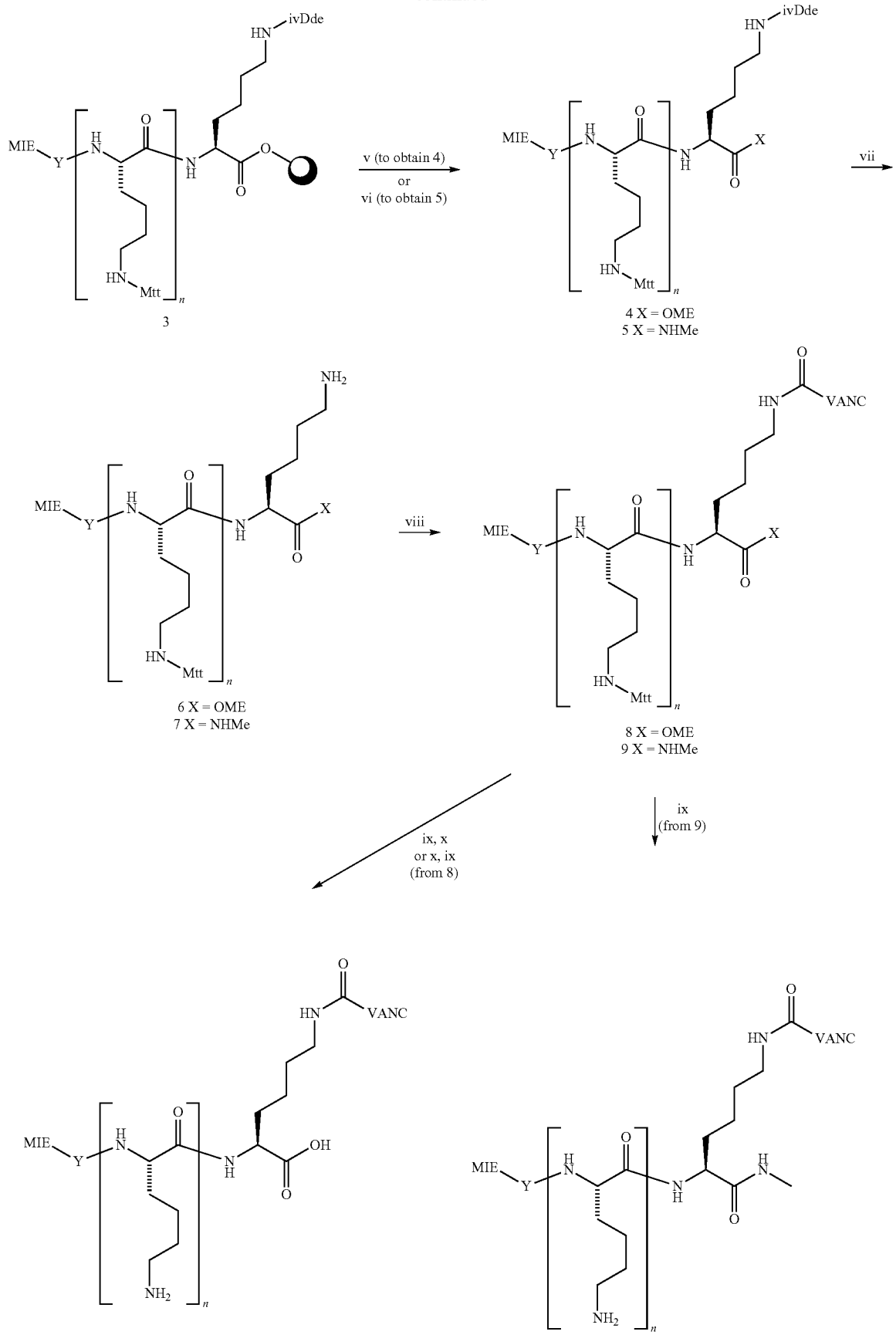

-continued

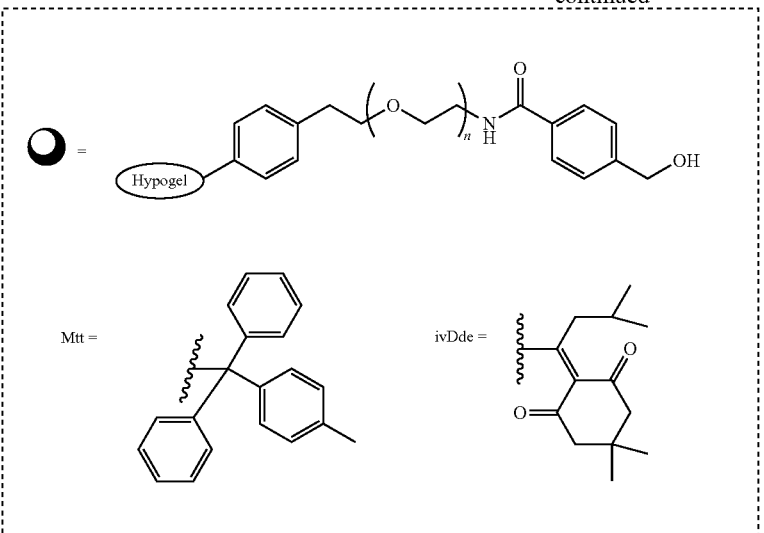

i) Fmoc-L-Lys(ivDde)-OH, DIC, HOBt, DMAP, DMF ii) 20% piperidine in DMF iii) Fmoc-Lys(Mtt)-OH, HBTU, DIPEA, DMF iv) RCOOH, HBTU, DIPEA, DMF or RSO$_2$Cl. DIEA v) MeOH, DIPEA, DMF, 50° C., o/n vi) MeNH$_2$, DIPEA, THF, o/n vii) 2% H$_2$NNH$_2$·H$_2$O in DMF, 1 h viii) Vancomycin·HCl, HBTU, DIPEA, DMSO, DMF, o/n ix) 2% TFA, 5% Et$_3$SiH in DCM, 30 min x) LiOH, Dioxane/H$_2$O (1:1), rt, o/n i). Loading of Fmoc-L-Lys(ivDde)-OH onto Hypogel HMBA Resin:

HypoGel HMBA resin (1.0 g, Loading 0.81 mmol/g, 0.81 mmol) was washed with dry DMF (×3). To a solution of Fmoc-L-Lys(ivDde)-OH (2.33 g, MW 574.7, 4.05 mmol, 5 eq) in dry DMF (10 ml) was added hydroxybenzotriazole (HOBt, 547 mg, MW 135, 4.05 mmol, 5 eq) followed by 1,3-diisopropyldiimide (DIC) (627 µl, d 0.815, MW 126.2, 4.05 mmol, 5 eq) and then 4-dimethylaminopyridine (DMAP, 30 mg, MW 122.17, 0.3 eq). The resulting solution was added to the resin and the resin was shaken at room temperature overnight. The resin was drained, washed with DMF (×3), MeOH (×3) and DCM (×3) and dried in vacuo. In order to cap the resin with acetyl residue, the resin was washed in the glove box with dry DMF (×3) and DIPEA (848 µl) and then acetic anhydride (307 µl, d 1.08, MW 102.09) was added and shaken for 1 h and then drained and washed with DMF (×3), MeOH (×3) and DCM (×3) and dried in vacuo.

ii). Fmoc Deprotection:

The resin (1.45 g, 0.56 mmol/g) was treated with a solution of 20% piperidine in DMF (14.5 ml) and shaken at room temperature for 1 hour. The resin was drained, washed with DMF (×3), MeOH (×3) and DCM (×3), and dried in vacuo.

iii). Peptide Coupling with Fmoc-L-Lys(Mtt)-OH:

The resin (1.27 g, 0.64 mmol/g) was washed with DMF (×3). To a solution of Fmoc-L-Lys(Mtt)-OH (995 mg, MW 624.8, 1.59 mmol, 2.0 eq) in DMF (9.5 ml) was added a solution of HBTU in DMF (3.2 ml, 0.5 M, 1.59 mmol) followed by DIPEA (1107 µl, d 0.742, MW 129.25, 6.35 mmol, 7.8 eq). The solution was allowed to stand for 10 min and then added to the washed resin. The resin was shaken at room temperature for 3 h, drained, washed with DMF (×3), MeOH (×3) and DCM (×3), and dried in vacuo.

iv-a). Peptide Coupling with Various Acids:

The resin (100 mg, 0.043 mmol) was washed with DMF (×3). To a solution of acid in DMF (1 ml) a solution of HBTU in DMF (0.2 ml, 0.5 M), DIPEA (34.9 µl, d 0.742, MW 129.25, 0.5 M final concentration) were added. The solution was allowed to stand for 10 min and then added to the DMF washed resin. The resin was shaken at room temperature for overnight, drained, washed with DMF (×3), MeOH (×3) and DCM (×3), and dried in vacuo.

iv-b). Formation of Sulphonamide:

The resin (100 mg, 0.43 mmol/g) was washed with DMF (×3). To the resin dodecanesulfonylchloride (17.3 mg, MW 268.84, 1.5 eq) in DMF (2 ml), DIPEA (8.9 µl, d 0.742, MW 129.25, 1.2 eq) were added and shaken at room temperature for overnight, drained, washed with DMF (×3), MeOH (×3) and DCM (×3), and dried in vacuo.

iv-c). Peptide Coupling with Fmoc-L-Lys(Fmoc)-OH:

The resin (1.89 g, 0.43 mmol/g) was washed with DMF (×3). To a solution of Fmoc-L-Lys(Fmoc)-OH (1400 mg, MW 624.8, 1.59 mmol, 2.9 eq) in DMF (14.2 ml) was added a solution of HBTU in DMF (4.73 ml, 0.5 M, 2.37 mmol, 2.9 eq) followed by DIPEA (1650 µl, d 0.742, MW 129.25, 6.35 mmol, 11.7 eq). The solution was allowed to stand for 10 min and then added to the washed resin. The resin was shaken at room temperature for 3 h, drained, washed with DMF (×3), MeOH (×3) and DCM (×3), and dried in vacuo. The Fmoc groups were then removed following procedure (ii) and the free amines derivatised using procedures (iv-a).

v). Cleavage of the Peptide from the Resin to Give Methyl Ester:

The resin was treated with anhydrous methanol (2.5 ml/100 mg of resin), anhydrous DMF (2.5 ml/100 mg of resin) and anhydrous DIPEA (0.5 ml/100 mg of resin) and heated in an oil bath at 50° C. overnight. The resin was drained and washed with DMF (×3) and MeOH (×3) and solvents removed under reduced pressure.

vi). Cleavage of the Peptide from the Resin to Give Methylamide:

The resin was washed with THF (×3) and then DIPEA (×2) and then treated with Methylamine 2M in THF, 2 ml/100 mg of resin) and shaken at room temperature overnight. The resin was drained by using reduced pressure and then washed with THF (×2), DCM (×2) and ACN (×2). The solvents were blown off using N$_2$ gas and a sample was analysed by LCMS for quality control.

vii). Deprotection of the ivDde Protecting Group:

Peptides (40 mg) were dissolved in a solution of 2% hydrazine hydrate in DMF (2.0 ml). The resulting solution was stirred at room temperature for 30 min and the solvent was removed under reduced pressure. Some samples were analysed by LCMS for quality control.

viii). Solution Phase Coupling with Vancomycin:

A solution of peptide 7 (50 µmol) in dry DMF (0.86 ml) was treated with a solution of vancomycin hydrochloride (89 mg, FW 1485.71, 59.9 µmol, 1.2 equiv.) in dry DMF (0.86 ml) To this solution was added a solution of HBTU in dry DMF (120 µl, 0.5 M, 60 µmol), 1.2 eq) followed by DIPEA (36 µl, d 0.742, FW 129.25, 0.207 µmol, 4.1 equiv.). The resulting solution was stirred at room temperature overnight. A sample was analysed by LCMS to ensure completion of coupling, and additional coupling reagent added if needed. The solvent was removed in vacuo.

ix). 4-Methyltrityl Group Deprotection:

The vancomycin coupled compounds (50 mg) were treated with a solution of 2% TFA and 5% TES in DCM (2 ml) and allowed to stand for 30 min. The solvents removed under reduced pressure, and a sample was analysed by LCMS to ensure complete deprotection. The process was repeated if needed. The final compounds were dissolved in H2O/ACN (1:1, 1.0 ml), filtered through a 0.45 µm syringe filter and analysed by LCMS.

x). Cleavage of Methyl Ester:

In order to obtain the compounds having carboxylic acid at the C-terminus, the compounds were treated with dioxane/water (1:1), and an aqueous solution of LiOH (10 eq) 0.1 ml, 0.5 M, 50 µmol) and stirred at room temperature for overnight. The samples were freeze dried and dissolved in H2O/ACN (1:1, 1.0 ml), filtered through a 0.45 µm syringe filter and analysed by LCMS.

Final purification by HPLC: The crude products were dissolved in water/acetonitrile (1:1 by volume), filtered and purified by preparative HPLC using a gradient elution of water/acetonitrile with 0.1% TFA (Agilent Zorbax SB-Phenyl, 9.4×250 mm, 5 µm particle size, flow rate 5 mL min-1, 0 to 100% CH3CN+0.1% TFA in H2O+0.1% TFA over 15 minutes (acid derivatives) or Agilent Zorbax SB-C18, 9.4× 100 mm, 5 µm particle size, flow rate 5 mL min-1, 0 to 100% CH3CN+0.1% TFA in $H_2O$+0.1% TFA over 30 minutes (amide derivatives)). Fractions analysed by LCMS with >95% purity by ELSD were polled and lyophilised. (Analytical HPLC given below for Agilent Eclipse XDB-Phenyl, 4.6×150 mm, 5 µm particle size, flow rate 0.5 mL min-1, 0 to 100% CH3CN+0.05% FA in H2O+0.05% FA over 13 minutes).

The identities of the compounds were confirmed using high resolution mass spectroscopy (HRMS) and MS-MS analysis.

Example 2. Synthesis of MCC000310: Solid Phase Synthesis with Solution Phase Glycopeptide Coupling The standard procedures described in Example 1 were applied to the synthesis of MCC000310.

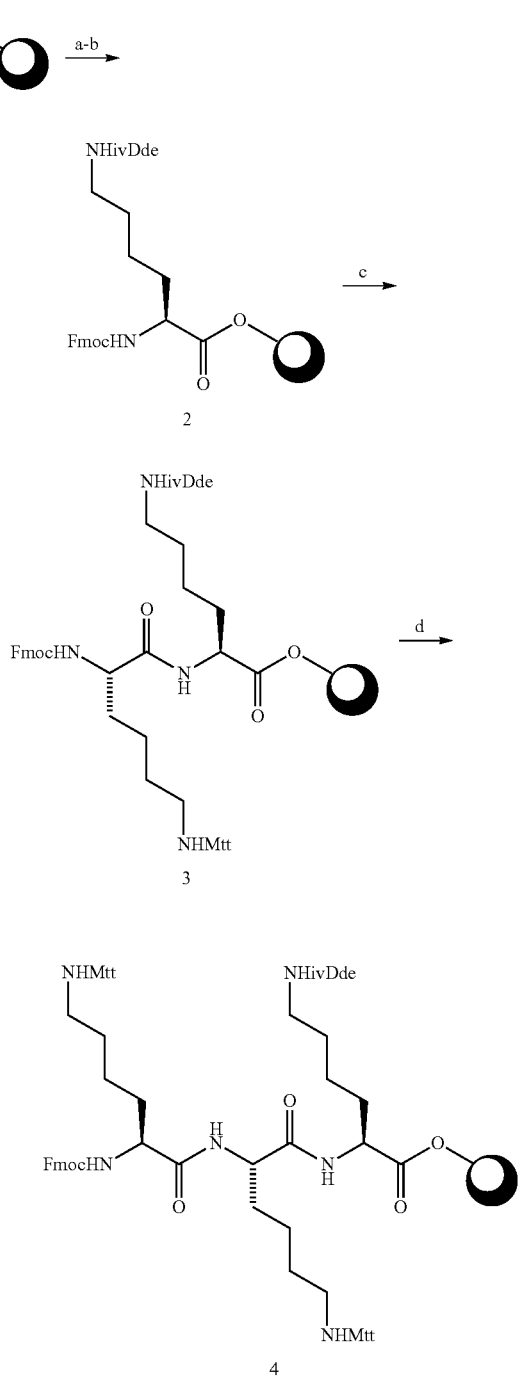

Scheme 1

Reagents and Conditions: a) Fmoc-L-Lys(ivDde)-OH, DIC, HOBt, DMAP, DMF, RT, 16 h; b) acetic anhydride, DIPEA, DMF, RT, 16 h; c) 20% piperidine in DMF, RT, 2 x 30 min, Fmoc-Lys(Mtt)-OH, HBTU, DIPEA, DMF, RT, 3 h; d) 20% piperidine in DMF, RT, 2 x 30 min, Fmoc-Lys(Mtt)-OH, HBTU, DIPEA, DMF, RT, 3 h.

Scheme 2
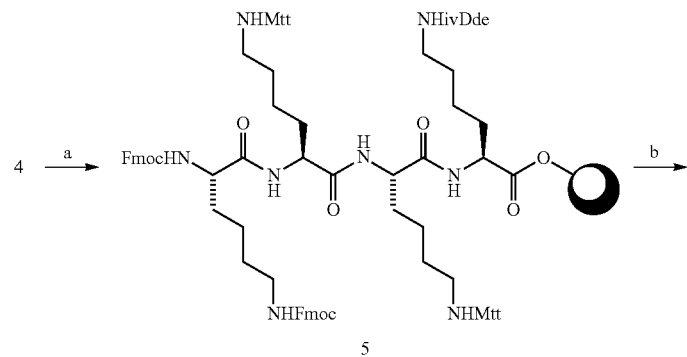
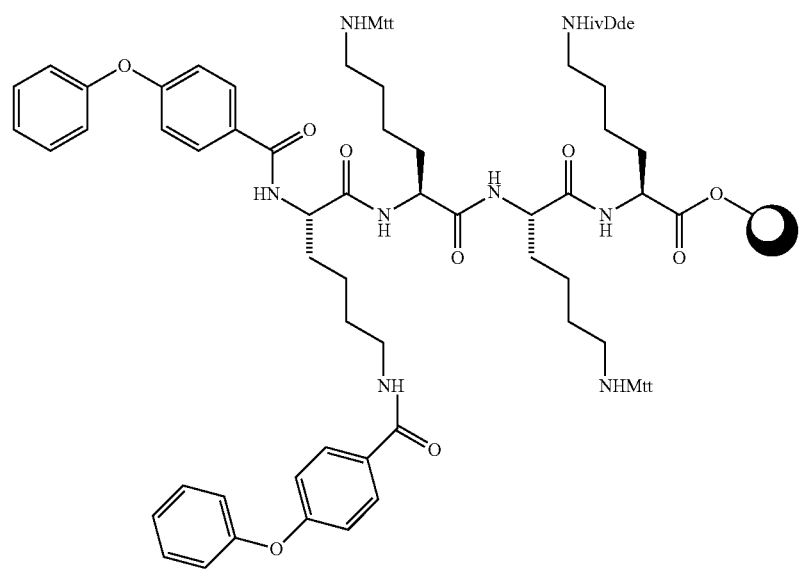
Reagents and Conditions: a) 20% piperidine in DMF, RT, 2 x 30 min, Fmoc-Lys (Fmoc)-OH, HBTU, DIPEA, DMF, RT, 16 h; b) 20% piperidine in DMF, RT, 2 x 30 min, 4-phenoxybenzoic acid, HBTU, DIPEA, DMF, RT, 16 h.

Scheme 3
6 →ᵃ
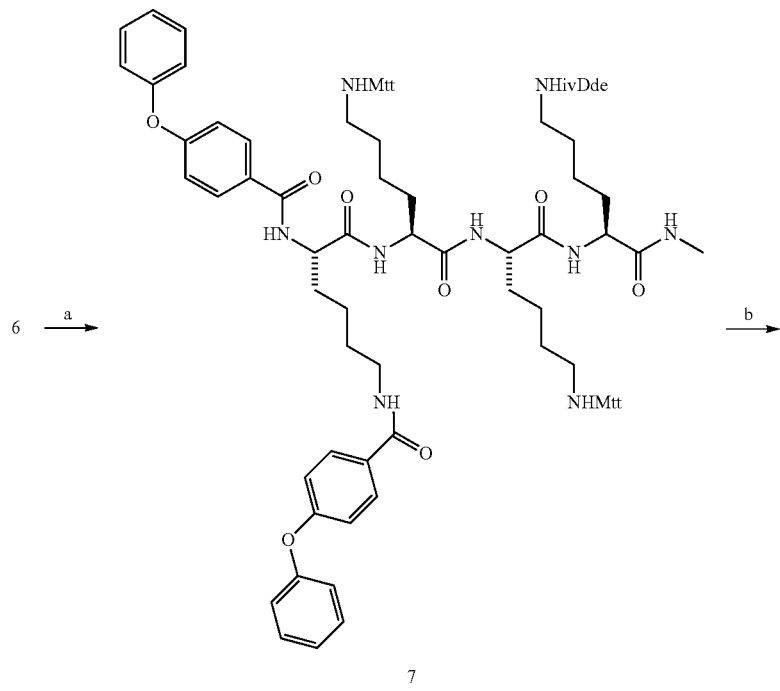
7
→ᵇ
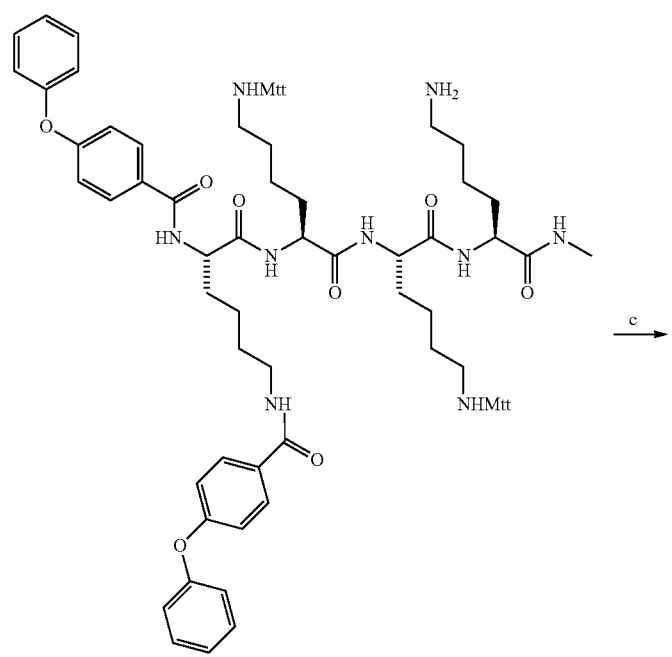
8
→ᶜ

-continued
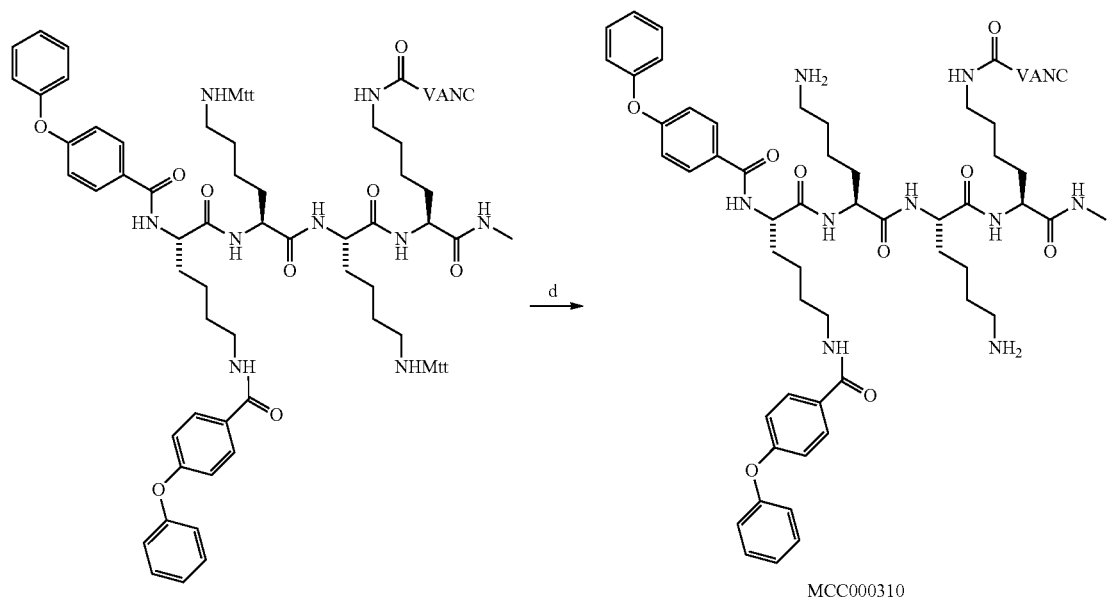
9 → d → MCC000310
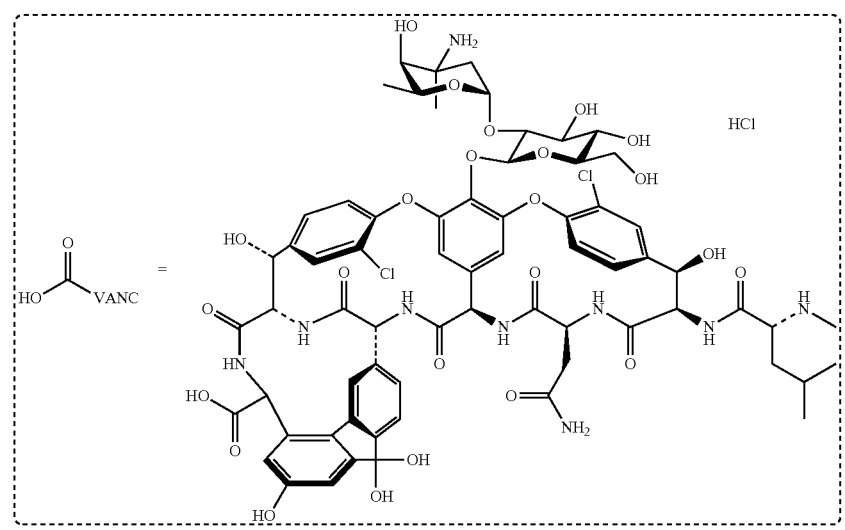
Reagents and Conditions: a) 2M NH₂Me in THF, RT, 16 h; b) 2% hydrazine in DMF, RT, 1 h; c) vancomycin•HCl, HBTU, DIPEA, DMF, RT, 16 h; d) 2% TFA, 5% TES in DCM, RT, 3 x 1 h.

Example 3. Synthesis of MCC000635: Solid Phase Synthesis with Solution Phase Glycopeptide Coupling For the preparation of MCC000635, the common intermediate tripeptide 4 from Example 2 was treated with Fmoc-L-Lys(Mtt)-OH under standard conditions to give peptide 10. Peptide 10 was treated with myristic acid to give the alkyl tail peptide 11, which was cleaved from the resin for subsequent solution-phase coupling with vancomycin.

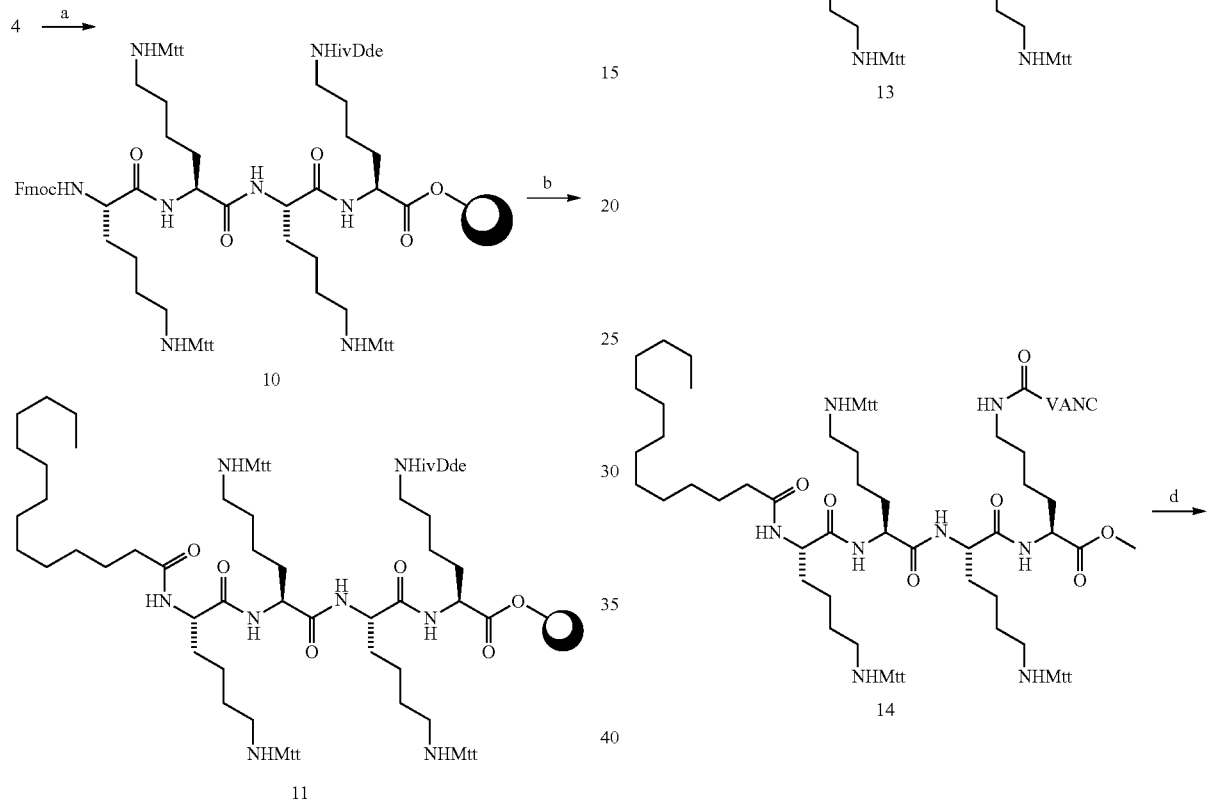

Reagents and Conditions: a) 20% piperidine in DMF, RT, 2 x 30 min, Fmoc-Lys(Mtt)-OH, HBTU, DIPEA, DMF, RT, 16 h; b) 20% piperidine in DMF, RT, 2 x 30 min, myristic acid, HBTU, DIPEA, DMF, RT, 16 h.

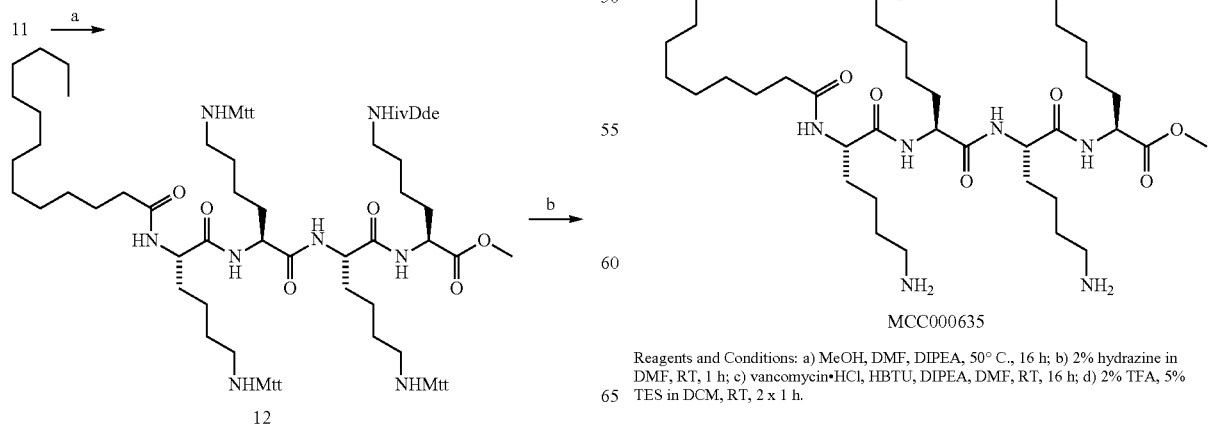

Reagents and Conditions: a) MeOH, DMF, DIPEA, 50° C., 16 h; b) 2% hydrazine in DMF, RT, 1 h; c) vancomycin•HCl, HBTU, DIPEA, DMF, RT, 16 h; d) 2% TFA, 5% TES in DCM, RT, 2 x 1 h.

Example 4. Synthesis of MCC000223: Conversion of MCC000635

The purified methyl ester MCC000635 (20 mg) was treated with an excess of LiOH (10 equiv) in dioxane:H2O (50:50) (Scheme 6) and the progress of the reaction was monitored using LCMS. The ester was cleanly hydrolysed in dilute conditions at 5° C. over a 24 h period to furnish MCC000223. HPLC purification generated MCC223 in good yield (10 mg).

Scheme 6

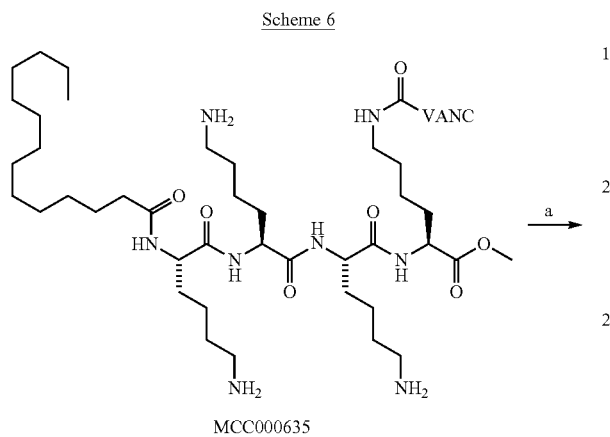

MCC000635

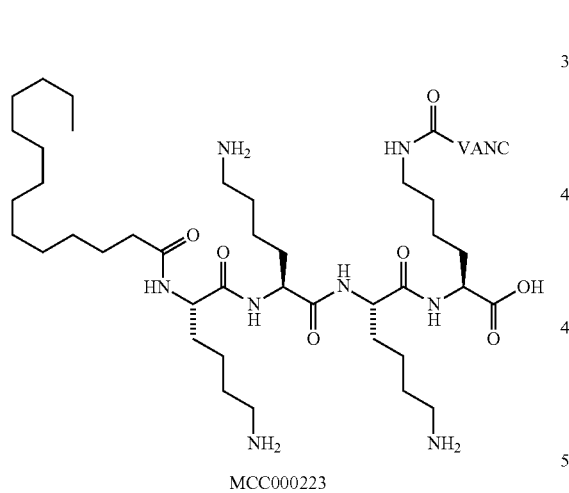

MCC000223

Reagents and Conditions: a) LiOH, Dioxane:H2O (50:50).

Example 5. Synthesis of MCC000223: Solid Phase Synthesis with Solid Phase Glycopeptide Coupling The solid phase route to prepare MCC223 utilised a HMPB resin (Scheme 6). The acid sensitive resin is attractive to use as the final step simultaneously removes the Mtt groups and cleaves the final product from the resin. An Alloc protecting group is utilised in place of the ivDde group. The solid phase route gave MCC223 in eight steps with a respectable overall yield of 11% (>95% purity) following HPLC purification.

Scheme 7

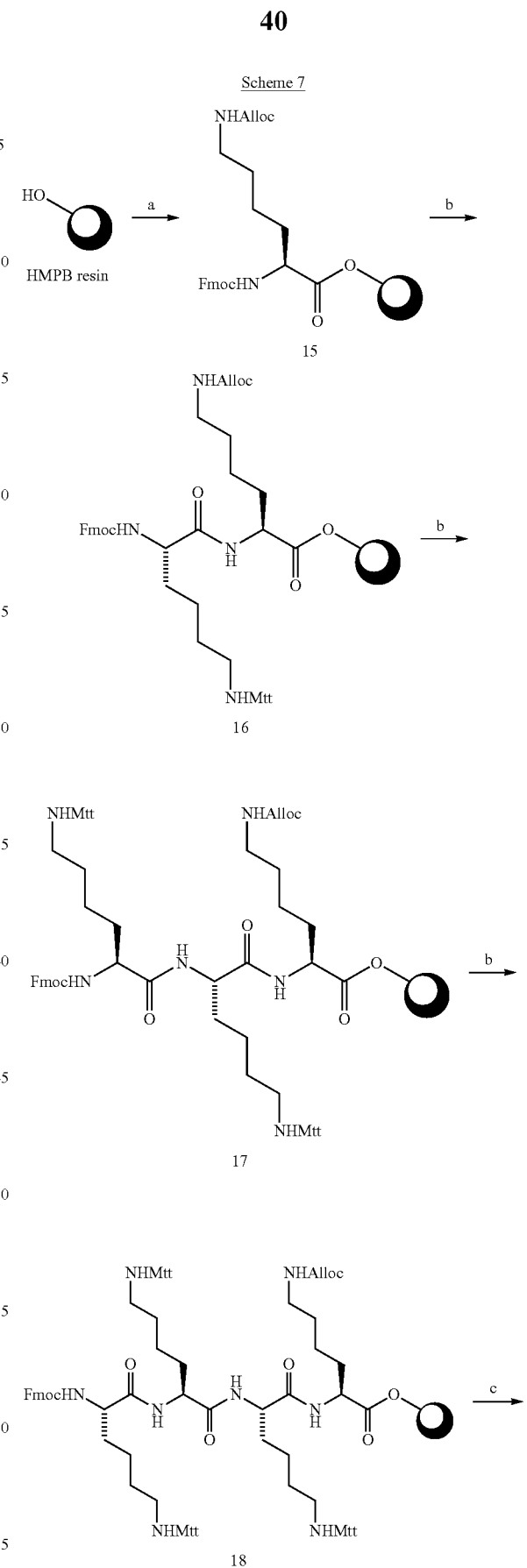

-continued

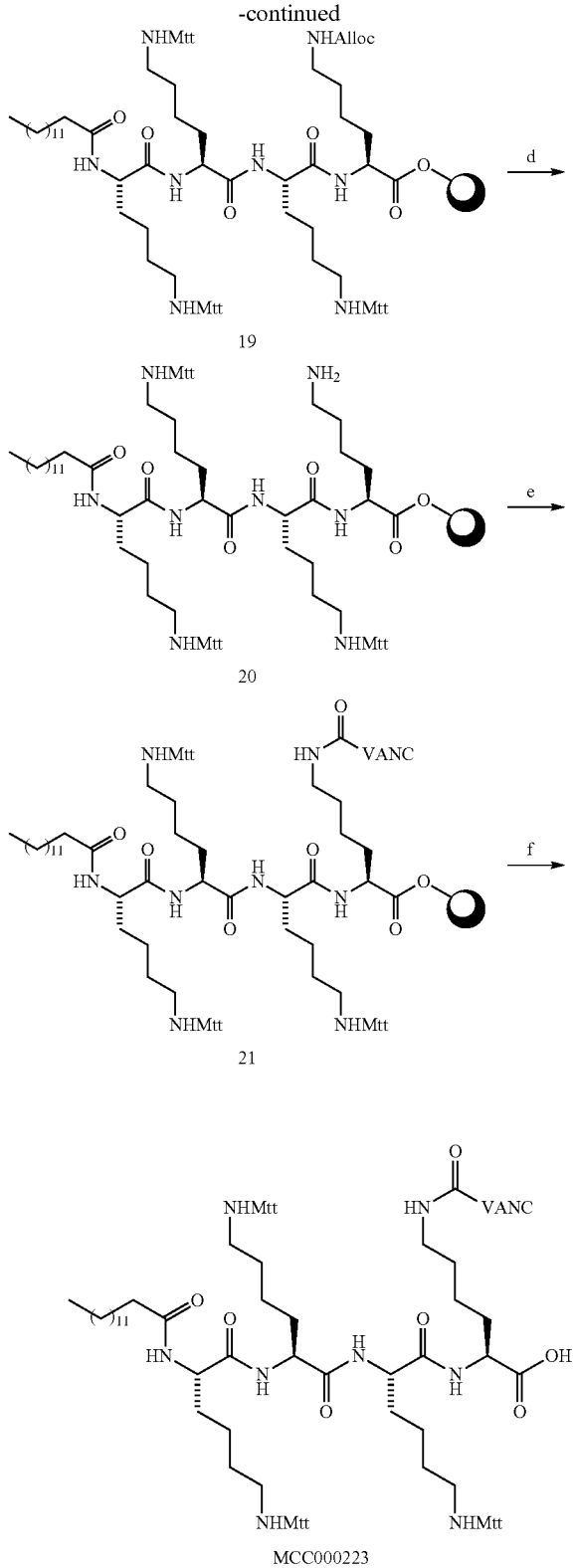

MCC000223

Reagents and Conditions: a) Fmoc-L-Lys (Alloc)-OH, DIC, HOBt, DMAP, DMF, RT, 16 h; rinse then acetic anhydride, DIPEA, DMF, RT, 1 h; b) 20% piperidine in DMF, RT, 30 min, rinse then Fmoc-Lys (Mtt)-OH, HBTU, DIPEA, DMF, RT, 1 h for 3 cycles; c) 20% piperidine in DMF, RT, 2 x 30 min, rinse, then myristic acid, HBTU, DIPEA, DMF, RT, 1 h; d) Pd(PPh$_3$)$_4$, phenylsilane, DCM, 20 h; e) vancomycin, HBTU, DIPEA, DMF, 18 h; f) 2% TFA 5% TES in DCM, 30 min.

Example 6. Synthesis of MCC000455: Solid Phase Synthesis with Solution Phase Glycopeptide Coupling to Produce a Compound with a Lys-NH$_2$ Linker Scheme 8

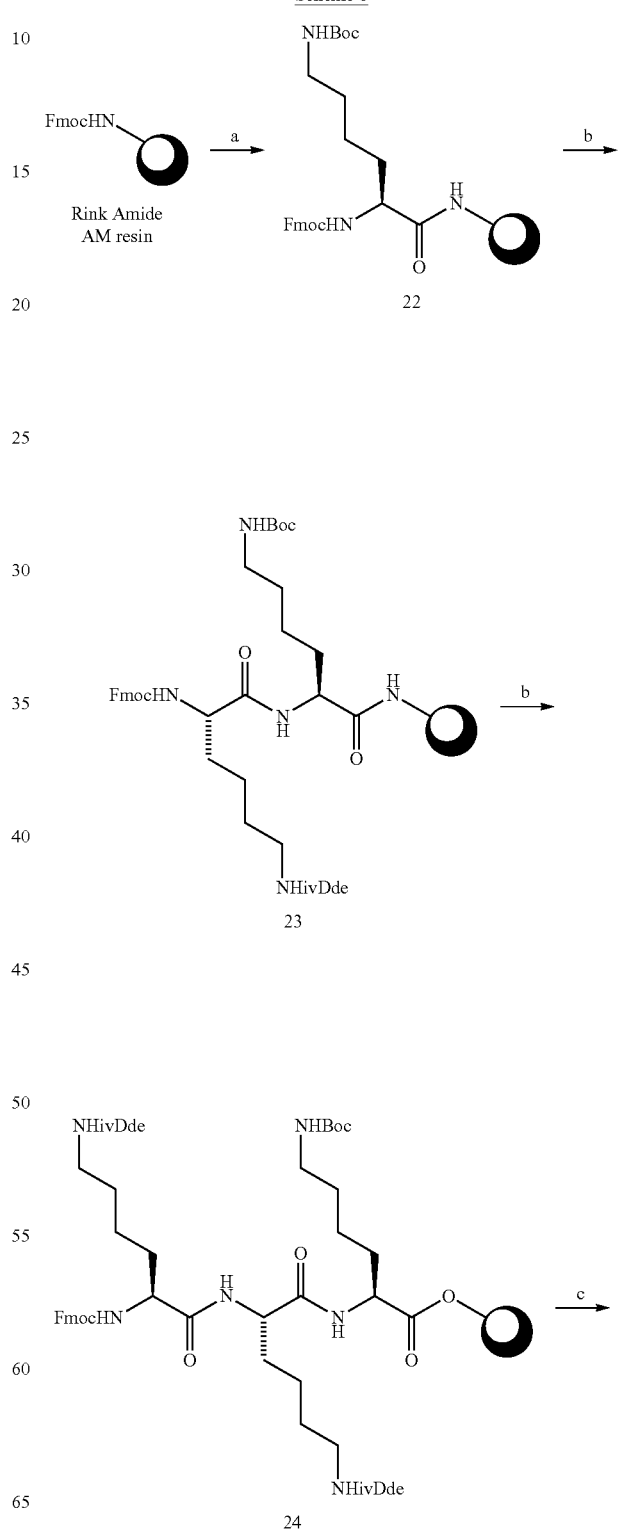

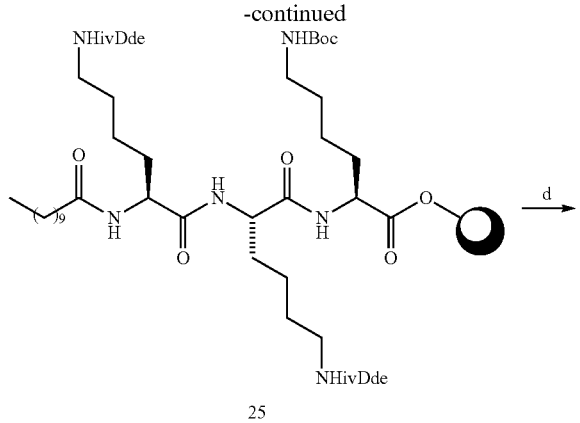

25

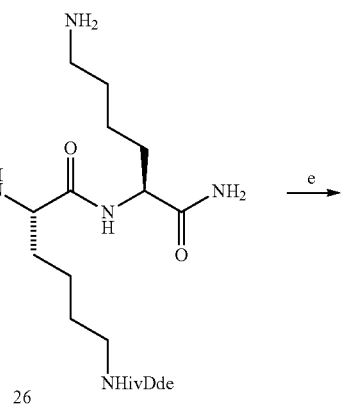

26

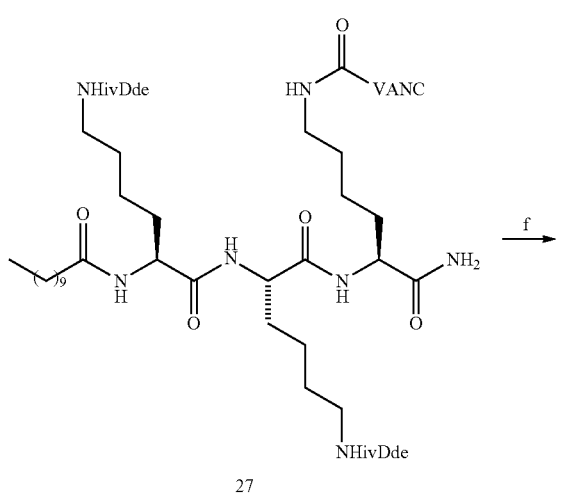

27

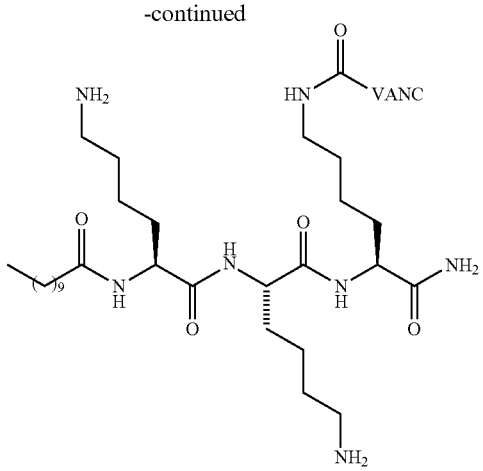

MCC000455

Reagents and Conditions: a) 20% piperidine in DMF, RT, 30 min, rinse, then Fmoc-L-Lys(Boc)-OH, HBTU, DIPEA, DMF, RT; b) 20% piperidine in DMF, RT, 30 min, rinse then Fmoc-Lys(ivDde)-OH, HBTU, DIPEA, DMF, RT; c) 20% piperidine in DMF, RT, 2 x 30 min, rinse, then undecanoic acid, HBTU, DIPEA, DMF, RT, 1 h; d) 20% TFA, 5% TES, DCM; e) vancomycin, PyBOP/HBTU, DIPEA, DMF/DMSO; f) 2% hydrazine in DCM.

Fmoc Deprotection of Rink Amide AM Resin:

Rink amide AM resin (loading 0.94 mmol/g, 300 mg) was treated with 20% piperidine in DMF (6.0 ml) and shaken at room temperature for 30 minutes to remove the Fmoc protecting group. The resin was drained and washed with DMF (×3), MeOH (×3), and DCM (×3).

Loading of Rink Amide AM Resin with Fmoc-L-Lys(Boc)-OH:

Fmoc-L-Lys(Boc)-OH (703 mg) was dissolved in DMF (3.0 ml, 0.5 M). A solution of HBTU in DMF (3.0 ml, 0.5 M) was added followed by DIPEA (523 µl). The solution was stood at room temperature for 10 minutes then added to the resin which had been washed previously three times with DMF. The resin was then shaken at room temperature for 1 hour, drained and washed with DMF (×3), MeOH (×3) and DCM (×3).

Fmoc Deprotection:

The resin was treated with 20% piperidine in DMF (6.0 ml) and shaken at room temperature for 30 minutes. The resin was drained and washed with DMF (×3), MeOH (×3), and DCM (×3).

Peptide Coupling with Fmoc-L-Lys(ivDde)-OH:

A solution of Fmoc-L-Lys(ivDde)-OH (423 mg) in DMF (4.5 ml, 0.167 M) was prepared. To this, a solution of HBTU in DMF (1.5 ml, 0.5 M) was added followed by DIPEA (261 µl). The solution was stood at room temperature for 10 minutes then added to the resin which had been washed previously three times with DMF. The resin was then shaken at room temperature for 2 hours, drained and washed with DMF (×3), MeOH (×3) and DCM (×3). This step was repeated.

The Fmoc deprotection and coupling with Fmoc-L-Lys(ivDde)-OH steps were repeated, followed by another Fmoc deprotection.

Coupling with Undecanoic Acid:

A solution of undecanoic acid (279 mg) in DMF (3.0 ml) was mixed with a solution of HBTU in DMF (3.0 ml, 0.5 M) and DIPEA (523 µl). The solution was stood at room temperature for 10 minutes then added to the resin previously washed three times with DMF. The resin was shaken at room temperature for 1 hour, drained and washed with DMF (×3), MeOH (×3) and DCM (×3). The resin was dried in vacuo. 5 mg of resin was cleaved to check the extent of the reaction. The resin was dissolved in 1.0 ml acetonitrile, filtered through a 0.45 μm syringe filter and analysed by LCMS. LCMS analysis: RT 9.088 min, 80% by ELSD, (M+H)+ 982.5, (M+2+)2+ 491.9, (M+3H)3+ 328.3.

Cleavage of Rink Amide AM Resin and Boc Deprotection:

A solution of 20% TFA, 5% triethylsilane in DCM (6.0 ml) was prepared and added to the resin (300 mg) for 30 minutes. The resin was removed by filtration and washed with DCM (×3) and acetonitrile (×3). The solvent was removed in vacuo. The resin was dissolved in 1:1 ACN/H2O and freeze-dried.

Solution Phase Coupling with Vancomycin:

In a glove box, the peptide (40 mg, 40.7 μmol) was dissolved in dry DMF (0.7 ml, 58.1 mM). Vancomycin.HCl (72 mg, FW1485.71, 48.8 μmol, 1.2 eq) in dry DMSO (0.7 ml, 69.7 mM) was heated until dissolved and the solution was clear. The solution was cooled to room temperature and added to the peptide. A 98 μl solution of HBTU (95 mg, FW 379.3) in dry DMF (0.5 ml, 0.5 M) solution followed by DIPEA (29 μl, 4.1 eq) was added and stirred overnight. LCMS analysis: Rt 7.189 min, 25% by ELSD, (M+2H)2+ 1207.4, (M+3H)3+ 805.3, (M+4H)4+ 604.4.

ivDde Deprotection:

The vancomycin derivative was treated with 1.0 ml of 2% hydrazine monohydrate in 1:1 DMF/DMSO and stirred at room temperature overnight. The extent of the reaction was checked by dissolving 20 μl of the solution in 0.8 ml 1:1 ACN/H$_2$O and analysing by LCMS after 30 minutes, 2 hours, and overnight. LCMS analysis: desired product Rt 5.388 min, 50% by ELSD, (M+2H)2+ 1000, (M+3H)3+ 667.8, (M+4H)4+ 501; only one ivDde removed Rt 6.376 min, 20% by ELSD, (M+2H)2+ 1103, (M+3H)3+ 736.5, (M+4H)4+ 552.6. The solvent was then removed under high vacuum at 35° C. overnight.

Purification of Final Product:

The crude product was dissolved in water/ACN and purified using a Shimadzu preparative HPLC. The purified product was lyophilised to give a white powder, 19 mg, 19% based on amount of cleaved peptide.

Example 7. General Procedure to Produce a Compound with a Non-Branched Diamine Linker: Solid Phase Synthesis with Solution Phase Glycopeptide Coupling Scheme 9

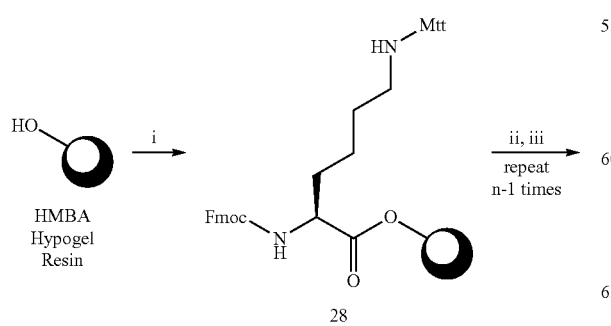

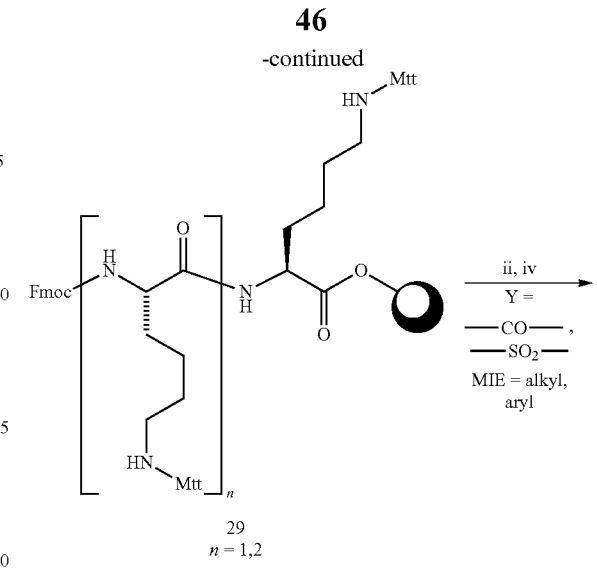

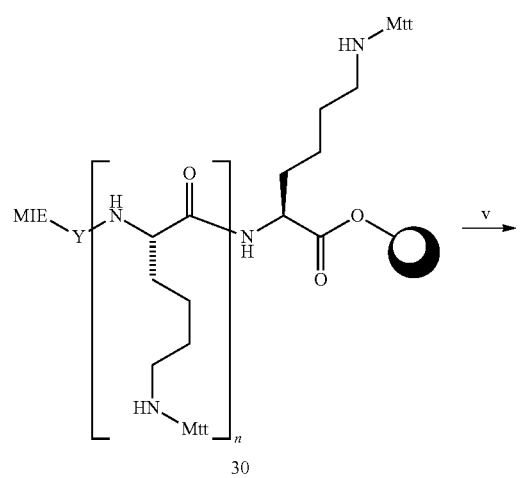

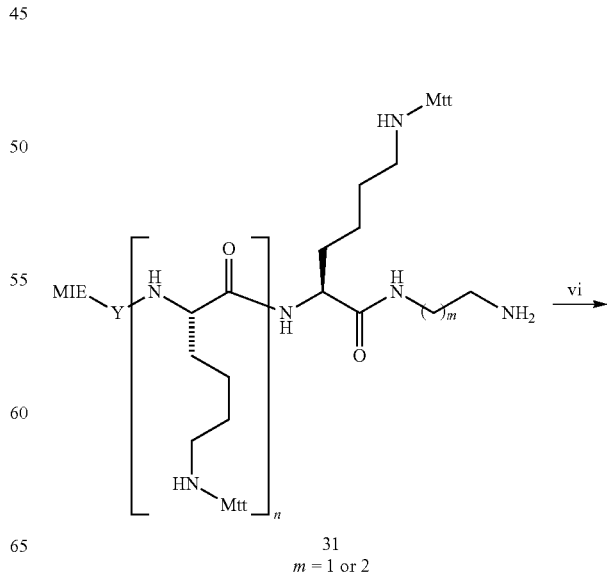

47

-continued

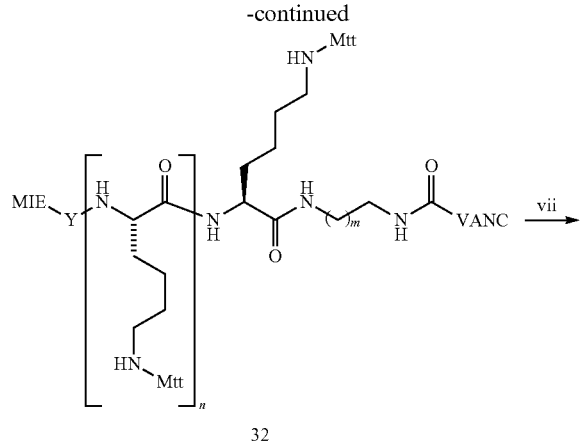

32

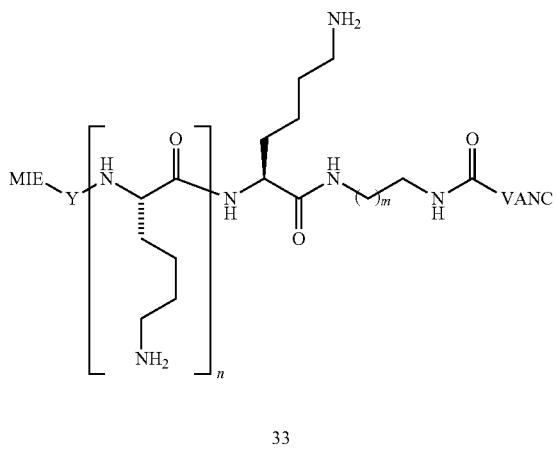

33

Reagents and Conditions: i) Fmoc-L-Lys(Mtt)-OH, DIC, HOBt, DMAP, DCM, DMF; ii) 20% piperidine in DMF, RT, 30 min; iii) Fmoc-L-Lys(Mtt)-OH, HBTU, DIPEA, DMF, RT; iv) RCOOH, HBTU, DIPEA, DMF or RSO$_2$Cl, DIEA; v) NH$_2$(CH$_2$)$_m$NH$_2$, DIPEA, DMF, 50° C.; vi) vancomycin, HBTU, DIPEA, DMF/DMSO; vii) 2% TFA, 5% TES, DCM General Procedure for 1,3-Diaminopropane and 1,2-Diaminoethane Mediated Cleavage from Hypogel HMBA Resin:

A solution of 1,3-diaminopropane or 1,2-diaminoethane in DMF (2.0 M, 2.0 ml per 100 mg of resin) was added to the resin in a glass vial. The vial was well sealed and heated at 50° C. overnight. The resin and solution were transferred into a solid phase reaction tube. The filtrate was collected and the resin was washed with DMF (×3), methanol (×3) and acetonitrile (×3). The washings were combined with the filtrate and the solvent was removed under reduced pressure to give the crude lipopeptide as the C-terminal aminoalkylamide. The crude lipopeptide was used for the solution phase coupling reaction with vancomycin without further purification.

48

Example 8. Synthesis of MCC000344: Solid Phase Synthesis with Solution Phase Glycopeptide Coupling

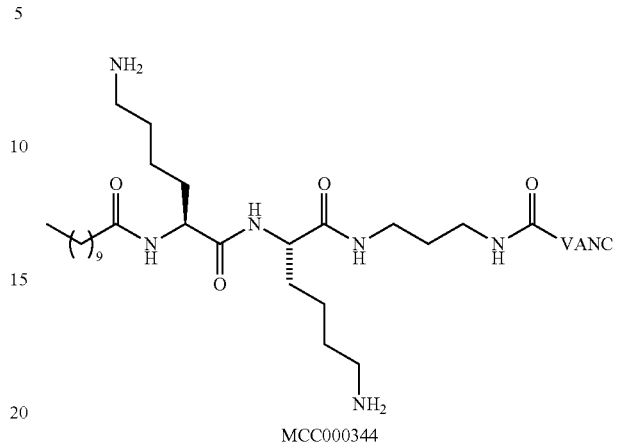

MCC000344

Loading of Fmoc-L-Lys(Mtt)-OH onto Hypogel HMBA Resin:

1.5 g of HMBA Hypogel resin (Loading: 0.81 mmol/g) was washed with DMF (3×). A solution of Fmoc-L-Lys(Mtt)-OH (3.8 g, MW 624.8 g/mol, 5 eq) was prepared in 15 mL of DMF. Hydroxybenzotriazole (HOBt) (0.82 g, MW 135, 5 eq), N,N-diisopropylcarbodiimide (DIC) (941 μL, MW 126.2 g/mol, 5 eq) and 4-dimethylaminopyridine (DMAP) (44.5 mg, MW 122.17) were added into the amino acid solution. The solution was added to the prewashed resin and shaken overnight at room temperature. The resin was drained, washed with DMF (3×), MeOH (3×) and DCM (3×) and dried in vacuo.

Deprotection of Fmoc Protecting Group:

250 mg of resin was prewashed with DMF (3×), treated with 2.5 mL of 20% piperidine in DMF (1.0 mL per 100 mg of resin) and shaken at room temperature for an hour. The resin was drained, washed with DMF (3×), MeOH (3×) and DCM (3×) and dried in vacuo.

Amino Acid Coupling to Resin-Bound Peptide:

A solution of Fmoc-L-Lys(Mtt)-OH (1539 mg, MW 624.8 g/mol, 2 eq) in 14.75 mL of DMF was prepared. A solution of HBTU in dry DMF (0.5 M, 4.92 mL) and DIPEA (1713 μL, MW 129.25) was added into the amino acid solution. The solution was left to stand at room temperature for 10 minutes then added to the prewashed resin and shaken overnight at room temperature. The resin was drained, washed with DMF (3×), MeOH (3×) and DCM (3×) and dried in vacuo.

Deprotection of Fmoc Protecting Group:

250 mg of resin was prewashed with DMF (3×), treated with 2.5 mL of 20% piperidine in DMF (1.0 mL per 100 mg of resin) and shaken at room temperature for an hour. The resin was drained, washed with DMF (3×), MeOH (3×) and DCM (3×) and dried in vacuo.

Coupling of Insertive Element to Resin-Bound Peptide:

Solutions of undecanoic acid (105 mg, MW 186.29 g/mol 5.1 eq) in 1.13 mL of DMF and HBTU in dry DMF (1.13 mL, 0.5 M, 5.1 eq) were prepared. The HBTU solution was added to the undecanoic acid solution followed by addition of DIPEA (196 μL, MW 129.25 g/mol, d 0.742, 10.2 eq). The solution was left to stand at room temperature for 10 minutes then added to prewashed resin (225 mg) and shaken at room temperature overnight. The resin was drained, washed with DMF (3×), MeOH (3×) and DCM (3×) and dried in vacuo.

Resin Cleavage Using 1,3-Diaminopropane:

25 mg of resin was treated with 0.75 mL of 1,3-diaminopropane and 0.15 mL of DIPEA. The reaction mixture was left to stir overnight at room temperature. The cleaved peptide was collected, along with resin washings using DCM (3×), MeOH (3×) and ACN (3×). The solvents were evaporated and dried in vacuo.

Solution Phase Coupling of Peptide and Vancomycin:

A solution of vancomycin.HCl (195.76 mg, MW 1485.7 g/mol, 0.125 M, 1.2 eq) was prepared in 1.05 mL of dry DMSO. Mild heating is required to fully dissolve vancomycin. The observed colour changed from pink to light brown. HBTU in dry DMF (0.26 mL, MW 379.3 g/mol, 0.5 M 1.2 eq) was added to the vancomycin solution followed by DIPEA (78.42 µL, MW 129.25 g/mol, 4.1 eq). The solution was added to peptide and left to stir at room temperature overnight. The vancomycin derivative was evaporated to dryness under high-vac.

Deprotection of Mtt Protecting Group 20 mL of 2% TFA, 5% triethylsilane in dry DCM solution was added to Vancomycin derivative (200 mg). The solution was left to stir at room temperature for 30 min. Solvents were evaporated and dried in vacuo, with the final product MCC000344 purified by preparative HPLC.

Example 9. Synthesis of a Compound with a Triazole Linker: Solid Phase Synthesis with Solution Phase Glycopeptide Coupling to Produce MCC000453

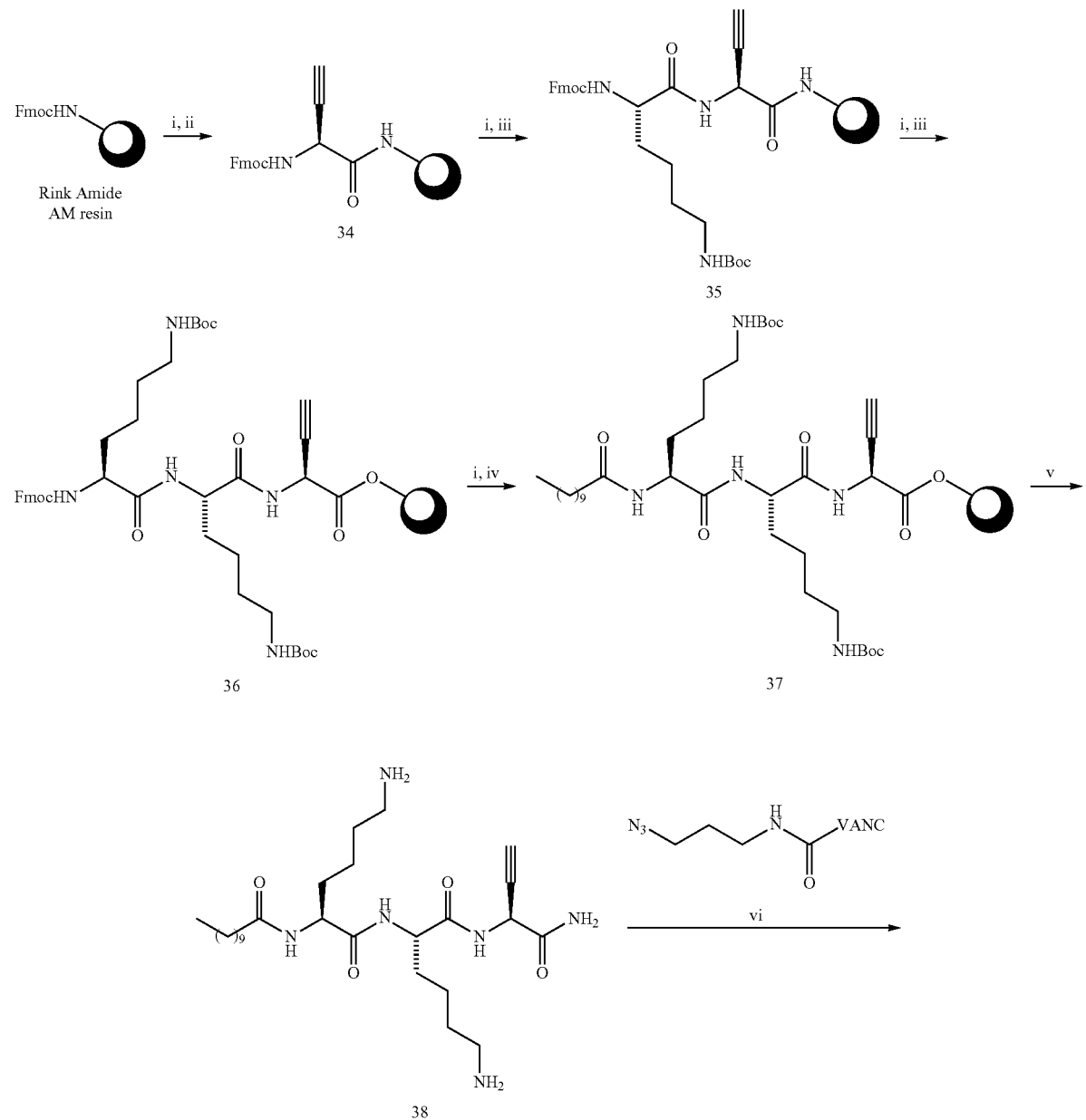

-continued

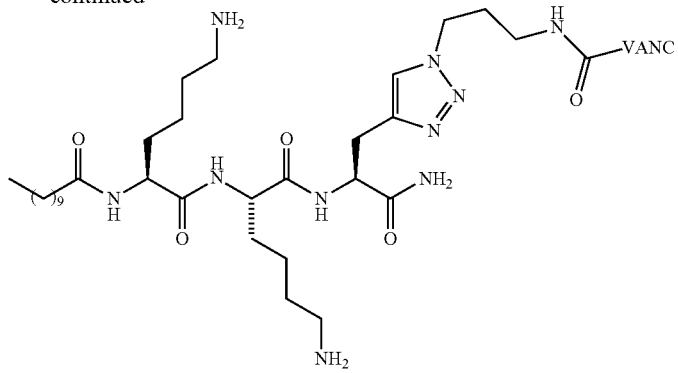

MCC000453

Reagents and Conditions: i) 20% piperidine in DMF, RT; ii) Fmoc-L-propargylglycine-OH, HBTU, DIPEA, DMF, RT; iii) Fmoc-L-Lys(Boc)-OH, HBTU, DIPEA, DMF, RT; iv) undecanoic acid, HBTU, DIPEA, DMF, RT; v) 20% TFA, 5% TES, DCM; vi) CuSO$_4$, NaAsc, DMF, H$_2$O.

Fmoc Deprotection of Rink Amide AM Resin:

Rink amide AM resin (loading 0.81 mmol/g, 300 mg) was treated with 20% piperidine in DMF (6.0 ml) and shaken at room temperature for 30 minutes to remove the Fmoc protecting group. The resin was drained and washed with DMF (×3), MeOH (×3), and DCM (×3).

Loading of Rink Amide AM Resin with Fmoc-L-Propargylglycine:

Fmoc-L-Propargylglycine was dissolved in DMF (4.5 ml, 0.5 M). A solution of HBTU in DMF (1.5 ml, 0.5 M) was added followed by DIPEA (0.5 M final concentration). The solution was stood at room temperature for 10 minutes then added to the resin which had been washed previously three times with DMF. The resin was then shaken at room temperature for overnight, drained and washed with DMF (×3), MeOH (×3) and DCM (×3).

Fmoc Deprotection:

The resin was treated with 20% piperidine in DMF (6.0 ml) and shaken at room temperature for 30 minutes. The resin was drained and washed with DMF (×3), MeOH (×3), and DCM (×3).

Peptide Coupling with Fmoc-L-Lys(Boc)-OH:

A solution of Fmoc-L-Lys(Boc)-OH (703 mg) in DMF (3.0 ml, 0.5 M) was prepared. To this, a solution of HBTU in DMF (3.0 ml, 0.5 M) was added followed by DIPEA (523 μl). The solution was stood at room temperature for 10 minutes then added to the resin which had been washed previously three times with DMF. The resin was then shaken at room temperature for 1 hour, drained and washed with DMF (×3), MeOH (×3) and DCM (×3).

Fmoc Deprotection:

The resin was treated with 20% piperidine in DMF (6.0 ml) and shaken at room temperature for 30 minutes. The resin was drained and washed with DMF (×3), MeOH (×3), and DCM (×3).

Coupling with Undecanoic Acid:

A solution of undecanoic acid (279 mg) in DMF (3.0 ml) was mixed with a solution of HBTU in DMF (3.0 ml, 0.5 M) and DIPEA (523 μl). The solution was stood at room temperature for 10 minutes then added to the resin previously washed three times with DMF. The resin was shaken at room temperature for 1 hour, drained and washed with DMF (×3), MeOH (×3) and DCM (×3). The resin was dried in vacuo.

Cleavage of Rink Amide AM Resin and Boc Deprotection:

A solution of 20% TFA, 5% triethylsilane in DCM (0.5 ml) was prepared and added to the resin to stand for 30 minutes. The resin was removed by filtration and washed with DCM (×3) and acetonitrile (×3). The solvent was removed in vacuo. The residue was dissolved in 1:1 ACN/H$_2$O and freeze-dried. 1 mg of the sample was dissolved in 1.0 ml acetonitrile, filtered through a 0.45 μm syringe filter and analysed by LCMS: -Rt 6.38 min, 90% by ELSD, (M+H)+ 537.3, (M+2H)2+ 269.2

Preparation of Azidoalkylamine Vancomycin:

Solution Phase Coupling of Vancomycin Azide Derivative ("Click" Reaction):

The vancomycin-azide analogue (1.5 mg, 1 μmol) was dissolved in H$_2$O. To this solution was added CuSO$_4$.5H$_2$O (0.5 mg, 2 μmol) and sodium ascorbate (1 mg, 5 μmol). The resulting solution was added to a solution of peptide (0.5 mg, 1 μmol) in DMF (250 μl), and then heated in the microwave at 80° C. for 10 minutes. 0.125 ml of the solution was mixed with 0.375 ml of 1:1 ACN/H$_2$O, filtered through a 0.45 μm syringe filter and analysed by LCMS: Rt 5.522 min, 70% by ELSD, (M+2H)2+ 1034.3, (M+3H)3+ 690, (M+4H)4+ 517.7. The crude product was dissolved in water/ACN and purified using a Shimadzu preparative HPLC, with lyopholisation producing a white powder, 1.3 mg, 16% based on amount of cleaved peptide. LCMS: Rt 5.57 95% (ELSD) [M+2H]2+ 1033.8, [M+3H]3+ 690.2, [M+4H]4+ 517.8.

Example 10. Summary of Synthesised Compounds

Compounds were synthesised by one of more of the routes described above, or variations thereof. A chemist with ordinary skill in the art of synthesis will recognise that variations in the procedures described will still produce the desired product, either by alteration in the reagents used (such as substitution of alternate coupling reagents for amide bond formation) or by varying the placement, type and order of removal of protecting groups, or by varying the order in which the components are assembled.

TABLE 1
Structures Corresponding to Element X Abbreviations
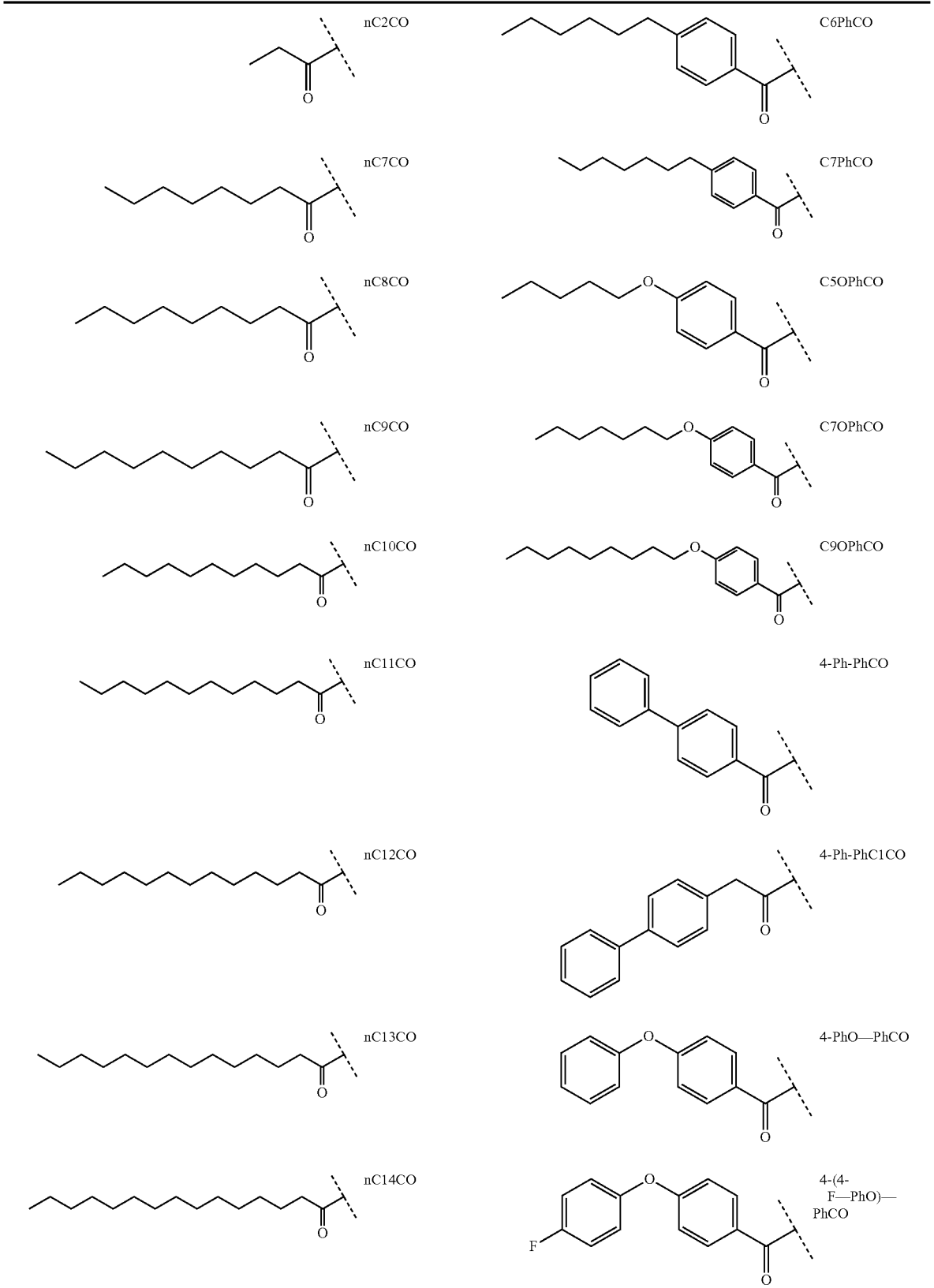

TABLE 1-continued
Structures Corresponding to Element X Abbreviations
| Structure | Abbreviation | Structure | Abbreviation |
|---|---|---|---|
| 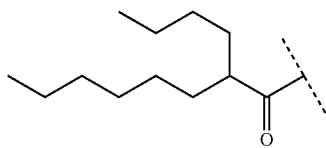 | 2-Bu-nC7CO | 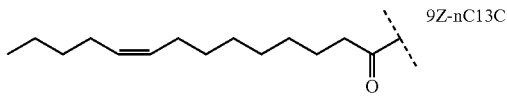 | 4-(4-Cl—PhO)—PhCO |
| 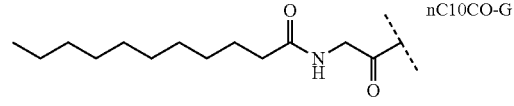 | 9Z-nC13CO | 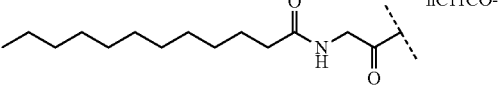 | 4-BnO—PhCO |
| 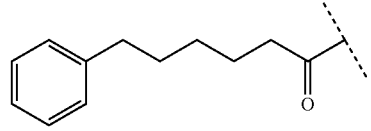 | nC10CO-G | 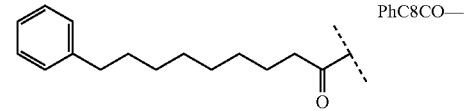 | (4-PhO—PhCO)-G |
| 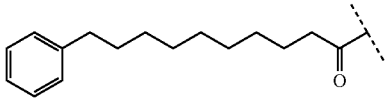 | nC11CO-G- | 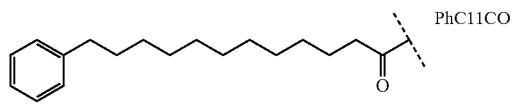 | PhOC3CO |
| 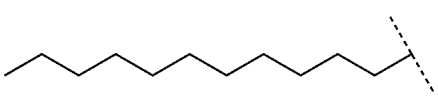 | PhC5CO | 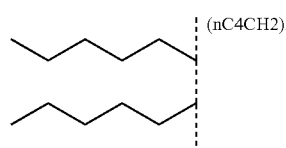 | 4-Me-PhSO2 |
| 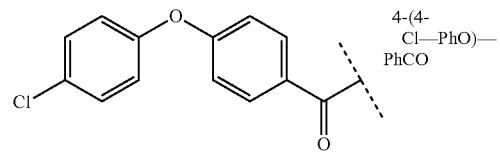 | PhC8CO— | 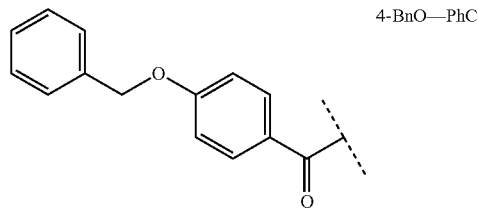 | 4-NH2-PhCO |
| 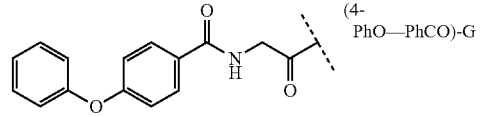 | PhC9CO | 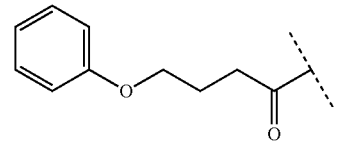 | 4-MeNH—PhCO |
| 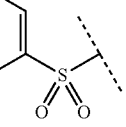 | PhC11CO | 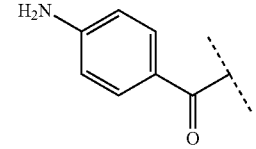 | 4-nC7NH—PhCO |
| 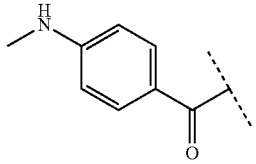 | nC10CH2 | 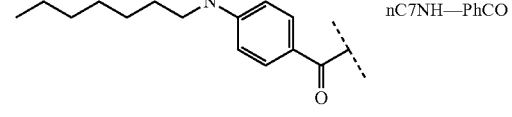 | 4-Cl—PhCO |
| 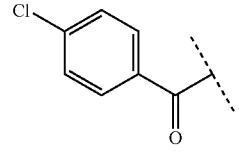 | (nC4CH2)2 | 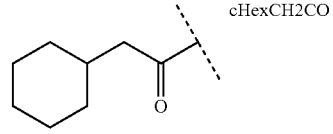 | cHexCH2CO |

TABLE 1-continued
Structures Corresponding to Element X Abbreviations
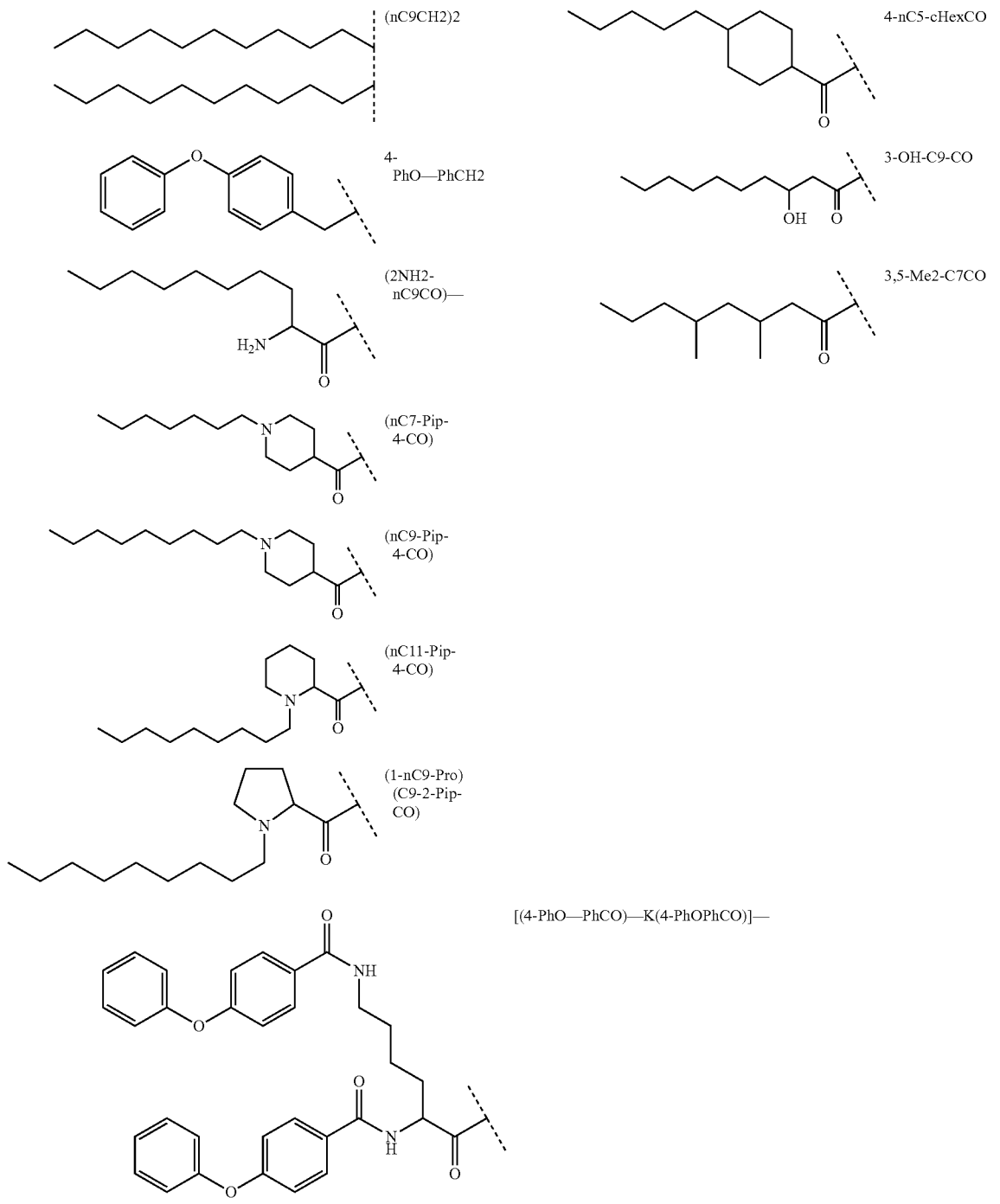
TABLE 2
Summary of Compound Structures
| Compound Number | X | W |
|---|---|---|
| MCC_000080 | nC$_{10}$CO— | —K— |
| MCC_000082 | nC$_{10}$CO— | —GSKKK— |

TABLE 2-continued

Summary of Compound Structures (SEQ ID NO: 1)

| | | |
|---|---|---|
| MCC_000173 | nC10CO— | —KK— |
| MCC_000174 | nC$_{10}$CO— | —KK— |
| MCC_000175 | nC$_{13}$CO— | —KK— |
| MCC_000194 | (4-PhO—PhCO)— | —KKK— |
| MCC_000214 | (4-PhO—PhCO)— | —KK— |
| MCC_000217 | [(4-PhO—PhCO)—K(4-PhO—PhCO)]— | —KK— |
| MCC_000223 | nC$_{13}$CO— | —KKK— |
| MCC_000224 | nC$_{13}$CO— | —KK— |
| MCC_000225 | nC$_{10}$CO— | —KK— |
| MCC_000226 | nC$_{13}$CO— | —KK— |
| MCC_000227 | nC$_{13}$CO— | —DLys-DLys— |
| MCC_000228 | nC$_{13}$CO— | —OO— |
| MCC_000229 | nC$_{10}$CO— | —KK— |
| MCC_000230 | [(4-PhO—PhCO)—K(4-PhO—PhCO)]— | —KKK— |
| MCC_000231 | (nC$_{10}$CO)—K(CO—nC$_{10}$)— | —KK— |
| MCC_000292 | nC$_{10}$CO— | —KK— |
| MCC_000309 | nC$_{10}$CO— | —KKK— |
| MCC_000310 | [(4-PhO—PhCO)—K(4-PhO—PhCO)]— | —KK— |
| MCC_000316 | [(4-PhO—PhCO)—K(4-PhO—PhCO)]— | —KKK— |
| MCC_000343 | nC$_{13}$CO— | —KKK— |
| MCC_000344 | nC$_{10}$CO— | —KK— |
| MCC_000345 | nC$_{13}$CO— | —KK— |
| MCC_000346 | nC$_{10}$CO-G— | —KKK— |
| MCC_000347 | nC$_{11}$CO— | —KK— |
| MCC_000348 | nC$_{11}$CO— | —KKK— |
| MCC_000349 | nC$_{12}$CO— | —KK— |
| MCC_000350 | nC$_{12}$CO— | —KKK— |
| MCC_000367 | nC$_{10}$CO— | —KKK— |
| MCC_000380 | nC$_{13}$CO— | —GSKKK— |
| MCC_000381 | (4-PhO—PhCO)—G— | —KK— |
| MCC_000453 | nC$_{10}$CO— | —KK— |
| MCC_000455 | nC$_{10}$CO— | —KK— |
| MCC_000489 | nC$_7$CO— | —KK— |
| MCC_000490 | [nC$_7$CO—K(nC$_7$CO)]— | —K— |
| MCC_000491 | nC$_8$CO— | —KK— |
| MCC_000492 | nC$_9$CO— | —KK— |
| MCC_000493 | nC$_{11}$CO— | —KK— |
| MCC_000494 | nC$_{12}$CO— | —KK— |
| MCC_000495 | nC$_{14}$CO— | —KK— |
| MCC_000496 | (2-Bu-nC$_7$CO)— | —KK— |
| MCC_000497 | [(2-Bu—nC$_7$CO)—K(2-Bu—nC$_7$CO)]— | —K— |
| MCC_000498 | (9Z-nC$_{13}$CO)— | —KK— |
| MCC_000499 | nC$_6$PhCO— | —KK— |
| MCC_000500 | nC$_7$PhCO— | —KK— |
| MCC_000501 | nC$_5$OPhCO— | —KK— |
| MCC_000502 | [nC$_5$OPhCO—K(nC$_5$OPhCO)]— | —K— |
| MCC_000503 | nC$_7$OPhCO— | —KK— |
| MCC_000504 | nC$_9$OPhCO— | —KK— |
| MCC_000505 | PhOC$_3$CO— | —KK— |
| MCC_000506 | [PhOC$_3$CO—K(PhOC$_3$CO]— | —K— |
| MCC_000507 | PhC$_5$CO— | —KK— |
| MCC_000508 | [PhC$_5$CO—K(PhC$_5$CO]— | —K— |
| MCC_000509 | PhC$_8$CO— | —KK— |
| MCC_000510 | PhC$_9$CO— | —KK— |
| MCC_000511 | PhC$_{11}$CO— | —KK— |
| MCC_000512 | (4-Ph—PhC$_1$CO)— | —KK— |
| MCC_000513 | [(4-Ph—PhC$_1$CO)—K(4-Ph—PhC$_1$CO)]— | —K— |
| MCC_000514 | [4-(4-F—PhO)—PhCO]— | —KK— |
| MCC_000515 | {[4-(4-Cl—PhO)—PhCO—K[4-(4-F—PhO)—PhCO]}— | —K— |
| MCC_000516 | [4-(4-Cl—PhO)—PhCO]— | —KK— |
| MCC_000517 | {[4-(4-Cl—PhO)—PhCO—K[4-(4-Cl—PhO)—PhCO]}— | —K— |
| MCC_000518 | (4-BnO—PhCO)— | —KK— |
| MCC_000519 | [(4-BnO—PhCO)—K(4-BnOPhCO)]— | —K— |
| MCC_000520 | (nC$_9$-Pip-4-CO)— | —KK— |
| MCC_000521 | PhC$_9$CO— | —KK— |
| MCC_000522 | [4-(4-F—PhO)—PhCO)]— | —KK— |
| MCC_000523 | nC$_9$OPhCO— | —KK— |
| MCC_000546 | [nC$_7$CO—K(nC$_7$CO)]— | —K— |
| MCC_000547 | nC$_{11}$CO— | —KK— |
| MCC_000601 | [(C$_9$OPhCO)—K(C$_9$OPhCO)]— | —KK— |
| MCC_000602 | [(C$_5$OPhCO)—K(C$_5$OPhCO)]— | —KK— |
| MCC_000603 | [(PhOC$_3$CO)—K(PhOC$_3$CO)]— | —KK— |
| MCC_000604 | [(PhOC$_3$CO)—K(PhOC$_3$CO)]— | —KK— |
| MCC_000605 | nC$_{12}$CO— | —KK— |
| MCC_000606 | [(4-BnO—PhCO)—K(4-BnOPhCO)]— | —KK— |
| MCC_000607 | [(4-BnO—PhCO)—K(4-BnOPhCO)]— | —KK— |
| MCC_000627 | nC$_{13}$CO— | —K— |

TABLE 2-continued

Summary of Compound Structures

| | | |
|---|---|---|
| MCC_000628 | nC$_{13}$CO— | —K— |
| MCC_000629 | [(4-PhO—PhCO)—K(4-PhO—PhCO)]— | —K— |
| MCC_000630 | [(4-PhO—PhCO)—K(4-PhO—PhCO)]— | —K— |
| MCC_000635 | nC$_{13}$CO— | —KKK— |
| MCC_000647 | 4-PhO—PhCO— | —GKK— |
| MCC_000648 | nC$_{13}$CO— | —KK— |
| MCC_000649 | nC$_{13}$CO— | —KK— |
| MCC_000650 | (4-F—PhO—PhCO)—K(4-F—PhO—PhCO)— | —KK— |
| MCC_000651 | (4-F—PhO—PhCO)—K(4-F—PhO—PhCO)— | —KK— |
| MCC_000652 | (4-Ph—PhCH$_2$CO)—K(4-Ph—PhCH$_2$CO)— | —KK— |
| MCC_000653 | (4-Ph—PhCH$_2$CO)—K(4-Ph—PhCH$_2$CO)— | —KK— |
| MCC_000654 | (nC$_7$CO)—K(nC$_7$CO)— | —KK— |
| MCC_000655 | (nC$_7$CO)—K(nC$_7$CO)— | —KK— |
| MCC_000656 | (Ph—C$_{11}$CO)—K(Ph—C$_{11}$CO)— | —KK— |
| MCC_000657 | (Ph—C$_{11}$CO)—K(Ph—C$_{11}$CO)— | —KK— |
| MCC_000736 | [(4-PhO—PhCO)—K(4-PhO—PhCO)]— | —KK— |
| MCC_000737 | [(4-PhO—PhCO)—K(4-PhO—PhCO)]— | —KK— |
| MCC_000742 | nC$_{10}$CH$_2$— | —KK— |
| MCC_000744 | 4-PhO—PhCH$_2$— | —KK— |
| MCC_000764 | 4-MePh—SO$_2$— | —KK— |
| MCC_000766 | [(4-PhO—PhCO)—K(4-PhO—PhCO)]— | —DLys-DLys— |
| MCC_000767 | [(4-PhO—PhCO)—K(4-PhO—PhCO)]— | —DLys-K— |
| MCC_000768 | [(4-PhO—PhCO)—K(4-PhO—PhCO)]— | —OO— |
| MCC_000769 | (nC$_{12}$CO)—K(nC$_{12}$CO)— | —KK— |
| MCC_000770 | (nC$_{12}$CO)—K(nC$_{12}$CO)— | —KK— |
| MCC_000771 | (nC$_{13}$CO)—K(nC$_{13}$CO)— | —KK— |
| MCC_000772 | (nC$_{13}$CO)—K(nC$_{13}$CO)— | —KK— |
| MCC_000773 | (2-Bu—C$_7$CO)—K(2-Bu—C$_7$CO)— | —KK— |
| MCC_000774 | (2-Bu—C$_7$CO)—K(2-Bu—C$_7$CO)— | —KK— |
| MCC_000775 | (PhC$_5$CO)—K(PhC$_5$CO)— | —KK— |
| MCC_000776 | (PhC$_5$CO)—K(PhC$_5$CO)— | —KK— |
| MCC_000777 | [(4-PhO—PhCO)—K(4-PhO—PhCO)]— | —OO— |
| MCC_000778 | [(4-PhO—PhCO)—K(4-PhO—PhCO)]— | —KO— |
| MCC_000779 | [(4-PhO—PhCO)—K(4-PhO—PhCO)]— | —OK— |
| MCC_000782 | nC$_{10}$CO— | —KK— |
| MCC_000783 | nC$_{13}$CO— | —KK— |
| MCC_000784 | nC$_{13}$CO— | —KK— |
| MCC_000785 | nC$_{10}$CO— | —KKK— |
| MCC_000786 | nC$_{13}$CO— | —KKK— |
| MCC_000787 | [(4-PhO—PhCO)—K(4-PhO—PhCO)]— | —KKK— |
| MCC_000903 | nC$_{10}$CO— | —KK— |
| MCC_000904 | nC$_{10}$CO— | —KK— |
| MCC_000924 | [(4-PhO—PhCO)—K(4-PhO—PhCO)]— | —K-Dap— |
| MCC_000925 | [(4-PhO—PhCO)—K(4-PhO—PhCO)]— | —Dap-K— |
| MCC_000926 | [(4-PhO—PhCO)—K(4-PhO—PhCO)]— | —Dap-Dap— |
| MCC_000927 | [(4-PhO—PhCO)—K(4-PhO—PhCO)]— | —K-Dab— |
| MCC_000928 | [(4-PhO—PhCO)—K(4-PhO—PhCO)]— | —Dab-K— |
| MCC_000929 | [(4-PhO—PhCO)—K(4-PhO—PhCO)]— | —KK— |
| MCC_000930 | [(4-PhO—PhCO)—K(4-PhO—PhCO)]— | —KK— |
| MCC_000931 | [(4-PhO—PhCO)—K(4-PhO—PhCO)]— | —KK— |
| MCC_000936 | (nC$_9$-Pip-4-CO)— | —KK— |
| MCC_000937 | (nC$_9$-Pip-4-CO)— | —KK— |
| MCC_000938 | (nC$_9$-Pip-4-CO)— | —KKK— |
| MCC_000939 | nC$_{10}$CO— | —KK— |
| MCC_000940 | [(4-PhO—PhCO)—K(4-PhO—PhCO)]— | —KK— |
| MCC_000974 | nC$_{13}$CO— | —KK— |
| MCC_000975 | nC$_{12}$CO— | —KK— |
| MCC_000976 | nC$_{11}$CO— | —KK— |
| MCC_000977 | nC$_{12}$CO— | —KK— |
| MCC_000978 | nC$_{11}$CO— | —KK— |
| MCC_000979 | nC$_{13}$CO— | —KK— |
| MCC_000980 | nC$_{12}$CO— | —KK— |
| MCC_000981 | nC$_{11}$CO— | —KK— |
| MCC_004812 | (nC$_9$-Pip-4-CO)— | —K— |
| MCC_004815 | nC$_{10}$CH$_2$— | —KK— |
| MCC_004817 | (nC$_{11}$-Pip-4-CO)— | —KK— |
| MCC_004818 | (nC$_{11}$-Pip-4-CO)— | —KK— |
| MCC_004819 | (nC$_9$-Pip-4-CO)— | —KK— |
| MCC_004820 | (nC$_7$-Pip-4-CO)— | —KK— |
| MCC_004821 | 4-nC$_7$NH—PhCO— | —KK— |
| MCC_004822 | 4-MeNH—PhCO— | —KK— |
| MCC_004823 | 4-NH$_2$—PhCO— | —KK— |
| MCC_004825 | (nC$_9$-Pip-4-CO)— | —K— |
| MCC_004827 | (2-NH$_2$-nC$_9$CO)— | —KK— |
| MCC_004828 | (nC$_4$CH$_2$)2— | —KK— |
| MCC_004829 | nC$_{10}$CO— | —KK— |
| MCC_004830 | (nC$_9$-Pip-2-CO)— | —KK— |
| MCC_004831 | (1-nC$_9$-Pro)- | —KK— |

TABLE 2-continued

Summary of Compound Structures

| | | |
|---|---|---|
| MCC_004832 | (nC$_9$-Pip-2-CO)— | —KK— |
| MCC_004833 | (nC9-Pip-4-CO)— | —KK— |
| MCC_004901 | (nC$_4$CH2)2— | —KK— |
| MCC_004921 | nC$_8$CH2— | —KK— |
| MCC_004965 | nC$_9$CO— | —K— |
| MCC_004966 | nC$_9$CO— | —KK— |
| MCC_005041 | nC$_{10}$CO— | —KK— |
| MCC_005042 | nC$_{10}$CO— | —KK— |
| MCC_005043 | nC$_{10}$CO— | —KK— |
| MCC_005044 | nC$_{10}$CO— | —KK— |
| MCC_005061 | nC$_9$CO— | —K— |
| MCC_005062 | nC$_{10}$CO— | —K— |
| MCC_005063 | nC$_{11}$CO— | —K— |
| MCC_005064 | nC$_9$CO— | —KK— |
| MCC_005066 | nC$_{10}$CO— | —KKK— |
| MCC_005084 | nC$_9$CO— | —KK— |
| MCC_005085 | nC$_{10}$CO— | —KK— |
| MCC_005121 | nC$_9$CO— | —K(Me)$_2$— |
| MCC_005122 | nC$_{10}$CO— | —K(Me)— |
| MCC_005123 | nC$_9$CO— | —KKK— |
| MCC_005124 | 3,5-Me$_2$C$_7$CO— | —KK— |
| MCC_005125 | nC$_{10}$CO— | —K(Me)$_2$— |
| MCC_005126 | nC$_{10}$CO— | —KK— |
| MCC_005141 | nC$_{10}$CO— | —K(Me)K(Me)— |
| MCC_005145 | nC$_{10}$CO— | —Arg— |
| MCC_005146 | nC$_{10}$CO— | —His— |
| MCC_005161 | nC$_8$CO— | —K— |
| MCC_005162 | nC$_9$CO— | —K— |
| MCC_005163 | nC$_{10}$CO— | —K— |
| MCC_005164 | nC$_7$CO— | —KK— |
| MCC_005165 | nC$_8$CO— | —KK— |
| MCC_005166 | nC$_9$CO— | —KK— |
| MCC_005181 | nC$_9$CO— | —KKK— |
| MCC_005182 | nC$_{10}$CO— | —KKK— |
| MCC_005183 | nC$_7$CO— | —K— |
| MCC_005194 | nC$_9$CO(Me)— | —KK— |
| MCC_005196 | nC$_7$CO— | —KK— |
| MCC_005198 | nC$_{10}$CO— | —K— |
| MCC_005199 | nC$_8$CO— | —KK— |
| MCC_005200 | nC$_9$CO— | —K— |
| MCC_005201 | nC$_9$CO— | —KKK— |
| MCC_005202 | nC$_7$CO— | —K— |
| MCC_005203 | nC$_8$CO— | —K— |
| MCC_005222 | nC$_7$CO— | —K— |
| MCC_005223 | nC$_8$CO— | —K— |
| MCC_005224 | nC$_{11}$CO— | —K— |
| MCC_005225 | nC$_7$CO— | —KK— |
| MCC_005226 | nC$_8$CO— | —KK— |
| MCC_005361 | 4-nC$_5$O-PhCO— | —KK— |
| MCC_005362 | 4-Cl—PhCO— | —KK— |
| MCC_005363 | cHexCH$_2$CO— | —KK— |
| MCC_005364 | 4-PhO—PhCO— | —KK— |
| MCC_005365 | PhOC$_3$CO— | —KK— |
| MCC_005388 | nC$_2$CO— | —KK— |
| MCC_005481 | nC$_9$CO— | —Arg— |
| MCC_005482 | nC$_9$CO— | —Arg-Arg— |
| MCC_005483 | 3-OH—C$_9$CO— | —KK— |
| MCC_005484 | nC$_9$CO— | —Arg— |
| MCC_005485 | 4-nC$_5$-cHexCO— | —KK— |
| MCC_005486 | nC$_9$CO— | —K-Arg— |
| MCC_005487 | nC$_9$CO— | —Arg-K— |
| MCC_005488 | nC$_9$CO— | —K— |
| MCC_005489 | nC$_9$CO— | —KK— |
| MCC_005501 | PhOC$_3$CO— | —KK— |
| MCC_005502 | cHexCH$_2$CO— | —KK— |
| MCC_005503 | 4-nC$_5$-cHexCO— | —KK— |
| MCC_005504 | 4-nC$_5$O—PhCO— | —KK— |
| MCC_005505 | 4-Cl—PhCO— | —KK— |
| MCC_005506 | 3S-OH—C$_9$CO— | —KK— |
| MCC_005507 | nC$_9$CO— | —Arg-Arg— |
| MCC_005530 | nC$_9$CO— | —Arg— |
| MCC_007219 | 4-Cl—PhCO— | —K(Me)$_2$— |
| MCC_007221 | 4-PhO—PhCO— | —K(Me)$_2$— |
| MCC_007328 | nC$_9$CO— | —K[—(CH$_2$)$_5$—]— |
| MCC_007330 | nC$_9$CO— | —K(Et)$_2$— |
| MCC_007336 | nC$_8$CO— | —Arg— |
| MCC_007337 | nC$_{10}$CO— | —Arg— |
| MCC_007338 | nC$_8$CO— | —K(Me)$_2$— |

TABLE 2-continued

Summary of Compound Structures

| | | |
|---|---|---|
| MCC_007339 | nC$_9$CO— | —K(Me)$_2$— |
| MCC_007340 | nC$_{10}$CO— | —K(Me)$_2$— |
| MCC_007379 | nC$_9$CO— | —K[(CH$_2$)$_2$O(CH$_2$)$_2$—]— |
| MCC_007385 | nC$_8$CO— | —Arg— |
| MCC_007386 | nC$_8$CO— | —K(Me)$_2$— |
| MCC_007387 | nC$_{10}$CO— | —Arg(Me)$_2$— |
| MCC_007388 | nC$_8$CO— | —K(Me)$_3$— |
| MCC_007407 | 4-PhO—PhCO— | —K— |
| MCC_007408 | 4-CF$_3$—PhCO— | —K— |
| MCC_007409 | Indole-3-CO— | —K— |
| MCC_007410 | 2-Ph-pyridine-4-CO— | —K— |
| MCC_007412 | 4-PhO—PhCO— | —Arg— |
| MCC_007413 | 4-PhO—PhCO— | —Arg— |

| Compound Number | L | V* |
|---|---|---|
| MCC_000080 | (S)—NHCH(CO$_2$H)(CH$_2$)$_4$NH— | Va |
| MCC_000082 | (S)—NHCH(CO$_2$H)(CH$_2$)$_4$NH— | Va |
| MCC_000173 | (S)—NHCH(CONHMe)(CH$_2$)$_4$NH—COCH$_2$NH— | Va |
| MCC_000174 | (S)—NHCH(CO$_2$H)(CH$_2$)$_4$NH— | Va |
| MCC_000175 | (S)—NHCH(CO$_2$H)(CH$_2$)$_4$NH— | Va |
| MCC_000194 | (S)—NHCH(CO$_2$H)(CH$_2$)$_4$NH— | Va |
| MCC_000214 | (S)—NHCH(CO$_2$H)(CH$_2$)$_4$NH— | Va |
| MCC_000217 | (S)—NHCH(CO$_2$H)(CH$_2$)$_4$NH— | Va |
| MCC_000223 | (S)—NHCH(CO$_2$H)(CH$_2$)$_4$NH— | Va |
| MCC_000224 | (S)—NHCH(CONHMe)(CH$_2$)$_4$NH— | Va |
| MCC_000225 | (S)—NHCH(CO$_2$H)(CH$_2$)$_4$NH—COCH$_2$NH— | Va |
| MCC_000226 | —NHCH$_2$CO—NH(CH$_2$)$_2$NH— | Va |
| MCC_000227 | —NHCH$_2$CO—NH(CH$_2$)$_2$NH— | Va |
| MCC_000228 | —NHCH2CO—NH(CH$_2$)$_2$NH— | Va |
| MCC_000229 | (S)—NHCH(CO$_2$H)(CH$_2$)$_4$NH— | Va |
| MCC_000230 | (S)—NHCH(CO$_2$H)(CH$_2$)$_4$NH— | Va |
| MCC_000231 | (S)—NHCH(CO$_2$H)(CH$_2$)$_4$NH— | Va |
| MCC_000292 | (S)—NHCH(CONHMe)(CH$_2$)$_4$NH— | Va |
| MCC_000309 | (S)—NHCH(CONHMe)(CH$_2$)$_4$NH— | Va |
| MCC_000310 | (S)—NHCH(CONHMe)(CH$_2$)$_4$NH— | Va |
| MCC_000316 | (S)—NHCH(CONHMe)(CH$_2$)$_4$NH— | Va |
| MCC_000343 | (S)—NHCH(CONHMe)(CH$_2$)$_4$NH— | Va |
| MCC_000344 | —NH(CH$_2$)$_3$NH— | Va |
| MCC_000345 | —NH(CH$_2$)$_3$NH— | Va |
| MCC_000346 | (S)—NHCH(CO$_2$H)(CH$_2$)$_4$NH— | Va |
| MCC_000347 | (S)—NHCH(CO$_2$H)(CH$_2$)$_4$NH— | Va |
| MCC_000348 | (S)—NHCH(CO$_2$H)(CH$_2$)$_4$NH— | Va |
| MCC_000349 | (S)—NHCH(CO$_2$H)(CH$_2$)$_4$NH— | Va |
| MCC_000350 | (S)—NHCH(CO$_2$H)(CH$_2$)$_4$NH— | Va |
| MCC_000367 | —NHCH$_2$CO—NH(CH$_2$)$_2$NH— | Va |
| MCC_000380 | (S)—NHCH(CO$_2$H)(CH$_2$)$_4$NH— | Va |
| MCC_000381 | (S)—NHCH(CO$_2$H)(CH$_2$)$_4$NH— | Va |
| MCC_000453 | (S)—NHCH(CONH$_2$)—CH$_2$-(1,3-Triazole)-(CH$_2$)$_3$—NH— | Va |
| MCC_000455 | (S)—NHCH(CONH$_2$)(CH$_2$)$_4$NH— | Va |
| MCC_000489 | (S)—NHCH(CONHMe)(CH$_2$)$_4$NH— | Va |
| MCC_000490 | (S)—NHCH(CONHMe)(CH$_2$)$_4$NH— | Va |
| MCC_000491 | (S)—NHCH(CONHMe)(CH$_2$)$_4$NH— | Va |
| MCC_000492 | (S)—NHCH(CONHMe)(CH$_2$)$_4$NH— | Va |
| MCC_000493 | (S)—NHCH(CONHMe)(CH$_2$)$_4$NH— | Va |
| MCC_000494 | (S)—NHCH(CONHMe)(CH$_2$)$_4$NH— | Va |
| MCC_000495 | (S)—NHCH(CONHMe)(CH$_2$)$_4$NH— | Va |
| MCC_000496 | (S)—NHCH(CONHMe)(CH$_2$)$_4$NH— | Va |
| MCC_000497 | (S)—NHCH(CONHMe)(CH$_2$)$_4$NH— | Va |
| MCC_000498 | (S)—NHCH(CONHMe)(CH$_2$)$_4$NH— | Va |
| MCC_000499 | (S)—NHCH(CONHMe)(CH$_2$)$_4$NH— | Va |
| MCC_000500 | (S)—NHCH(CONHMe)(CH$_2$)$_4$NH— | Va |
| MCC_000501 | (S)—NHCH(CONHMe)(CH$_2$)$_4$NH— | Va |
| MCC_000502 | (S)—NHCH(CONHMe)(CH$_2$)$_4$NH— | Va |
| MCC_000503 | (S)—NHCH(CONHMe)(CH$_2$)$_4$NH— | Va |
| MCC_000504 | (S)—NHCH(CONHMe)(CH$_2$)$_4$NH— | Va |
| MCC_000505 | (S)—NHCH(CONHMe)(CH$_2$)$_4$NH— | Va |
| MCC_000506 | (S)—NHCH(CONHMe)(CH$_2$)$_4$NH— | Va |
| MCC_000507 | (S)—NHCH(CONHMe)(CH$_2$)$_4$NH— | Va |
| MCC_000508 | (S)—NHCH(CONHMe)(CH$_2$)$_4$NH— | Va |
| MCC_000509 | (S)—NHCH(CONHMe)(CH$_2$)$_4$NH— | Va |
| MCC_000510 | (S)—NHCH(CONHMe)(CH$_2$)$_4$NH— | Va |
| MCC_000511 | (S)—NHCH(CONHMe)(CH$_2$)$_4$NH— | Va |
| MCC_000512 | (S)—NHCH(CONHMe)(CH$_2$)$_4$NH— | Va |
| MCC_000513 | (S)—NHCH(CONHMe)(CH$_2$)$_4$NH— | Va |

TABLE 2-continued

Summary of Compound Structures

| | | |
|---|---|---|
| MCC_000514 | (S)—NHCH(CONHMe)(CH$_2$)$_4$NH— | Va |
| MCC_000515 | (S)—NHCH(CONHMe)(CH$_2$)$_4$NH— | Va |
| MCC_000516 | (S)—NHCH(CONHMe)(CH$_2$)$_4$NH— | Va |
| MCC_000517 | (S)—NHCH(CONHMe)(CH$_2$)$_4$NH— | Va |
| MCC_000518 | (S)—NHCH(CONHMe)(CH$_2$)$_4$NH— | Va |
| MCC_000519 | (S)—NHCH(CONHMe)(CH$_2$)$_4$NH— | Va |
| MCC_000520 | (S)—NHCH(CONHMe)(CH$_2$)$_4$NH— | Va |
| MCC_000521 | (S)—NHCH(CONHMe)(CH$_2$)$_4$NH— | Vb |
| MCC_000522 | (S)—NHCH(CONHMe)(CH$_2$)$_4$NH— | Vb |
| MCC_000523 | (S)—NHCH(CONHMe)(CH$_2$)$_4$NH— | Vb |
| MCC_000546 | (S)—NHCH(CONHMe)(CH$_2$)$_4$NH— | Vb |
| MCC_000547 | (S)—NHCH(CONHMe)(CH$_2$)$_4$NH— | Vb |
| MCC_000601 | (S)—NHCH(CONHMe)(CH$_2$)$_4$NH— | Va |
| MCC_000602 | (S)—NHCH(CONHMe)(CH$_2$)$_4$NH— | Va |
| MCC_000603 | (S)—NHCH(CONHMe)(CH$_2$)$_4$NH— | Va |
| MCC_000604 | (S)—NHCH(CONHMe)(CH$_2$)$_4$NH— | Vb |
| MCC_000605 | (S)—NHCH(CONHMe)(CH$_2$)$_4$NH— | Vb |
| MCC_000606 | (S)—NHCH(CONHMe)(CH$_2$)$_4$NH— | Va |
| MCC_000607 | (S)—NHCH(CONHMe)(CH$_2$)$_4$NH— | Vb |
| MCC_000627 | (S)—NHCH(CONHMe)(CH$_2$)$_4$NH— | Va |
| MCC_000628 | (S)—NHCH(CO$_2$H)(CH$_2$)$_4$NH— | Va |
| MCC_000629 | (S)—NHCH(CO$_2$H)(CH$_2$)$_4$NH— | Va |
| MCC_000630 | (S)—NHCH(CONHMe)(CH$_2$)$_4$NH— | Va |
| MCC_000635 | (S)—NHCH(CO$_2$Me)(CH$_2$)$_4$NH— | Va |
| MCC_000647 | (S)—NHCH(CONHMe)(CH$_2$)$_4$NH— | Va |
| MCC_000648 | (S)—NHCH(CONHMe)(CH$_2$)$_3$NH— | Va |
| MCC_000649 | (S)—NHCH(CONHMe)(CH$_2$)$_3$NH— | Vb |
| MCC_000650 | (S)—NHCH(CONHMe)(CH$_2$)$_4$NH— | Va |
| MCC_000651 | (S)—NHCH(CONHMe)(CH$_2$)$_4$NH— | Vb |
| MCC_000652 | (S)—NHCH(CONHMe)(CH$_2$)$_4$NH— | Va |
| MCC_000653 | (S)—NHCH(CONHMe)(CH$_2$)$_4$NH— | Vb |
| MCC_000654 | (S)—NHCH(CONHMe)(CH$_2$)$_4$NH— | Va |
| MCC_000655 | (S)—NHCH(CONHMe)(CH$_2$)$_4$NH— | Vb |
| MCC_000656 | (S)—NHCH(CONHMe)(CH$_2$)$_4$NH— | Va |
| MCC_000657 | (S)—NHCH(CONHMe)(CH$_2$)$_4$NH— | Vb |
| MCC_000736 | (S)—NHCH(CONHMe)(CH$_2$)$_3$NH— | Va |
| MCC_000737 | (R)—NHCH(CONHMe)(CH$_2$)$_4$NH— | Va |
| MCC_000742 | (S)—NHCH(CONHMe)(CH$_2$)$_4$NH— | Va |
| MCC_000744 | (S)—NHCH(CONHMe)(CH$_2$)$_4$NH— | Va |
| MCC_000764 | (S)—NHCH(CONHMe)(CH$_2$)$_4$NH— | Va |
| MCC_000766 | (S)—NHCH(CONHMe)(CH$_2$)$_4$NH— | Va |
| MCC_000767 | (S)—NHCH(CONHMe)(CH$_2$)$_4$NH— | Va |
| MCC_000768 | (S)—NHCH(CONHMe)(CH$_2$)$_4$NH— | Va |
| MCC_000769 | (S)—NHCH(CONHMe)(CH$_2$)$_4$NH— | Va |
| MCC_000770 | (S)—NHCH(CONHMe)(CH$_2$)$_4$NH— | Vb |
| MCC_000771 | (S)—NHCH(CONHMe)(CH$_2$)$_4$NH— | Va |
| MCC_000772 | (S)—NHCH(CONHMe)(CH$_2$)$_4$NH— | Vb |
| MCC_000773 | (S)—NHCH(CONHMe)(CH$_2$)$_4$NH— | Va |
| MCC_000774 | (S)—NHCH(CONHMe)(CH$_2$)$_4$NH— | Vb |
| MCC_000775 | (S)—NHCH(CONHMe)(CH$_2$)$_4$NH— | Va |
| MCC_000776 | (S)—NHCH(CONHMe)(CH$_2$)$_4$NH— | Vb |
| MCC_000777 | (S)—NHCH(CONHMe)(CH$_2$)$_4$NH— | Va |
| MCC_000778 | (S)—NHCH(CONHMe)(CH$_2$)$_4$NH— | Va |
| MCC_000779 | (S)—NHCH(CONHMe)(CH$_2$)$_4$NH— | Va |
| MCC_000782 | —NHCH$_2$CO—NH(CH$_2$)$_3$NH— | Va |
| MCC_000783 | —NHCH$_2$CO—NH(CH$_2$)$_3$NH— | Va |
| MCC_000784 | —NHCH$_2$CO—NH(CH$_2$)$_3$NH— | Va |
| MCC_000785 | —NH(CH$_2$)$_3$NH— | Va |
| MCC_000786 | —NH(CH$_2$)$_3$NH— | Va |
| MCC_000787 | —NH(CH$_2$)$_3$NH— | Va |
| MCC_000903 | (S)—NHCH(CONHEt)(CH$_2$)$_4$NH— | Va |
| MCC_000904 | (S)—NHCH(CONHBn)(CH$_2$)$_4$NH— | Va |
| MCC_000924 | (S)—NHCH(CONHMe)(CH$_2$)$_4$NH— | Va |
| MCC_000925 | (S)—NHCH(CONHMe)(CH$_2$)$_4$NH— | Va |
| MCC_000926 | (S)—NHCH(CONHMe)(CH$_2$)$_4$NH— | Va |
| MCC_000927 | (S)—NHCH(CONHMe)(CH$_2$)$_4$NH— | Va |
| MCC_000928 | (S)—NHCH(CONHMe)(CH$_2$)$_4$NH— | Va |
| MCC_000929 | (S)—NHCH(CONHMe)(CH$_2$)$_4$NH— | Vc |
| MCC_000930 | (S)—NHCH(CONHMe)(CH$_2$)$_4$NH— | Vd |
| MCC_000931 | (S)—NHCH(CONHMe)(CH$_2$)$_4$NH— | Ve |
| MCC_000936 | —NHCH$_2$CO—NH(CH$_2$)$_3$NH— | Va |
| MCC_000937 | —NH(CH$_2$)$_3$NH— | Va |
| MCC_000938 | —NH(CH$_2$)$_3$NH— | Va |
| MCC_000939 | —NH(CH$_2$)$_2$NH— | Va |
| MCC_000940 | —NH(CH$_2$)$_3$NH— | Va |
| MCC_000974 | (S)—NHCH(CONH$_2$)(CH$_2$)$_4$NH— | Va |
| MCC_000975 | (S)—NHCH(CONH$_2$)(CH$_2$)$_4$NH— | Va |
| MCC_000976 | (S)—NHCH(CONH$_2$)(CH$_2$)$_4$NH— | Va |

TABLE 2-continued

| Summary of Compound Structures | | |
|---|---|---|
| MCC_000977 | —NH(CH$_2$)$_3$NH— | Va |
| MCC_000978 | —NH(CH$_2$)$_3$NH— | Va |
| MCC_000979 | (S)—NHCH(CONH$_2$)—CH$_2$(1,3-Triazole)-(CH$_2$)$_3$—NH— | Va |
| MCC_000980 | (S)—NHCH(CONH$_2$)—CH$_2$(1,3-Triazole)-(CH$_2$)$_3$—NH— | Va |
| MCC_000981 | (S)—NHCH(CONH$_2$)—CH$_2$(1,3-Triazole)-(CH$_2$)$_3$—NH— | Va |
| MCC_004812 | (S)—NHCH(CONHMe)(CH$_2$)$_4$NH— | Va |
| MCC_004815 | (S)—NHCH(CONH$_2$)(CH$_2$)$_4$NH— | Va |
| MCC_004817 | (S)—NHCH(CONH$_2$)(CH$_2$)$_4$NH— | Va |
| MCC_004818 | (S)—NHCH(CONH$_2$)(CH$_2$)$_4$NH— | Va |
| MCC_004819 | (S)—NHCH(CONH$_2$)(CH$_2$)$_4$NH— | Va |
| MCC_004820 | (S)—NHCH(CONH$_2$)(CH$_2$)$_4$NH— | Va |
| MCC_004821 | (S)—NHCH(CONH$_2$)(CH$_2$)$_4$NH— | Va |
| MCC_004822 | (S)—NHCH(CONH$_2$)(CH$_2$)$_4$NH— | Va |
| MCC_004823 | (S)—NHCH(CONH$_2$)(CH$_2$)$_4$NH— | Va |
| MCC_004825 | (S)—NHCH(CONH$_2$)(CH$_2$)$_4$NH— | Va |
| MCC_004827 | (S)—NHCH(CONH$_2$)(CH$_2$)$_4$NH— | Va |
| MCC_004828 | (S)—NHCH(CONH$_2$)(CH$_2$)$_4$NH— | Va |
| MCC_004829 | (S)—NHCH(CONH$_2$)(CH$_2$)$_4$NH— | Vc |
| MCC_004830 | (S)—NHCH(CONH$_2$)(CH$_2$)$_4$NH— | Va |
| MCC_004831 | (S)—NHCH(CO$_2$H)(CH$_2$)$_4$NH— | Va |
| MCC_004832 | (S)—NHCH(CO$_2$H)(CH$_2$)$_4$NH— | Va |
| MCC_004833 | (S)—NHCH(CO$_2$H)(CH$_2$)$_4$NH— | Va |
| MCC_004901 | (S)—NHCH(CO$_2$H)(CH$_2$)$_4$NH— | Va |
| MCC_004921 | (S)—NHCH(CONH$_2$)(CH$_2$)$_4$NH— | Va |
| MCC_004965 | (S)—NHCH(CO$_2$H)(CH$_2$)$_4$NH— | Va |
| MCC_004966 | (S)—NHCH(CO$_2$H)(CH$_2$)$_4$NH— | Va |
| MCC_005041 | —NH(1,4-cHex)NH— | Va |
| MCC_005042 | —NHCH$_2$(1,4-cHex)CH$_2$NH— | Va |
| MCC_005043 | —NHCH$_2$(1,4-Ph)CH$_2$NH— | Va |
| MCC_005044 | —NHCH$_2$(1,3-Ph)CH$_2$NH— | Va |
| MCC_005061 | (S)—NHCH(CONH$_2$)(CH$_2$)$_4$NH— | Va |
| MCC_005062 | (S)—NHCH(CONH$_2$)(CH$_2$)$_4$NH— | Va |
| MCC_005063 | (S)—NHCH(CONH$_2$)(CH$_2$)$_4$NH— | Va |
| MCC_005064 | (S)—NHCH(CONH$_2$)(CH$_2$)$_4$NH— | Va |
| MCC_005066 | (S)—NHCH(CONH$_2$)(CH$_2$)$_4$NH— | Va |
| MCC_005084 | —NH(CH$_2$)$_3$NH— | Va |
| MCC_005085 | -piperidine-4-CH$_2$NH— | Va |
| MCC_005121 | (S)—NHCH(CO$_2$H)(CH$_2$)$_4$NH— | Va |
| MCC_005122 | (S)—NHCH(CO$_2$H)(CH$_2$)$_4$NH— | Va |
| MCC_005123 | (S)—NHCH(CO$_2$H)(CH$_2$)$_4$NH— | Va |
| MCC_005124 | (S)—NHCH(CO$_2$H)(CH$_2$)$_4$NH— | Va |
| MCC_005125 | (S)—NHCH(CO$_2$H)(CH$_2$)$_4$NH— | Va |
| MCC_005126 | (S)—NHCH(CO$_2$H)(CH$_2$)$_4$NH— | Vc |
| MCC_005141 | (S)—NHCH(CO$_2$H)(CH$_2$)$_4$NH— | Va |
| MCC_005145 | (S)—NHCH(CO$_2$H)(CH$_2$)$_4$NH— | Va |
| MCC_005146 | (S)—NHCH(CO$_2$H)(CH$_2$)$_4$NH— | Va |
| MCC_005161 | —NH(CH$_2$)$_2$NH— | Va |
| MCC_005162 | —NH(CH$_2$)$_2$NH— | Va |
| MCC_005163 | —NH(CH$_2$)$_2$NH— | Va |
| MCC_005164 | —NH(CH$_2$)$_2$NH— | Va |
| MCC_005165 | —NH(CH$_2$)$_2$NH— | Va |
| MCC_005166 | —NH(CH$_2$)$_2$NH— | Va |
| MCC_005181 | —NH(CH$_2$)$_2$NH— | Va |
| MCC_005182 | —NH(CH$_2$)$_2$NH— | Va |
| MCC_005183 | —NH(CH$_2$)$_2$NH— | Va |
| MCC_005194 | (S)—NHCH(CO$_2$H)(CH$_2$)$_4$NH— | Va |
| MCC_005196 | —NH(CH$_2$)$_3$NH— | Va |
| MCC_005198 | —NH(CH$_2$)$_3$NH— | Va |
| MCC_005199 | —NH(CH$_2$)$_3$NH— | Va |
| MCC_005200 | —NH(CH$_2$)$_3$NH— | Va |
| MCC_005201 | —NH(CH$_2$)$_3$NH— | Va |
| MCC_005202 | —NH(CH$_2$)$_3$NH— | Va |
| MCC_005203 | —NH(CH$_2$)$_3$NH— | Va |
| MCC_005222 | (S)—NHCH(CO$_2$H)(CH$_2$)$_4$NH— | Va |
| MCC_005223 | (S)—NHCH(CO$_2$H)(CH$_2$)$_4$NH— | Va |
| MCC_005224 | (S)—NHCH(CO$_2$H)(CH$_2$)$_4$NH— | Va |
| MCC_005225 | (S)—NHCH(CO$_2$H)(CH$_2$)$_4$NH— | Va |
| MCC_005226 | (S)—NHCH(CO$_2$H)(CH$_2$)$_4$NH— | Va |
| MCC_005361 | —NH(CH$_2$)$_3$NH— | Va |
| MCC_005362 | —NH(CH$_2$)$_3$NH— | Va |
| MCC_005363 | —NH(CH$_2$)$_3$NH— | Va |
| MCC_005364 | —NH(CH$_2$)$_3$NH— | Va |
| MCC_005365 | —NH(CH$_2$)$_3$NH— | Va |
| MCC_005388 | (S)—NHCH(CO$_2$H)(CH$_2$)$_4$NH— | Va |
| MCC_005481 | —NH(CH$_2$)$_3$NH— | Va |

TABLE 2-continued

| Summary of Compound Structures | | | |
|---|---|---|---|
| | MCC_005482 | —NH(CH$_2$)$_3$NH— | Va |
| | MCC_005483 | —NH(CH$_2$)$_3$NH— | Va |
| | MCC_005484 | -piperidine-4-CH$_2$NH— | Va |
| | MCC_005485 | —NH(CH$_2$)$_3$NH— | Va |
| | MCC_005486 | —NH(CH$_2$)$_3$NH— | Va |
| | MCC_005487 | —NH(CH$_2$)$_3$NH— | Va |
| | MCC_005488 | -piperidine-4-CH$_2$NH— | Va |
| | MCC_005489 | -piperidine-4-CH$_2$NH— | Va |
| | MCC_005501 | (S)—NHCH(CO$_2$H)(CH$_2$)$_4$NH— | Va |
| | MCC_005502 | (S)—NHCH(CO$_2$H)(CH$_2$)$_4$NH— | Va |
| | MCC_005503 | (S)—NHCH(CO$_2$H)(CH$_2$)$_4$NH— | Va |
| | MCC_005504 | (S)—NHCH(CO$_2$H)(CH$_2$)$_4$NH— | Va |
| | MCC_005505 | (S)—NHCH(CO$_2$H)(CH$_2$)$_4$NH— | Va |
| | MCC_005506 | (S)—NHCH(CO$_2$H)(CH$_2$)$_4$NH— | Va |
| | MCC_005507 | (S)—NHCH(CO$_2$H)(CH$_2$)$_4$NH— | Va |
| | MCC_005530 | (S)—NHCH(CO$_2$H)(CH$_2$)$_4$NH— | Va |
| | MCC_007219 | (S)—NHCH(CO$_2$H)(CH$_2$)$_4$NH— | Va |
| | MCC_007221 | (S)—NHCH(CO$_2$H)(CH$_2$)$_4$NH— | Va |
| | MCC_007328 | (S)—NHCH(CO$_2$H)(CH$_2$)$_4$NH— | Va |
| | MCC_007330 | (S)—NHCH(CO$_2$H)(CH$_2$)$_4$NH— | Va |
| | MCC_007336 | —NH(CH$_2$)$_3$NH— | Va |
| | MCC_007337 | —NH(CH$_2$)$_3$NH— | Va |
| | MCC_007338 | —NH(CH$_2$)$_3$NH— | Va |
| | MCC_007339 | —NH(CH$_2$)$_3$NH— | Va |
| | MCC_007340 | —NH(CH$_2$)$_3$NH— | Va |
| | MCC_007379 | (S)—NHCH(CO$_2$H)(CH$_2$)$_4$NH— | Va |
| | MCC_007385 | (S)—NHCH(CO$_2$H)(CH$_2$)$_4$NH— | Va |
| | MCC_007386 | (S)—NHCH(CO$_2$H)(CH$_2$)$_4$NH— | Va |
| | MCC_007387 | (S)—NHCH(CO$_2$H)(CH$_2$)$_4$NH— | Va |
| | MCC_007388 | —NH(CH$_2$)$_3$NH— | Va |
| | MCC_007407 | —NH(CH$_2$)$_3$NH— | Va |
| | MCC_007408 | —NH(CH$_2$)$_3$NH— | Va |
| | MCC_007409 | —NH(CH$_2$)$_3$NH— | Va |
| | MCC_007410 | —NH(CH$_2$)$_3$NH— | Va |
| | MCC_007412 | —NH(CH$_2$)$_3$NH— | Va |
| | MCC_007413 | (S)—NHCH(CO$_2$H)(CH$_2$)$_4$NH— | Va |

*Va = —CO-vancomycin,
Vb = —CO-desvancosamine vancomycin,
*Vc = —CO-vancomycin aglycon,
Vd = —CO-A40926 (http://aac.asm.org/content/31/12/1961.abstract),
Ve = —CO-telavancin

TABLE 3

| Characterisation of Synthesised Compounds | | | | |
|---|---|---|---|---|
| Compound Number | HPLC retention time (min) | MS (ES) m/z | HRMS (ES) m/z calculated | found |
| MCC_000080 | 6.26 | [M + 2H]2+ 936.8 | [M + 2H]2+ C89H121C12N13O27 936.8930 | 936.8940 |
| MCC_000082 | 5.39 | [M + 2H]2+ 1136.9 | [M + 3H]3+ C106H154C12N19O32 758.34560 | 758.3480 |
| MCC_000173 | 7.20 | [M + 2H]2+ 1036.0 | [M + 2H]2+ C98H139C12N17O28 1035.8 | 1035.9671 |
| MCC_000174 | 5.70 | [M + 2H]2+ 1001.3 | [M + 2H]2+ C95H133C12N15O28 1000.9411 | 1000.9431 |
| MCC_000175 | 6.20 | [M + 2H]2+ 1021.9 | [M + 2H]2+ C98H139C12N15O28 1021.9645 | 1021.9729 |
| MCC_000194 | 5.00 | [M + 2H]2+ 1079.3 | [M + 2H]2+ C103H133C12N17O30 1078.9378 | 1078.9442 |
| MCC_000213 | 7.10 | [M + 2H]2+ 873.5 | [M + 2H]2+ C83H109C12N11O26 872.846 | 872.8456 |
| MCC_000214 | 5.90 | [M + 2H]2+ 1014.8 | [M + 2H]2+ C97H121C12N15O29 1014.8916 | 1014.8879 |

TABLE 3-continued

Characterisation of Synthesised Compounds

| Compound Number | HPLC retention time (min) | MS (ES) m/z | HRMS (ES) m/z calculated | found |
|---|---|---|---|---|
| MCC_000217 | 6.70 | [M + 2H]2+ 1177.3 | [M + 2H]2+ C116H139Cl2N17O32 1176.9653 | 1176.9643 |
| MCC_000223 | 5.90 | [M + 2H]2+ 1086.9 | [M + 2H]2+ C104H149Cl2N17O29 1086.0120 | 1086.0111 |
| MCC_000224 | 6.30 | [M + 2H]2+ 1028.3 | [M + 2H]2+ C99H142Cl2N16O27 1028.4798 | 1028.4800 |
| MCC_000225 | 5.72 | [M + 2H]2+ 1029.3 | [M + 2H]2+ C97H136Cl2N16O29, 1176.96 | 1176.9647 |
| MCC_000226 | 6.02 | [M + 2H]2+ 1007.8 | [M + 4H]4+ C96H138N16O27Cl2 504.2318 | 504.2328 |
| MCC_000227 | 5.96 | [M + 2H]2+ 1007.9 | [M + 4H]4+ C96H138N16O27Cl2 504.2318 | 504.2330 |
| MCC_000228 | 5.90 | [M + 2H]2+ 994.2 | [M + 4H]4+ C94H134N16O27Cl2 497.2240 | 497.2240 |
| MCC_000229 | 5.50 | [M + 2H]2+ 1065.8 | [M + 2H]2+ C101H143Cl2N17O29 1064.4886 | 1064.9847 |
| MCC_000230 | 6.00 | [M + 2H]2+ 1241.3 | [M + 2H]2+ C122H151Cl2N19O33 1241.01218 | 1241.0154 |
| MCC_000231 | 6.80 | [M + 2H]2+ 1149.8 | [M + 2H]2+ C112H163Cl2N17O30 1149.0643 | 1149.0627 |
| MCC_000292 | 5.57 | [M + 2H]2+ 1007.8 | [M + 4H]4+ C96H138N16O27Cl2 504.2318 | 504.2315 |
| MCC_000309 | 5.30 | [M + 2H]2+ 1071.3 | [M + 2H]2+ C109H146Cl2N18O28 1071.5044 | 1071.9729 |
| MCC_000310 | 6.10 | [M + 2H]2+ 1185.2 | [M + 2H]2+ C117H142Cl2N18O31 1183.4811 | 1183.4809 |
| MCC_000316 | 5.90 | [M + 2H]2+ 1247.8 | [M + 2H]2+ C123H154Cl2N20O32 1247.5296 | 1247.5337 |
| MCC_000343 | 5.50 | [M + 2H]2+ 1092.4 | [M + 2H]2+ C105H152Cl2N18O28 1092.5279 | 1092.5257 |
| MCC_000344 | 5.59 | [M + 2H]2+ 964.93 | [M + 2H]2+ C92H129Cl2N15O26 964.9297 | 964.9300 |
| MCC_000345 | 6.04 | [M + 2H]2+ 985.95 | [M + 2H]2+ C95H135Cl2N15O26 985.9520 | 985.9534 |
| MCC_000346 | 5.43 | [M + 2H]2+ 1093.5 | [M + 3H]3+ C103H149Cl2N18O30 730.00 | 729.3349 |
| MCC_000347 | 5.96 | [M + 2H]2+ 1007.8 | [M + 3H]3+ C96H136Cl2N15O28 672.30 | 672.3013 |
| MCC_000348 | 5.57 | [M + 2H]2+ 1071.9 | [M + 2H]2+ C102H147Cl2N17O29 1071.9958 | 1072.0001 |
| MCC_000349 | 6.09 | [M + 2H]2+ 1014.8 | [M + 3H]3+ C97H138Cl2N15O28 676.97 | 676.9732 |
| MCC_000350 | 5.74 | [M + 2H]2+ 1078.9 | [M + 3H]3+ C103H150Cl2N17O29 676.97 | 719.6715 |
| MCC_000453 | 5.57 | [M + 2H]2+ 1033.8 | [M + 4H]4+ C97H137Cl2N19O27 517.4822 | 517.4899 |
| MCC_000455 | 5.40 | [M + 2H]2+ 1000.3 | [M + 4H]4+ C95H136N16O27Cl2 500.7279 | 500.7277 |

TABLE 3-continued

Characterisation of Synthesised Compounds

| Compound Number | HPLC retention time (min) | MS (ES) m/z | HRMS (ES) m/z calculated | found |
|---|---|---|---|---|
| MCC_000489 | 5.04 | [M + 2H]2+ 986.4 | [M + 3H]3+ C93H131N16O27Cl2 657.9577 | 657.9586 |
| MCC_000490 | 6.28 | [M + 2H]2+ 1051.7 | [M + 2H]2+ C101H146N16O28Cl2 525.2462 | 525.2469 |
| MCC_000491 | 5.24 | [M + 2H]2+ 995.2 | [M + 4H]4+ C94H134Cl2N16O27 497.8375 | 497.2240 |
| MCC_000492 | 5.38 | [M + 2H]2+ 1001.8 | [M + 4H]4+ C95H136Cl2N16O27 501.2732 | 500.7279 |
| MCC_000493 | 5.59 | [M + 2H]2+ 1015.7 | [M + 2H]2+ C97H138Cl2N16O27 1014.47 | 1014.4642 |
| MCC_000494 | 5.87 | [M + 2H]2+ 1021.4 | [M + 4H]4+ C98H142Cl2N16O27 511.7931 | 511.2396 |
| MCC_000495 | 6.04 | [M + 2H]2+ 1036.3 | [M + 3H]3+ C100H145Cl2N16O27 691.4059 | 690.6609 |
| MCC_000496 | 5.54 | [M + 2H]2+ 1015.7 | [M + 3H]3+ C97H139Cl2N16O27 676.643 | 676.6452 |
| MCC_000497 | 6.63 | [M + 2H]2+ 1105.4 | [M + 3H]3+ C109H161Cl2N16O28 737.367 | 737.3676 |
| MCC_000498 | 5.77 | [M + 2H]2+ 1028.58 | [M + 3H]3+ C99H141Cl2N16O27 685.32 | 685.3171 |
| MCC_000499 | 6.058 | [M + 2H]2+ 1017.43 | [M + 4H]4+ C98H134Cl2N16O27 509.226 | 509.2240 |
| MCC_000500 | 5.61 | [M + 2H]2+ 1026.2 | [M + 3H]3+ C99H135Cl2N16O27 683.302 | 683.3014 |
| MCC_000501 | 5.34 | [M + 2H]2+ 1018.3 | [M + 4H]4+ C97H132Cl2N16O28 509.72 | 509.7188 |
| MCC_000502 | 6.52 | [M + 2H]2+ 1113.8 | [M + 3H]3+ C109H145Cl2N16O30 742.654 | 742.6588 |
| MCC_000503 | 5.60 | [M + 2H]2+ 1034.2 | [M + 3H]3+ C99H135Cl2N16O28 688.634 | 688.6331 |
| MCC_000504 | 5.94 | [M + 2H]2+ 1048.2 | [M + 2H]2+ C101H138Cl2N16O28 1046.46 | 1046.4616 |
| MCC_000505 | 4.93 | [M + 2H]2+ 1004.3 | [M + 4H]4+ C95H128Cl2N16O28 502.712 | 502.7110 |
| MCC_000506 | 5.91 | [M + 2H]2+ 1085.9 | [M + 3H]3+ C105H137Cl2N16O30 723.97 | 723.9682 |
| MCC_000507 | 5.18 | [M + 2H]2+ 1011.7 | [M + 3H]3+ C97H131N16O27Cl2 673.9577 | 673.9543 |
| MCC_000508 | 6.45 | [M + 2H]2+ 1098.3 | [M + 3H]3+ C109H145Cl2N16O28 731.996 | 731.9925 |
| MCC_000509 | 5.59 | [M + 2H]2+ 1032.3 | [M + 4H]4+ C100H138Cl2N16O27 516.234 | 516.2318 |
| MCC_000510 | 5.74 | [M + 2H]2+ 1039.8 | [M + 4H]4+ C101H143N16O27Cl2 519.7357 | 519.7378 |
| MCC_000511 | 6.06 | [M + 2H]2+ 1053.8 | [M + 3H]3+ C103H143N16O27Cl2 701.9890 | 701.9863 |
| MCC_000512 | | | [M + 3H]3+ C99H127Cl2N16O27 680.612 | 680.6139 |

TABLE 3-continued

Characterisation of Synthesised Compounds

| Compound Number | HPLC retention time (min) | MS (ES) m/z | HRMS (ES) m/z calculated | found |
|---|---|---|---|---|
| MCC_000513 | 6.40 | [M + 2H]2+ 1118.8 | [M + 3H]3+ C98H124Cl2FN16O28 687.273 | 687.2705 |
| MCC_000514 | 5.25 | [M + 2H]2+ 1031.2 | [M + 3H]3+ C98H124N16O28FCl2 687.2705 | 687.2732 |
| MCC_000515 | 6.48 | [M + 2H]2+ 1137.8 | [M + 4H]4+ C111H132Cl2F2N16O30 569.218 | 569.2155 |
| MCC_000516 | 5.35 | [M + 2H]2+ 1039.7 | [M + 3H]3+ C98H124Cl3N16O28 692.594 | 692.5940 |
| MCC_000517 | 6.69 | [M + 2H]2+ 1155.6 | [M + 3H]3+ C111H131Cl4N16O30 769.264 | 769.2652 |
| MCC_000518 | 5.20 | [M + 2H]2+ 1028.4 | [M + 3H]3+ C99H127Cl2N16O28 685.946 | 685.9455 |
| MCC_000519 | 6.45 | [M + 2H]2+ 1134.7 | [M + 2H]2+ C113H136Cl2N16O30 1133.44 | 1133.4487 |
| MCC_000520 | 5.10 | [M + 2H]2+ 1041.9 | [M + 3H]3+ C100H144Cl2N17O27 694.99 | 694.9926 |
| MCC_000521 | 6.04 | [M + 3H]3+ 646.3 | [M + 3H]3+ C94H126Cl2N15O25 644.944 | 644.9470 |
| MCC_000522 | 5.57 | [M + 2H]2+ 960.2 | [M + 3H]3+ C91H111Cl2FN15O26 639.574 | 639.5723 |
| MCC_000523 | 6.29 | [M + 2H]2+ 976.3 | [M + 3H]3+ C94H126Cl2N15O26 650.278 | 650.2786 |
| MCC_000546 | 6.63 | [M + 2H]2+ 977.93 | | |
| MCC_000547 | 5.89 | [M + 2H]2+ 942.91 | | |
| MCC_000599 | 6.88 | [M + 2H]2+ 1049.3 | [M + 2H]2+ C104H117Cl2N13O30 1048.86 | 1048.8698 |
| MCC_000600 | 6.92 | [M + 2H]2+ 1055.8 | [M + 2H]2+ C105H120Cl2N14O29 1055.38 | 1055.3856 |
| MCC_000601 | 6.95 | [M + 2H]2+ 1235.3 | [M + 3H]3+ C123H173Cl2N18O31 822.7219 | 822.7292 |
| MCC_000602 | 6.20 | [M + 2H]2+ 1179.3 | [M + 2H]2+ C115H156Cl2N18O31 1177.5202 | 1177.5275 |
| MCC_000603 | 5.64 | [M + 2H]2+ 1150.1 | [M + 3H]3+ C111H149Cl2N18O31 766.65926 | 766.6666 |
| MCC_000604 | 5.93 | [M + 2H]2+ 1077.8 | [M + 3H]3+ C104H136Cl2N17O29 718.96106 | 718.9683 |
| MCC_000605 | 6.19 | [M + 2H]2+ 951.8 | | |
| MCC_000606 | 6.04 | [M + 2H]2+ 1199.2 | | |
| MCC_000607 | 6.04 | [M + 2H]2+ 1126.3 | | |
| MCC_000610 | 6.81 | [M + 2H]2+ 900.8 | [M + 2H]2+ C87H118Cl2N12O25 900.38 | 900.3849 |
| MCC_000614 | 7.00 | [M + 2H]2+ 894.3 | [M + 4H]4+ C86H116N11O26Cl2 596.2485 | 596.5810 |
| MCC_000627 | 5.10 | [M + 2H]2+ 965.7 | [M + 3H]3+ C93H131Cl2N14O26 643.29 | 643.2907 |
| MCC_000628 | 6.46 | [M + 2H]2+ 959.7 | [M + 3H]3+ C92H128Cl2N13O27 638.944 | 638.9468 |

TABLE 3-continued

Characterisation of Synthesised Compounds

| Compound Number | HPLC retention time (min) | MS (ES) m/z | HRMS (ES) m/z calculated | found |
|---|---|---|---|---|
| MCC_000629 | 6.55 | [M + 2H]2+ 1114.09 | [M + 3H]3+ C110H130Cl2N15O31 742.278 | 742.2806 |
| MCC_000630 | 6.35 | [M + 2H]2+ 1119.8 | [M + 2H]2+ C111H131Cl2N15O31 1119.94 | 1119.9251 |
| MCC_000635 | 5.68 | [M + 2H]2+ 1093.5 | [M + 4H]4+ C105H155Cl2N17O29 547.0060 | 547.0133 |
| MCC_000647 | 5.25 | [M + 2H]2+ 1049.7 | [M + 2H]2+ C100H127Cl2N17O29 1049.9103 | 1049.9176 |
| MCC_000648 | 5.98 | [M + 2H]2+ 1023.3 | [M + 3H]3+ C98H141Cl2N16O27 681.3098 | 681.3171 |
| MCC_000649 | 6.27 | [M + 2H]2+ 949.9 | [M + 3H]3+ C91H128Cl2N15O25 633.6116 | 633.6189 |
| MCC_000650 | 6.02 | [M + 2H]2+ 1203.7 | [M + 4H]4+ C117H144Cl2F2N18O31 601.2319 | 601.2392 |
| MCC_000651 | 6.3 | [M + 2H]2+ 1129.8 | [M + 2H]2+ C110H129Cl2F2N17O29 1129.9165 | 1129.9238 |
| MCC_000652 | 6.07 | [M + 2H]2+ 1181.4 | [M + 2H]2+ C119H148Cl2N18O29 1181.494 | 1181.5013 |
| MCC_000653 | 6.35 | [M + 2H]2+ 1111.2 | [M + 2H]2+ C112H135Cl2N17O27 1109.9467 | 1109.9540 |
| MCC_000654 | 5.81 | [M + 2H]2+ 1114.9 | [M + 2H]2+ C107H156Cl2N18O29 1113.5253 | 1113.5326 |
| MCC_000655 | 6.1 | [M + 2H]2+ 1042.8 | [M + 2H]2+ C100H143Cl2N17O27 1041.978 | 1041.9853 |
| MCC_000656 | 7.04 | [M + 2H]2+ 1247.4 | [M + 2H]2+ C127H180Cl2N18O29 1245.6192 | 1245.6265 |
| MCC_000657 | 7.39 | [M + 2H]2+ 1175.8 | [M + 3H]3+ C120H168Cl2N17O27 783.0479 | 783.0552 |
| MCC_000736 | 6.11 | [M + 2H]2+ 1177.8 | [M + 3H]3+ C116H143N18O31Cl2 784.65 | 784.6509 |
| MCC_000737 | 6.14 | [M + 2H]2+ 1185.2 | [M + 3H]3+ C117H145N18O31Cl2 789.323 | 789.3228 |
| MCC_000742 | 5.29 | [M + 2H]2+ 1001.8 | [M + 3H]3+ C96H139N16O26Cl2 667.315 | 667.3136 |
| MCC_000744 | 4.14 | [M + 2H]2+ 1014.4 | [M + 2H]2+ C98H127N16O27Cl2 676.604 | 676.6040 |
| MCC_000764 | 4.63 | [M + 2H]2+ 1000.4 | [M + 4H]4+ C92H124N16O28Cl2S 500.6962 | 500.6982 |
| MCC_000766 | | | [M + 4H]4+ C117H146Cl2N18O31 592.2439 | 592.2431 |
| MCC_000767 | 5.14 | [M + 2H]2+ 1185.8 | [M + 4H]4+ C117H146Cl2N18O31 592.2375 | 592.2439 |
| MCC_000768 | 6.09 | [M + 2H]2+ 1184.8 | [M + 4H]4+ C117H146Cl2N18O31 592.2439 | 592.2460 |
| MCC_000769 | 6.79 | [M + 2H]2+ 1185.4 | [M + 3H]3+ C117H177Cl2N18O31 789.40236 | 789.4096 |
| MCC_000770 | 7.19 | [M + 2H]2+ 1111.9 | [M + 2H]2+ C110H163Cl2N17O27 1112.0562 | 1112.0635 |

TABLE 3-continued

Characterisation of Synthesised Compounds

| Compound Number | HPLC retention time (min) | MS (ES) m/z | HRMS (ES) m/z calculated | found |
|---|---|---|---|---|
| MCC_000771 | 6.96 | [M + 2H]2+ 1198.9 | [M + 4H]4+ C119H182Cl2N18O29 599.3096 | 599.3169 |
| MCC_000772 | 7.33 | [M + 2H]2+ 1127.3 | [M + 3H]3+ C112H168Cl2N17O27 551.0479 | 551.0552 |
| MCC_000773 | 6.42 | [M + 2H]2+ 1170.9 | [M + 4H]4+ C115H174Cl2N18O29 585.29395 | 585.3012 |
| MCC_000774 | 6.71 | [M + 2H]2+ 1098.4 | [M + 3H]3+ C108H160Cl2N17O27 732.3604 | 732.3677 |
| MCC_000775 | 6.13 | [M + 2H]2+ 1163.2 | [M + 4H]4+ C115H158Cl2N18O29 581.26265 | 581.2699 |
| MCC_000776 | 6.40 | [M + 2H]2+ 1089.9 | [M + 3H]3+ C108H144Cl2N17O27 726.98533 | 726.9926 |
| MCC_000777 | 5.1 | [M + 2H]2+ 1170.7 | [M + 3H]3+ C115H141Cl2N18O31 779.9733 | 779.9790 |
| MCC_000778 | 5.05 | [M + 2H]2+ 1176.8 | [M + 4H]4+ C116H144Cl2N18O31 588.7325 | 588.7400 |
| MCC_000779 | 5.17 | [M + 2H]2+ 1177.8 | [M + 3H]3+ C116H143Cl2N18O31 784.6509 | 784.6490 |
| MCC_000782 | 5.49 | [M + 2H]2+ 987.8 | [M + 3H]3+ C93H128N16O27Cl2 657.9501 | 657.9577 |
| MCC_000783 | 5.93 | [M + 2H]2+ 1008.3 | [M + 3H]3+ C96H134N16O27Cl2 671.9660 | 671.9733 |
| MCC_000784 | 5.98 | [M + 2H]2+ 1017.3 | [M + 3H]3+ C97H136N16O27Cl2 676.63790 | 676.6452 |
| MCC_000785 | 5.32 | [M + 2H]2+ 1029.4 | [M + 3H]3+ C98H139N17O27Cl2 686.3134 | 686.3207 |
| MCC_000786 | 5.72 | [M + 2H]2+ 1049.9 | [M + 3H]3+ C101H145N17O27Cl2 700.3291 | 700.3364 |
| MCC_000787 | | | [M + 4H]4+ C119H147N19O31Cl2 603.0045 | 603.0045 |
| MCC_000903 | 5.63 | [M + 2H]2+ 1015.5 | [M + 3H]3+ C97H139Cl2N16O27 676.6452 | 676.6470 |
| MCC_000904 | 6.03 | [M + 3H]3+ 698.2 | | |
| MCC_000924 | 5.30 | [M + 2H]2+ 1162.4 | [M + 3H]3+ C114H139Cl2N18O31 775.3071 | 775.3040 |
| MCC_000925 | | | [M + 3H]3+ C114H139Cl2N18O31 775.3071 | 775.3040 |
| MCC_000926 | 5.36 | [M + 2H]2+ 1142.7 | [M + 3H]3+ C11H133Cl2N18O31 761.2915 | 761.2930 |
| MCC_000927 | 5.17 | [M + 2H]2+ 1169.4 | [M + 3H]3+ C115H141Cl2N18O31 779.9790 | 779.9770 |
| MCC_000928 | 5.38 | [M + 2H]2+ 1169.9 | [M + 3H]3+ C115H141Cl2N18O31 779.9790 | 779.9760 |
| MCC_000929 | 5.51 | [M + 2H]2+ 1032.7 | [M + 3H]3+ C104H122Cl2N17O24 687.6070 | 686.9413 |
| MCC_000930 | 5.91 | [M + 2H]2+ 1324.9 | [M + 3H]3+ C134H158Cl2N17O36 883.6805 | 883.6846 |

TABLE 3-continued

Characterisation of Synthesised Compounds

| Compound Number | HPLC retention time (min) | MS (ES) m/z | HRMS (ES) m/z calculated | found |
|---|---|---|---|---|
| MCC_000931 | 5.40 | [M + 2H]2+ 1338.0 | [M + 4H]4+ C131H177Cl2N20O34P 668.7957 | 668.7954 |
| MCC_000936 | 5.92 | [M + 3H]3+ 686.4 | [M + 5H]5+ C98H142Cl2N17O27 411.794 | 411.7922 |
| MCC_000937 | 5.94 | [M + 3H]3+ 667.1 | [M + 5H]5+ C96H139Cl2N16O26 400.387 | 400.3879 |
| MCC_000938 | 5.53 | [M + 3H]3+ 710.4 | [M + 5H]5+ C102H151Cl2N18O27 426.006 | 426.0069 |
| MCC_000939 | 6.34 | [M + 2H]2+ 958.9 | [M + 3H]3+ C91H128Cl2N15O26 638.951 | 638.9505 |
| MCC_000940 | 5.38 | [M + 2H]2+ 1142.8 | [M + 4H]4+ C113H139Cl2N17O30 570.981 | 570.9807 |
| MCC_000955 | 6.80 | [M + 2H]2+ 908.8 | [M + 2H]2+ C88H120Cl2N12O25 907.3927 | 907.3910 |
| MCC_000956 | 6.85 | [M + 2H]2+ 823.3 | [M + 2H]2+ C80H106Cl2N10O23 822.3399 | 822.3360 |
| MCC_000957 | 6.18 | [M + 2H]2+ 769.8 | [M + 3H]3+ C73H85Cl2N10O23 513.1717 | 513.1740 |
| MCC_000972 | | | [M + 2H]2+ C83H110Cl2N12O25 872.357 | 872.3536 |
| MCC_000974 | | | (ES) m/z [M + 2H]2+ C98H140Cl2N16O27 1021.4720 | 1021.4675 |
| MCC_000975 | | | (ES) m/z [M + 3H]3+ C97H139Cl2N16O27 676.6452 | 676.6477 |
| MCC_000976 | | | (ES) m/z [M + 2H]2+ C96H136Cl2N16O27 1007.4563 | 1007.4560 |
| MCC_000977 | | | (ES) m/z [M + 2H]2+ C94H133Cl2N15O26 978.9456 | 978.9412 |
| MCC_000978 | | | (ES) m/z [M + 2H]2+ C93H131Cl2N15O26 971.9378 | 971.9376 |
| MCC_000979 | | | (ES) m/z [M + 2H]2+ C100H141Cl2N19O27 1054.9805 | 1054.9774 |
| MCC_000980 | | | (ES) m/z [M + 2H]2+ C99H139Cl2N19O27 1047.9727 | 1047.9718 |
| MCC_000981 | | | (ES) m/z [M + 2H]2+ C98H137Cl2N19O27 1040.9649 | 1040.9630 |
| MCC_004812 | 6.28 | [M + 2H]2+ 977.5 | [M + 3H]3+ C94H132Cl2N15O26 652.2943 | 652.2970 |
| MCC_004815 | 5.13 | [M + 2H]2+ 993.5 | [M + 2H]2+ 95H136N16O26Cl2 993.455 | 993.4589 |
| MCC_004817 | 6.25 | [M + 2H]2+ 1056 | [M + 4]4+ C102H149Cl2N17O27 528.5041 | 528.5040 |
| MCC_004818 | 6.33 | [M + 2H]2+ 1049.9 | [M + 4]4+ C101H147Cl2N17O27 525.0002 | 525.0000 |
| MCC_004819 | 5.47 | [M + 2H]2+ 1035.9 | [M + 4H]4+ C99H143Cl2N17O27 517.9924 | 517.9940 |
| MCC_004820 | 4.89 | [M + 2H]2+ 1021.5 | [M + 3H]3+ C97H138Cl2N17O27 680.9770 | 680.9750 |

TABLE 3-continued

Characterisation of Synthesised Compounds

| Compound Number | HPLC retention time (min) | MS (ES) m/z | HRMS (ES) m/z calculated | found |
|---|---|---|---|---|
| MCC_004821 | 6.55 | [M + 2H]2+ 1024.4 | [M+3H]3+ C98H134Cl2N17O27 683.6332 | 683.6300 |
| MCC_004822 | 4.60 | [M + 2H]2+ 982.4 | [M + 4H]4+ C92H123Cl2N17O27 491.9532 | 491.9510 |
| MCC_004823 | 4.27 | [M + 2H]2+ 977.3 | [M + 4H]4+ C91H121Cl2N17O27 488.4493 | 488.4520 |
| MCC_004825 | 5.43 | [M + 2H]2+ 971.0 | [M + 4H]4+ C93H131Cl2N15O26 485.9686 | 485.9680 |
| MCC_004827 | 4.82 | [M + 2H]2+ 1001.9 | [M + 3H]3+ C94H134Cl2N17O27 667.6332 | 667.6360 |
| MCC_004828 | 4.82 | [M + 2H]2+ 987.9 | [M + 4H]4+ C94H136N16O26Cl2 493.731 | 493.7292 |
| MCC_004829 | 6.08 | [M + 2H]2+ 849.4 | [M + 2H]2+ C82H111Cl2N15O20 847.8748 | 847.8740 |
| MCC_004830 | 4.97 | [M + 2H]2+ 1035.4 | | |
| MCC_004831 | 5.11 | [M + 2H]2+ 1029.4 | [M + 2H]2+ C98H138Cl2N16O28 1028.4616 | 1028.4600 |
| MCC_004832 | 5.16 | [M + 2H]2+ 1034.9 | [M + 3H]3+ C99H141Cl2N16O28 690.6487 | 690.6520 |
| MCC_004833 | 5.24 | [M + 2H]2+ 1036.4, | [M + 3H]3+ C99H141Cl2N16O28 690.6487 | 690.6500 |
| MCC_004901 | | | [M + 4H]4+ C94H135Cl2N15O27 493.9752 | 493.9775 |
| MCC_004921 | | | | |
| MCC_004965 | 7.30 | [M + 2H]2+ 929.8 | [M + 3H]3+ C88H120Cl2N13O27 620.2592 | 620.261 |
| MCC_004966 | 6.67 | [M + 2H]2+995.2 | [M + 4H]4+ C94H133Cl2N15O28 497.4700 | 497.47 |
| MCC_005041 | 6.74 | [M + 2H]2+ 986.0 | [M + 4H]4+ C95H135Cl2N15O26 492.977 | 492.9764 |
| MCC_005042 | 7.31 | [M + 3H]3+ 666.7 | [M + 4H]4+ C97H139Cl2N15O26 499.985 | 499.9843 |
| MCC_005043 | 6.87 | [M + 2H]2+ 995.5 | [M + 4H]4+ C97H133Cl2N15O26 498.475 | 498.4725 |
| MCC_005044 | 7.98 | [M + 2H]2+ 996.9 | [M + 4H]4+ C97H133Cl2N15O26 498.475 | 498.4725 |
| MCC_005061 | | | [M + 3H]3+ C88H121Cl2N14O26 619.9312 | 619.933 |
| MCC_005062 | | | [M + 3H]3+ C89H123Cl2N14O26 624.6031 | 624.6048 |
| MCC_005063 | | | [M + 3H]3+ C90H125Cl2N14O26 629.2750 | 629.273 |
| MCC_005064 | | | [M + 4H]4+ C94H134Cl2N16O27 497.2240 | 497.2236 |
| MCC_005066 | 5.31 | [M + 2H]2+ 959.7 | [M + 4H]4+ C101H149Cl2N18O28 426.4028 | 426.4018 |
| MCC_005084 | 4.54 | [M + 2H]2+ 985.3 | [M + 4H]4+ C91H129Cl2N15O26 479.4647 | 479.466 |

TABLE 3-continued

Characterisation of Synthesised Compounds

| Compound Number | HPLC retention time (min) | MS (ES) m/z | HRMS (ES) m/z calculated | found |
|---|---|---|---|---|
| MCC_005085 | 5.87 | [M + 2H]2+ 944.2 | [M + 4H]4+ C95H135Cl2N15O26 492.9764 | 492.978 |
| MCC_005121 | 5.93 | [M + 2H]2+ 943.7 | [M + 3H]3+ C90H124Cl2N13O27 629.6030 | 629.603 |
| MCC_005122 | 5.15 | [M + 2H]2+ 1059.2 | [M + 3H]3+ C90H124Cl2N13O27 629.6030 | 629.605 |
| MCC_005123 | 5.36 | [M + 2H]2+ 993.8 | [M + 4H]4+ C100H145Cl2N17O29 529.4937 | 529.493 |
| MCC_005124 | 7.83 | [M + 2H]2+ 950.7 | [M + 4H]4+ C94H133Cl2N15O28 497.4700 | 497.471 |
| MCC_005125 | 7.83 | [M + 2H]2+ 950.7 | [M + 3H]3+ C91H126Cl2N13O27 634.2749 | 634.277 |
| MCC_005126 | 6.25 | [M + 2H]2+ 849.7 | [M + 3H]3+ C82H111Cl2N14O21 565.9136 | 565.915 |
| MCC_005141 | 5.57 | [M + 2H]2+ 1016.2 | [M + 4H]4+ C97H139Cl2N15O28 507.9817 | 507.982 |
| MCC_005145 | 7.92 | [M + 2H]2+ 952.2 | [M + 3H]3+ C89H122Cl2N15O27 634.2665 | 634.266 |
| MCC_005146 | 7.93 | [M + 2H]2+ 941.2 | [M + 3H]3+ C89H117Cl2N14O27 627.9191 | 627.92 |
| MCC_005161 | 6.47 | [M + 2H]2+ 881.1 | [M + 4H]4+ C83H112Cl2N13O25 586.9084 | 586.907 |
| MCC_005162 | 5.6 | [M + 2H]2+ 886.7 | [M + 3H]3+ C84H114Cl2N13O25 591.5803 | 591.579 |
| MCC_005163 | 5.75 | [M + 2H]2+ 895.1 | [M + 3H]3+ C85H116Cl2N13O25 596.2522 | 596.25 |
| MCC_005164 | 4.92 | [M + 2H]2+ 938.6 | [M + 4H]4+ C88H123Cl2N15O26 468.9530 | 468.953 |
| MCC_005165 | 5.07 | [M + 2H]2+ 945.2 | [M + 4H]4+ C89H125Cl2N15O26 472.4569 | 472.458 |
| MCC_005166 | 5.26 | [M + 2H]2+ 950.7 | [M + 4H]4+ C90H127Cl2N15O26 475.9608 | 475.961 |
| MCC_005181 | 4.89 | [M + 3H]3+ 677.4 | [M + 4H]4+ C96H139Cl2N17O27 507.9845 | 507.99 |
| MCC_005182 | 5.05 | [M + 2H]2+ 1023.7 | [M + 4H]4+ C97H141Cl2N17O27 511.4884 | 511.49 |
| MCC_005183 | 5.24 | [M + 2H]2+ 872.7 | [M + 3H]3+ C82H110Cl2N13O25 582.2365 | 582.239 |
| MCC_005194 | 5.79 | [M + 2H]2+ 936.7 | [M + 3H]3+ C89H122Cl2N13O27 624.9311 | 624.932 |
| MCC_005196 | 5.01 | [M + 2H]2+ 943.7 | [M + 4H]4+ C89H125Cl2N15O26 472.4569 | 472.458 |
| MCC_005198 | 5.93 | [M + 2H]2+ 902.1 | [M + 3H]3+ C86H118Cl2N13O25 600.9241 | 600.921 |
| MCC_005199 | 5.20 | [M + 2H]2+ 951.6 | [M + 4H]4+ C90H127Cl2N15O26 475.9608 | 475.959 |
| MCC_005200 | 5.73 | [M + 2H]2+ 895.6 | [M + 3H]3+ C85H116Cl2N13O25 596.2522 | 596.247 |

TABLE 3-continued

Characterisation of Synthesised Compounds

| Compound Number | HPLC retention time (min) | MS (ES) m/z | HRMS (ES) m/z calculated | found |
|---|---|---|---|---|
| MCC_005201 | 5.03 | [M + 2H]2+ 1023.2 | [M + 4H]4+ C97H141Cl2N17O27 511.4884 | 511.486 |
| MCC_005202 | 5.37 | [M + 2H]2+ 879.8 | [M + 3H]3+ C83H112Cl2N13O25 586.9084 | 586.906 |
| MCC_005203 | 5.56 | [M + 2H]2+ 886.7 | [M + 3H]3+ C84H114Cl2N13O25 591.5803 | 591.577 |
| MCC_005222 | 6.56 | [M + 2H]2+ 1221.4 | [M + 4H]4+ C86H116Cl2N13O27 610.913 | 610.9155 |
| MCC_005223 | 6.56 | [M + 2H]2+ 1230.7 | [M + 4H]4+ C87H118Cl2N13O27 615.589 | 615.5874 |
| MCC_005224 | 8.25 | [M + 2H]2+ 1259.4 | [M + 4H]4+ C90H124Cl2N13O27 629.603 | 629.603 |
| MCC_005225 | 5.64 | [M + 2H]2+ 981.2 | [M + 4H]4+ C92H129Cl2N15O28 490.462 | 490.4622 |
| MCC_005226 | 6.07 | [M + 2H]2+ 988.2 | [M + 4H]4+ C93H131Cl2N15O28 493.968 | 493.9661 |
| MCC_005361 | 5.25 | [M + 2H]2+ 977.7 | [M + 4H]4+ C93H125Cl2N15O27 488.4556 | 488.457 |
| MCC_005362 | 4.90 | [M + 2H]2+ 950.9 | [M + 4H]4+ C88H114Cl3N15O26 475.4276 | 475.427 |
| MCC_005363 | 4.89 | [M + 2H]2+ 942.9 | [M + 4H]4+ C89H123Cl2N15O26 471.9530 | 471.951 |
| MCC_005364 | 5.22 | [M + 2H]2+ 979.4 | [M + 4H]4+ C94H119Cl2N15O27 489.9439 | 489.943 |
| MCC_005365 | 4.97 | [M + 2H]2+ 963.6 | [M + 4H]4+ C91H121Cl2N15O27 481.4478 | 481.446 |
| MCC_005388 | 4.72 | [M + 2H]2+ 944.9 | [M + 4H]4+ C87H119Cl2N15O28 472.9426 | 472.944 |
| MCC_005481 | 7.32 | [M + 2H]2+ 907.7 | [M + 3H]3+ C85H116Cl2N15O25 605.586 | 605.5876 |
| MCC_005482 | 6.33 | [M + 2H]2+ 986.5 | [M + 4H]4+ C91H129Cl2N19O26 493.47 | 493.4678 |
| MCC_005483 | 4.17 | [M + 2H]2+ 965.7 | [M + 4H]4+ C91H129Cl2N15O27 483.464 | 483.4634 |
| MCC_005484 | 7.50 | [M + 2H]2+ 928.5 | [M + 3H]3+ C88H120Cl2N15O25 618.932 | 618.9313 |
| MCC_005485 | 5.47 | [M + 2H]2+ 971.6 | [M + 4H]4+ C93H131Cl2N15O26 485.971 | 485.9686 |
| MCC_005486 | 5.40 | [M + 2H]2+ 971.7 | [M + 4H]4+ C91H129Cl2N17O26 486.468 | 486.4662 |
| MCC_005487 | 5.40 | [M + 2H]2+ 973.1 | [M + 4H]4+ C91H129Cl2N17O26 486.469 | 486.4662 |
| MCC_005488 | 5.86 | [M + 2H]2+ 914.5 | [M + 3H]3+ C88H120Cl2N13O25 609.594 | 609.596 |
| MCC_005489 | 6.23 | [M + 2H]2+ 978.2 | [M + 4H]4+ C94H133Cl2N15O26 489.474 | 489.4725 |
| MCC_005501 | 1.54 | [M + 2H]2+ 998.4 | [M + 4H]4+ C94H125Cl2N15O29 499.4531 | 499.4530 |

TABLE 3-continued

Characterisation of Synthesised Compounds

| Compound Number | HPLC retention time (min) | MS (ES) m/z | HRMS (ES) m/z calculated | found |
|---|---|---|---|---|
| MCC_005502 | 1.52 | [M + 2H]2+ 979.4 | [M + 4H]4+ C92H127Cl2N15O28 489.9583 | 489.9559 |
| MCC_005503 | 1.76 | [M + 2H]2+ 1007.4 | [M + 4H]4+ C96H135Cl2N15O28 503.9739 | 503.9762 |
| MCC_005504 | 1.69 | [M + 2H]2+ 1012.4 | [M + 4H]4+ C96H129Cl2N15O29 506.4609 | 506.4623 |
| MCC_005505 | 1.51 | [M + 2H]2+ 986.5 | [M + 4H]4+ C91H118Cl3N15O28 493.4329 | 493.4313 |
| MCC_005506 | 1.62 | [M + 2H]2+ 1002.4 | [M + 4H]4+ C94H133Cl2N15O29 501.4687 | 501.4697 |
| MCC_005507 | 3.30 | [M + 2H]2+ 1022.70 | [M + 4H]4+ C94H133Cl2N19O28 511.4731 | 511.4728 |
| MCC_005530 | 3.81 | [M + 2H]2+ 944.50 | [M + 3H]3+ C88H120Cl2N15O27 629.5946 | 629.594 |
| MCC_007219 | 5.55 | [M + 2H]2+ 936.8 | [M + 3H]3+ C87H109Cl3N13O27 624.2202 | 629.2196 |
| MCC_007221 | 5.89 | [M + 2H]2+ 965.3 | [M + 3H]3+ C93H114Cl2N13O28 643.5752 | 643.5736 |
| MCC_007328 | 11.54 | [M + 2H]2+ 963 | [M + 3H]3+ C93H128Cl2N13O27 642.9468 | 642.9471 |
| MCC_007330 | 9.16 | [M + 2H]2+ 957.4 | [M + 3H]3+ C92H128Cl2N13O27 638.9468 | 638.9474 |
| MCC_007336 | 7.06 | [M + 2H]2+ 901.8 | [M + 3H]3+ C84H114Cl2N15O25 600.9157 | 600.9170 |
| MCC_007337 | 7.95 | [M + 2H]2+ 916.3 | [M + 3H]3+ C86H118Cl2N15O25 610.2595 | 610.2574 |
| MCC_007338 | 7.93 | [M + 2H]2+ 901.4 | [M + 3H]3+ C86H118Cl2N13O25 600.9241 | 600.9260 |
| MCC_007339 | 7.94 | [M + 2H]2+ 909.4 | [M + 3H]3+ C87H120Cl2N13O25 605.5960 | 605.5964 |
| MCC_007340 | 8.10 | [M + 2H]2+ 914.5 | [M + 3H]3+ C88H122Cl2N13O25 610.2678 | 610.2680 |
| MCC_007379 | 9.26 | [M + 2H]2+ 965.8 | [M + 3H]3+ C92H126Cl2N13O28 643.6065 | 643.6089 |
| MCC_007385 | 3.50 | [M + 2H]2+ 937.6 | [M + 3H]3+ C87H118Cl2N15O27 624.9227 | 624.9202 |
| MCC_007386 | 3.90 | [M + 2H]2+ 937.4 | [M + 3H]3+ C89H122Cl2N13O27 624.9311 | 624.9307 |
| MCC_007387 | 4.20 | [M + 2H]2+ 965.90 | [M + 3H]3+ C91H126Cl2N15O27 643.6103 | 643.6127 |
| MCC_007388 | 9.06 | [M + 2H]2+ 951.90 | [M + 3H]3+ C91H127Cl2N13O27 634.2749 | 634.2765 |
| MCC_007407 | 1.98 | [M + 2H]2+ 915.20 | [M + 3H]3+ C88H106Cl2N13O26 610.2244 | 610.2239 |
| MCC_007408 | 3.64 | [M + 2H]2+ 903.40 | [M + 3H]3+ C83H101Cl2F3N13O25 602.2115 | 602.2125 |
| MCC_007409 | 2.72 | [M + 2H]2+ 888.90 | [M + 3H]3+ C84H103Cl2N14O25 592.5526 | 592.5552 |

TABLE 3-continued

Characterisation of Synthesised Compounds

| Compound Number | HPLC retention time (min) | MS (ES) m/z | HRMS (ES) m/z calculated | HRMS (ES) m/z found |
|---|---|---|---|---|
| MCC_007410 | 3.35 | [M + 2H]2+ 908.6 | [M + 3H]3+ C87H105Cl2N14O25 605.2245 | 605.2244 |
| MCC_007412 | 7.11 | [M + 2H]2+ 929.8 | [M + 3H]3+ C88H106Cl2N15O26 619.5598 | 619.5601 |
| MCC_007413 | 7.30 | [M + 2H]2+ 965.8 | [M + 3H]3+ C91H110Cl2N15O28 643.5668 | 643.5656 |

Determination of Antimicrobial Activity

Antimicrobial activity of compounds was tested against a number of bacterial strains, including *Staphylococcus aureus* (MRSA ATCC 43300, GISA NRS17, VISA NRS1, MRSA clinical isolate, daptomycin resistant clinical isolate), *Streptococcus pneumoniae* (MDR ATCC 700677), *Enterococcus faecalis* (VanA clinical isolate) and *Enterococcus faecium* (MDR Van A ATCC 51559).

All compounds were prepared to 160 µg/ml solution in water from a stock solution of 1 mM concentration.

MIC Assay:

The compounds, along with standard antibiotics were serially diluted twofold across the wells of 96-well non-binding surface plates (NBS, Corning). Standards ranged from 64 µg/ml to 0.03 µg/ml and compounds from 8 µg/ml to 0.003 µg/ml with final volumes of 50 µL per well. Gram positive bacteria were cultured in Muller Hinton broth (MHB) (Bacto laboratories, Cat. no. 211443) at 37° C. overnight. A sample of each culture was then diluted 40-fold in fresh MHB broth and incubated at 37° C. for 2-3 hrs. The resultant mid-log phase cultures were diluted to the final concentration of 5×10e5 CFU/mL, then 50 µL was added to each well of the compound-containing 96-well plates. All the plates were covered and incubated at 37° C. for 24 h. MICs were the lowest concentration showing no visible growth.

MBC Assay:

For the determination of the minimal bactericidal concentration (MBC), 30 µl of Resazurin (0.01%) was added to each well of the 96 well plates after the MIC values were determined. The compounds were then incubated at 37° C. for a further 18 to 24 h. Wells with blue coloration indicate dead microorganism, whereas wells with pink coloration indicate live microorganism. The MBC value was determined by the lowest concentrations of the wells with blue coloration.

Detection and Analysis:

MICs were determined visually at 24 hr incubation and the MIC was defined as the lowest concentration with which no growth was visible after incubation. Both MIC and MBC were determined by visual inspection only.

Summary of Biological Results

The antibacterial activities measured above are summarised in the following table for three representative bacterial strains.

TABLE 4

Minimum Inhibitory Concentration (MIC) of Compounds

MIC (mg/L)
x = >4, xx = 1-4, xxx = 0.1-<1,
xxxx = 0.01-<0.1, xxxxx = <0.01

| Compound | Staph. aureus ATCC43300 | S. pneumoniae ATCC 700677 | E. faecium ATCC51559 |
|---|---|---|---|
| MCC_000080 | xxx | xxx | x |
| MCC_000174 | xxxx | xxxx | x |
| MCC_000194 | xxx | xxx | x |
| MCC_000214 | xxx | xxx | x |
| MCC_000217 | xxxxx | xxxxx | xx |
| MCC_000223 | xxxxx | xxxxx | xxx |
| MCC_000224 | xxxxx | xxxxx | xxx |
| MCC_000225 | xxx | xxx | x |
| MCC_000226 | xxxxx | xxxxx | xxx |
| MCC_000227 | xxxxx | xxxxx | xx |
| MCC_000228 | xxxxx | xxxxx | xxxx |
| MCC_000229 | xxxx | xxx | xxxx |
| MCC_000230 | xxxxx | xxxx | xxx |
| MCC_000231 | xx | xx | x |
| MCC_000292 | xxxx | xxxx | xx |
| MCC_000309 | xxxxx | xxxxx | xxx |
| MCC_000310 | xxxxx | xxxxx | xxx |
| MCC_000316 | xxxxx | xxxxx | xxxx |
| MCC_000343 | xxxxx | xxxxx | xxxx |
| MCC_000344 | xxxx | xxxx | xx |
| MCC_000345 | xxxxx | xxxxx | xxxx |
| MCC_000346 | xxxx | xxxx | x |
| MCC_000347 | xxxxx | xxxx | xx |
| MCC_000348 | xxxxx | xxxxx | xxx |
| MCC_000349 | xxxxx | xxxxx | xxx |
| MCC_000350 | xxxxx | xxxxx | xxx |
| MCC_000367 | xxxx | xxx | x |
| MCC_000380 | xxxx | xxxxx | |
| MCC_000381 | xxx | xx | x |
| MCC_000453 | xxxx | xxxx | xx |
| MCC_000455 | xxxxx | xxxxx | xxx |
| MCC_000489 | xx | xxx | x |
| MCC_000490 | xxxx | xxxxx | x |
| MCC_000491 | xxx | xxx | x |
| MCC_000492 | xxxxx | xxxxxx | x |
| MCC_000493 | xxxxx | xxxxx | xx |
| MCC_000494 | xxxxx | xxxxx | xx |
| MCC_000495 | xxxx | xxxxx | xxx |
| MCC_000496 | xxxx | xxx | x |
| MCC_000497 | xxx | xxx | xxx |
| MCC_000498 | xx | xx | x |
| MCC_000499 | xxxx | xxxx | xx |
| MCC_000500 | xxxxx | xxxxx | xx |
| MCC_000501 | xxxx | xxxxx | x |
| MCC_000502 | xxxxx | xxxxx | xxx |
| MCC_000503 | xxxxx | xxxxx | xx |
| MCC_000504 | xxxxx | xxxxx | xxx |

TABLE 4-continued

Minimum Inhibitory Concentration (MIC) of Compounds

MIC (mg/L)
x = >4, xx = 1-4, xxx = 0.1-<1,
xxxx = 0.01-<0.1, xxxxx = <0.01

| Compound | Staph. aureus ATCC43300 | S. pneumoniae ATCC 700677 | E. faecium ATCC51559 |
|---|---|---|---|
| MCC_000505 | xxx | xx | x |
| MCC_000506 | xxx | xxx | x |
| MCC_000507 | xxx | xxx | x |
| MCC_000508 | xxxxx | xxxxx | xx |
| MCC_000509 | xxxx | xxxxx | xx |
| MCC_000510 | xxxx | xxxxxx | xx |
| MCC_000511 | xxxxx | xxxxx | xxx |
| MCC_000512 | xxx | xxx | x |
| MCC_000513 | xxxxx | xxxxx | xx |
| MCC_000514 | xxx | xxx | x |
| MCC_000515 | xxxxx | xxxxx | xx |
| MCC_000516 | xxxxxx | xxxxx | x |
| MCC_000517 | xxxx | xxxxxx | xxx |
| MCC_000518 | xxx | xxx | x |
| MCC_000519 | xxxxx | xxxxx | xx |
| MCC_000520 | xxxx | xxxxx | xx |
| MCC_000521 | xxx | xxx | x |
| MCC_000522 | xx | xx | x |
| MCC_000523 | xxxx | xxxx | xxx |
| MCC_000546 | xxx | xxx | x |
| MCC_000547 | xxx | xxx | x |
| MCC_000601 | x | x | x |
| MCC_000602 | xxxxx | xxxxx | xxxx |
| MCC_000603 | xxx | xxx | x |
| MCC_000604 | xx | xx | x |
| MCC_000605 | xxxx | xxx | x |
| MCC_000606 | xxxxx | xxxxx | xxx |
| MCC_000607 | xxxx | xxxx | xx |
| MCC_000627 | xxxxx | xxxxx | xx |
| MCC_000628 | xxxx | xxxx | x |
| MCC_000629 | xx | xx | x |
| MCC_000630 | xxxxx | xxxx | xx |
| MCC_000635 | xxxxx | xxxxx | xxxxx |
| MCC_000647 | xxx | xxx | x |
| MCC_000648 | xxxxx | xxxxx | xxx |
| MCC_000649 | xxxxx | xxxx | xx |
| MCC_000650 | xxxxx | xxxx | xxx |
| MCC_000651 | xxxxx | xxxx | xx |
| MCC_000652 | xxxxx | xxxxx | xxx |
| MCC_000653 | xxxx | xxxx | xx |
| MCC_000654 | xxxxx | xxxx | xx |
| MCC_000655 | xxxx | xxxx | x |
| MCC_000656 | x | x | x |
| MCC_000657 | x | x | x |
| MCC_000736 | xxxxx | xxxxx | xxx |
| MCC_000737 | xxxxx | xxxx | xxx |
| MCC_000742 | xxxx | xxxx | xxx |
| MCC_000744 | xxx | xxx | x |
| MCC_000764 | xx | xx | x |
| MCC_000766 | xxxxx | xxxxx | xx |
| MCC_000767 | xxxxx | xxxxx | xx |
| MCC_000768 | xxxxx | xxxxx | x |
| MCC_000769 | x | x | x |
| MCC_000770 | x | x | x |
| MCC_000771 | x | x | x |
| MCC_000772 | x | x | x |
| MCC_000773 | xxxx | xxxx | xxx |
| MCC_000774 | xxxx | xxxx | xxx |
| MCC_000775 | xxxxx | xxxxx | xxx |
| MCC_000776 | xxxx | xxx | xx |
| MCC_000777 | xxxxx | xxxxx | xxx |
| MCC_000778 | xxxxx | xxxxx | xx |
| MCC_000779 | xxxxx | xxxxx | xxx |
| MCC_000782 | xxxxx | xxxx | xx |
| MCC_000783 | xxxxx | xxxxx | xxx |
| MCC_000784 | xxxxx | xxxxx | xxxx |
| MCC_000785 | xxxx | xxxx | xxx |
| MCC_000786 | xxxxx | xxxx | xxx |
| MCC_000787 | xxxxx | xxxx | xxx |
| MCC_000903 | xxxx | xxxx | x |
| MCC_000904 | x | x | x |
| MCC_000924 | xxxxx | xxxxx | xxx |
| MCC_000925 | xxxxx | xxxxx | xxx |
| MCC_000926 | xxxxx | xxxxx | xxx |
| MCC_000927 | xxxxx | xxxxx | xx |
| MCC_000928 | xxxxx | xxxxx | xxx |
| MCC_000929 | xxx | xxx | xx |
| MCC_000930 | x | x | x |
| MCC_000931 | xx | xx | xxx |
| MCC_000936 | xxxx | xxxx | xx |
| MCC_000937 | xxxx | xxxx | xx |
| MCC_000938 | xxxx | xxxx | xx |
| MCC_000939 | xxxx | xxxxx | xx |
| MCC_000940 | xxxxx | xxxxx | xx |
| MCC_000974 | xxxx | xxxxx | xxx |
| MCC_000975 | xxxxx | xxxxx | xxx |
| MCC_000976 | xxxxx | xxxxx | xxx |
| MCC_000977 | xxxxx | xxxxx | xxx |
| MCC_000978 | xxxxx | xxxxx | xxx |
| MCC_000979 | xxxxx | xxxxx | xxx |
| MCC_000980 | xxxxx | xxxxx | xxx |
| MCC_000981 | xxxxx | xxxxx | xxx |
| MCC_004812 | xxxx | xxxx | xx |
| MCC_004815 | xxxx | xxxxx | xxx |
| MCC_004817 | xxxx | xxxx | xx |
| MCC_004818 | xxxx | xxxx | xxx |
| MCC_004819 | xxxx | xxxx | xx |
| MCC_004820 | xxxx | xxx | x |
| MCC_004821 | xxxx | xxxx | xx |
| MCC_004822 | xxx | xx | x |
| MCC_004823 | xx | xx | x |
| MCC_004825 | xxxx | xxx | xxx |
| MCC_004827 | xxxx | xxx | x |
| MCC_004828 | xxxx | xxx | x |
| MCC_004829 | xxxx | xxxx | xx |
| MCC_004830 | xxxx | xxxx | xx |
| MCC_004831 | xxxx | xxx | xx |
| MCC_004832 | xxxx | xxx | xx |
| MCC_004833 | xxxx | xxxx | xx |
| MCC_004901 | xxx | xx | x |
| MCC_004921 | xxxx | xxxx | x |
| MCC_004965 | xxx | xxx | x |
| MCC_004966 | xxx | xxx | x |
| MCC_005041 | xxxx | xxxx | xx |
| MCC_005042 | xxxxx | xxxxx | xxx |
| MCC_005043 | xxxxx | xxxxx | xx |
| MCC_005044 | xxxxx | xxxxx | xxx |
| MCC_005061 | xxxx | xxxx | x |
| MCC_005062 | xxxx | xxxx | x |
| MCC_005063 | xxxxx | xxxxx | xx |
| MCC_005064 | xxxx | xxxx | x |
| MCC 005066 | xxxx | xxxx | xx |
| MCC_005084 | xxxx | xxxx | xx |
| MCC_005085 | xxxx | xxxx | xx |
| MCC_005121 | xxx | | |
| MCC_005122 | xxxx | xxx | x |
| MCC_005123 | xxxx | xxxx | x |
| MCC_005124 | xxx | xxx | x |
| MCC_005125 | xxx | xxxx | x |
| MCC_005126 | xxxx | xxxx | xx |
| MCC_005141 | xxxx | xxx | x |
| MCC_005145 | xxxx | xxxx | x |
| MCC_005146 | xxx | xxx | x |
| MCC_005161 | xxxx | xxx | x |
| MCC_005162 | xxxx | xxxx | xx |
| MCC_005163 | xxxxx | xxxx | x |
| MCC_005164 | xxx | xxx | x |
| MCC_005165 | xxxx | xxxx | x |
| MCC_005166 | xxxx | xxxx | x |
| MCC_005181 | xxxxx | xxxx | xx |

TABLE 4-continued

Minimum Inhibitory Concentration (MIC) of Compounds

MIC (mg/L)
x = >4, xx = 1-4, xxx = 0.1-<1,
xxxx = 0.01-<0.1, xxxxx = <0.01

| Compound | Staph. aureus ATCC43300 | S. pneumoniae ATCC 700677 | E. faecium ATCC51559 |
|---|---|---|---|
| MCC_005182 | xxxxx | xxxx | xx |
| MCC_005183 | xxx | xxx | x |
| MCC_005194 | xxx | xxx | x |
| MCC_005196 | xxx | xxx | xx |
| MCC_005198 | xxxx | xxxx | xx |
| MCC_005199 | xxxx | xxxx | xx |
| MCC_005200 | xxxx | xxxx | xx |
| MCC_005201 | xxxx | xxxx | xx |
| MCC_005202 | xxx | xxx | x |
| MCC 005203 | xxx | xxx | x |
| MCC_005222 | xx | xx | x |
| MCC_005223 | xxx | xx | x |
| MCC_005224 | xxxx | xxxx | xx |
| MCC_005225 | xx | xx | x |
| MCC_005226 | xxx | xxx | x |
| MCC_005361 | xxxx | xxxx | xx |
| MCC_005362 | xxx | xxx | xx |
| MCC_005363 | xxx | xxx | x |
| MCC_005364 | xxxxx | xxxx | xx |
| MCC_005365 | xxx | xxx | x |
| MCC_005388 | xx | x | x |
| MCC_005481 | xxxxx | xxxx | x |
| MCC_005482 | xxxxx | xxxxx | xx |
| MCC_005483 | xxxx | xxxx | x |
| MCC_005484 | xxxxx | xxxxx | x |
| MCC_005485 | xxxxx | xxxxx | xx |
| MCC_005486 | xxxxx | xxxx | xx |
| MCC_005487 | xxxxx | xxx | xxx |
| MCC_005488 | xxxx | xxxx | xx |
| MCC_005489 | xxxx | xxxx | xx |
| MCC_005501 | xx | xx | x |
| MCC_005502 | xx | xx | x |
| MCC_005503 | xxxx | xxxx | xx |
| MCC_005504 | xxx | xxx | x |
| MCC_005505 | xx | xx | x |
| MCC_005506 | xxx | xxx | x |
| MCC_005507 | xxxx | xxxx | x |
| MCC 005530 | xxxx | xxx | x |
| MCC_007219 | xx | x | x |
| MCC_007221 | xxx | xx | x |
| MCC_007328 | xxx | xxx | x |
| MCC_007330 | xxx | xxx | x |
| MCC_007337 | xxxxx | xxxxx | xx |
| MCC_007338 | xxx | xxx | x |
| MCC_007339 | xxxx | xxxx | xx |
| MCC_007340 | xxxxx | xxxx | xx |
| MCC_007379 | xx | xx | x |
| MCC_007385 | xxx | xxx | x |
| MCC_007386 | xx | xx | x |
| MCC_007387 | xxxx | xxxx | x |
| MCC_007388 | xxx | xx | x |
| MCC_007407 | xxxx | xxxx | x |
| MCC_007408 | xxxx | xxx | x |
| MCC_007409 | xxx | xxx | x |
| MCC_007410 | xxx | xxx | x |
| MCC_007412 | xxxx | xxxx | x |
| MCC_007413 | xxx | xxx | x |

Stability of Compounds in Human Plasma

The human plasma stability assay was performed according to method described in "Di, L.; Kerns, E. H.; Hong, Y.; Chen, H. Development and application of high throughput plasma stability assay for drug discovery (International Journal of Pharmaceutics 2005, 297, 110-119", with modifications).

Briefly test compounds (20 μM) were prepared from a 1 mM stock solution. The human plasma sample (200 μl) was diluted with 160 μl phosphate-buffer saline (PBS, pH 7.4) to a concentration of 50% v/v before use. Solutions were then vortexed and placed on a 37° C. shaker and shaken gently for 10 minutes. 40 μl of the test compounds were then added to the plasma sample and vortexed. For the reaction time t=0 hour, 50 μl of sample was immediately transferred into an eppendorf tube and quenched with 150 μl cold acetonitrile. The remaining plasma solution was incubated and shaken at 37° C. Other samples were collected at time points of 0, 1, 3, 6 and 24 hours whereby 50 μl aliquots were removed and quenched with 150 μl cold acetonitrile. All samples were placed in a 4° C. fridge for 10 minutes then centrifuged at 3000 rpm for 15 minutes. The supernatant (100 μl) was transferred to a glass vial insert for LCMS analysis. The percentage of test compounds remaining at the individual time points relative to sample at time point 0 hour were reported.

Protocol:

Chemicals: DMSO, acetonitrile and phosphate-buffered saline (PBS pH 7.4, isotonic).

Plasma: Human Plasma (Pooled Normal Human Plasma Heparin Anticoagulant 50 mL (IPLA-2 N-04 lot IR09-1001, originally from Innovative Research and imported by Bio-Core).

Consumables: Eppendorf tubes (eucatropine and vancomycin), low binding Eppendorf tubes (for compounds) and Agilent glass HPLC vials and inserts.

Equipment: 37° C. shaker, vortexer, centrifuge and LC-MS.

Stock Solutions:

All compounds in 100% water (40 μL in 400 μL assay volume equivalent 35 to 20 μM)

Eucatropine: 300 μg/mL in 100% DMSO (10 μL in 400 μL assay volume equivalent to 23 μM)

Plasma Stability Assay Procedure

Preparation of Buffer Only Control Samples:

Compounds: 40 μL of the vancomycin derivative solution was added to 160 μL of PBS (pH 7.4) respectively in an Eppendorf tube. 600 μL of cold acetonitrile was added, the tube vortexed and transferred to a glass vial for LC-MS analysis.

Plasma Stability Protocol for Time 0, 1, 3, 6 and 24 hr for 50% Plasma and PBS Buffer:

Eucatropine: 200 μL of plasma and 190 μL of buffer were vortexed, shaken at 37° C. for 10 minutes. 10 μL of eucatropine solution was then added and the tube vortexed. A 50 μL aliquot was immediately transferred to an Eppendorf tube, 150 μL of cold acetonitrile added and the tube transferred to a 4° C. fridge for 10 minutes. The remaining plasma solution was then transferred to the incubator and shaken at 37° C. The tube was retrieved from the fridge, centrifuged at 3000 rpm for 15 min and 100 μL of supernatant transferred to a glass vial insert for LC-MS analysis. 50 μL aliquots were processed as above at 1, 2, 3, 6 and 24 hours and 5 μL was injected into triple quad MS system for analysis.

Vancomycin derivatives: 200 μL of plasma and 160 μL of buffer were vortexed and shaken at 37° C. for 10 minutes. 40 μL of compound was then added and the sample was processed as above.

TABLE 5

Compound Remaining after 24 h Incubation with 50% Human Plasma

| Compound | | % compound remaining after incubation in 50% human plasma | | | | |
|---|---|---|---|---|---|---|
| | | 0 h | 1 h | 3 h | 6 h | 24 h |
| MCC_000095 | vancomycin | 100 | 176 | 145 | 149 | 65 |
| MCC_000080 | nC10CO-K-K(Vanc)-OH | 100 | 101 | 101 | 100 | 89 |
| MCC_000082 | nC10CO-GSKKK-K(Vanc)-OH | 100 | 136 | 252 | 241 | 73 |
| MCC_000199 | nC13CO-GSKKKC(SEtNH-Vanc)-OH (SEQ ID NO: 1) | 100 | 119 | nd | 82 | 18 |
| MCC_000214 | (4-PhO-PhCO)-KK-K(Vanc)-OH | 100 | 101 | nd | 107 | 111 |
| MCC_000217 | (4-PhO-PhCO)-K(4-PhO-PhCO)-KK-K(Vanc)-OH | 100 | 107 | nd | 103 | 99 |
| MCC_000223 | nC13CO-KKK-K(Vanc)-OH | 100 | 174 | 164 | 170 | 139 |
| MCC_000535 | nC13CO-KKK-C(SS-nEt-NH-Vanc)-OH | 100 | 77 | 64 | 51 | 3 |
| MCC_000226 | nC13CO-KKG-NHC2NH-Vanc | 100 | 98 | 137 | 85 | 87 |
| MCC_000227 | nC13CO-kkG-NHC2NH-Vanc | 100 | 102 | 102 | 93 | 94 |
| MCC_000229 | nC10CO-KKK-K(Vanc)-OH | 100 | 87 | 87 | 83 | 93 |

Stability of Compounds in Presence of Glutathione

The stability of compounds in the presence of physiological concentrations of glutathione was assessed according to the protocol below: 20 µl of a 1 mM stock solution of the test compound was added to 180 µl of glutathione (reduced form) PBS solution within a plastic HPLC insert, providing a solution with a final concentration of 100 µM of compound and either 5 mM or 0.5 mM in glutathione. The sample was placed in a HPLC sampling rack and sampled at hourly intervals up to 10 hours. Care was taken to prepare the sample immediately before injection. The UV area was then plotted for the loss of compound against time. Percentages were plotted relative to total vancomycin derivative at 0 hours. Results are shown in FIG. 1.

Pharmacokinetic Profile of Compounds in Mice

In vivo experimental assay: Seven to nine week old male CD1 mice (SLAC Laboratory Animal Co. Ltd., Shanghai, China) weighing 25-35 g were acclimated for approximate 3 days before being used in the study. Animals are group housed during acclimation and in-life study in compliance with the National Research Council "Guide for the Care and Use of Laboratory Animals." The animal room environment is controlled (target conditions: temperature 18 to 26° C., relative humidity 30 to 70%, 12 hours artificial light and 12 hours dark) with temperature and relative humidity monitored daily. Animals were deprived of food for approximately 16 hours before formulation administration then allowed access to Certified Rodent Diet (Catalog #M-01F, Shanghai SLAC Laboratory Animal Co. Ltd.) ad libitum 4 hours post dosing. Water is autoclaved before being provided to the animals ad libitum. Formulations of compounds were prepared on the morning of the dosing day. The formulation for the IV group was filtered with filter of 0.22 µm before being dosed to animals. After dose formulation preparation, duplicate 50 µL aliquots were removed from each dose formulation for use in dose validation.

For each compound studied, 3 mice were dosed intravenously (IV) administered to each animal via tail vein per facility SOPs using test article formulated in deionized water at 1 mg/mL with a dose volume of 2 mL/kg, providing a dose of 2 mg/kg (based on free base concentration). An additional 3 mice were dosed subcutaneously (SC) administered to each animal via subcutaneous bolus on each animals' back per facility SOPs using test article formulated in deionized water at 2 mg/mL with a dose volume of 5 mL/kg, providing a dose of 10 mg/kg.

All animals were euthanized at the last study time point (100% CO2 was introduced into the animal box).

Sample Collection: Plasma samples were collected as the following target times after each dose administration:

IV Sampling Time points (hours post dosing): 0, 0.083, 0.25, 0.5, 1, 2, 4, 8, 24.

SC Sampling Time points (hours post dosing): 0, 0.25, 0.5, 1, 2, 4, 8, 24.

Approximately 30 µL blood was obtained via submandibular or saphenous vein for the first several time points. For the last time point, samples were collected via cardiac puncture while the mouse was under anesthesia (100% CO2 introduced into the animal box). All blood samples were transferred into pre-chilled plastic microcentrifuge tubes containing 2 µL of K2-EDTA (0.5M) as anticoagulant and placed on wet ice until centrifugation. Harvested blood samples were centrifuged within 30 min of collection at 7,000 rpm 4° C. for about 10 minutes. After centrifugation, plasma was transferred into another pre-labeled and pre-chilled polypropylene microcentrifuge tubes, then quick-frozen over dry ice, and stored at −70±10° C. until LC/MSMS analysis.

Sample Analysis:

Dosing Formulations Verification: Aliquots of the formulations were collected in the middle position of each dose formulation in duplicate. A LC-UV method was developed with a calibration curve consisting of 6 calibration standards. The concentrations of the test compound in dose formulation samples were determined by the LC-UV method. Acceptance criteria for an analytical run: at least of 5 of 6 calibration standards should be within 20% of nominal values.

Plasma Samples: LC-MS/MS methods for the quantitative determination of the test article in study used animal plasma were developed with an internal standard. Benchtop stability of the compound in mouse plasma was determined at mid QC concentrations in triplicate at 0, 2 hours at room temperature. The stability was determined using mean peak area ratio of T2/T0 sample. If the mean peak area ratio is within 80%~120%, the test article in the plasma is considered stable for 2 hours at room temperature. A standard curve consists of 8 non-zero calibration standards for the LC-MS/MS method with a target LLOQ at ≤3 ng/mL. A set of QC samples consists of three concentration levels (low, middle and high). The sample analysis was performed concurrently with a set of calibration standards and two sets of QC samples using the LC-MS/MS method. Acceptance criteria for plasma bioanalytical run: A minimum of 6 calibration standards is back calculated to within ±20% of their nominal concentrations; and a minimum of 4 out of 6 QC samples is back calculated to within ±20% of their nominal concentrations. Analyte interference: The mean calculated concentration in the single blank matrix should be ≤0.5 times the LLOQ. Carryover: the mean calculated carry-over concentration in the single blank matrix immediately after the highest standard injection should be ≤LLOQ.

DATA ANALYSIS: Plasma concentration versus time data from individual animals was analyzed by WinNonLin non-compartmental model (Phoenix WinNonlin 6.2.1, Pharsight, Mountain View, Calif.). Pharmacokinetic parameter C0, T½, CL, Vdss, Cmax, Tmax, AUC0-last, AUC0-inf, % F, MRT0-last, MRT0-inf and graphs of plasma concentration versus time profile were derived and are illustrated in FIG. 2.

Efficacy of Compounds in Murine Thigh Infection Model

Summary: Adult (8 week old) female CD1 mice were made neutropenic by two injections of cyclophosphamide 4 days and 1 day prior to infection. An inoculum of $10^5$ cfu MRSA (Strain ATCC 43300) was injected intramuscularly into both left and right thighs of all mice. Two hours after initiation of infection, saline, vancomycin, or compounds of this invention were injected subcutaneously in the lower back region. After an additional two hours, a 50 µL sample of blood was obtained from the tail bleed to analyse for presence of antibiotic compound. At 24 hours following infection, mice were euthanized and an additional blood sample collected for compound analysis. Thighs were then removed, weighed and homogenised in a fixed volume of saline. The homogenate solution was filtered, diluted and seeded onto agar plates, which were incubated overnight at 37° C. Colony counts were used to establish the cfu in the thigh homogenates, the cfu/thigh, and the cfu/g of thigh.

Compound preparation: Cyclophosphamide monohydrate (Sigma) was dissolved in sterile saline to a concentration of 30 mg/mL. Likewise, vancomycin (Sigma) and MCC compounds were also dissolved in sterile saline to a final concentration of 60 mg/mL and 18.5 mg/mL respectively. All compounds were prepared in low binding Eppendorf tubes and kept at −20° C. until used.

In vivo experimental assay: Eight week old female outbred CD1 mice (UQBR-AIBN) were rendered neutropenic by injecting two doses of cyclophosphamide intraperitoneally 4 days (150 mg/kg) and 1 day (100 mg/kg) prior to experimental infection. The infection model using MRSA was established by intramuscular injection of 50 µL of early-log-phase bacterial MRSA suspension (around 2×106 cfu/mL) in saline into both thigh muscles. Two hours later, a single dose of vancomycin (200 mg/kg) or compound of this invention (25 mg/kg) was administered by a subcutaneous injection over the interscapular (area at back of the neck). Untreated animals received equivalent volume of saline (Baxter). The mice were monitored for signs of normal behaviour (i.e. grooming, eating, drinking, sleeping, and alertness) during and following dosing. Two hours after saline/antibiotic treatment, 0.05 mL of blood was collected by tail incision. 24 hours after MRSA infection, mice were euthanized and blood collected from the heart by cardiac puncture (saline group) or by tail incision (Vancomycin and MCC compound treated groups) as outlined in FIG. 1. For each mouse, both thighs were collected aseptically by cutting the leg at the hip and knee, placed in 10 mL of cold sterile saline and the individual weight of each thigh recorded.

Preparation of injectable MRSA solution: An MRSA subculture bacterial isolate (ATCC43300) was taken from the storage at −80° C. and freshly seeded on agar plates for overnight (O/N) growth. From the O/N culture preparation, a single colony was diluted into 10-12 mL of Mueller Hinton broth (MHB) and incubated O/N at 37° C. A log-phase subculture was obtained by adding 100 µL of O/N subculture in 10 mL MHB and incubated for a further 2-3 hours. Finally, the OD600 value of the bacterial suspension was determined and the colony forming units per millilitre (cfu/mL) extrapolated. A full dilution of the bacterial cell suspension in saline was achieved by washing (3220×g for 10 min) and the OD600 in saline determined. The suspension was then diluted out accordingly in order to achieve a 2×106 cfu/mL solution (105 cfu in 50 µL/thigh).

Quantification of injected MRSA solution: In order to be able to correlate the actual cfu/mL present in the MSRA injection solution with the estimated cfu/mL based on the OD600 readings, a standard plate count from the MSRA injection solution was done. Thus, 10 µL of the injectable MRSA suspension was diluted down to 10-1000 fold, each dilution plated out onto agar plates and incubated at 37° C. for 24 hours. From the estimated at 2×106 cfu/mL solution, 18 cfu/10 µL were found in the 1:1000 dilution, giving a final concentration of 1.8×106 cfu/mL for the actual injectable MRSA solution.

Sera sample preparation: Blood samples were taken two hours (tail incision) and 22 hours (cardiac puncture or tail incision) post saline/vancomycin/MCC treatment using Lithium-Heparin Microvette® (Sardest) or using heparin coated syringes. All samples were kept at 4° C. and spun down at 10000×g for 15 minutes. Sera was collected and kept at −80° C. until used.

Thigh homogenates and CFU determination: Thighs were homogenized at 20,000 rpm for 15 seconds using a Polytron MR2500E using a 200 mm probe (all Kinematica). Homogenate solutions were filtered using a 100 µm pore size filter (BD) and 1 mL of filtrate solution placed on ice and serial dilutions promptly done (1:10 and 1:100) and seeded onto appropriate nutrient agar plates (Bactolaboratories) and incubated at 37° C. O/N. Colonies were counted the next day and cfu/thigh and the cfu/gram of thigh calculated based on the plate count and dilution factor.

Representative results are illustrated in FIG. 3, with results summarised in Table 6 below.

TABLE 6

Efficacy of Compounds in Murine Thigh Infection Model

| Compound | Dose (mg/kg) | Average Reduction log Δcfu MRSA/thigh after 26 h<br>x = 0-2<br>xx = 2-4<br>xxx = 4-6<br>xxxx = >6 |
|---|---|---|
| Vancomycin | 200 | xxx |
| Vancomycin | 25 | x |
| Daptomycin | 50 | xxx |
| MCC_000080 | 25 | xxxx |
| MCC_000080 | 10 | xxx |
| MCC_000174 | 25 | xxx |
| MCC_000174 | 10 | xxx |
| MCC_000174 | 5 | xxx |
| MCC_000214 | 50 | xxx |
| MCC_000310 | 25 | x |

TABLE 6-continued

Efficacy of Compounds in Murine Thigh Infection Model

| Compound | Dose (mg/kg) | Average Reduction log Δcfu MRSA/thigh after 26 h<br>x = 0-2<br>xx = 2-4<br>xxx = 4-6<br>xxxx = >6 |
|---|---|---|
| MCC_000344 | 25 | xxx |
| MCC_000347 | 10 | xxxx |
| MCC_000455 | 25 | xxx |
| MCC_000742 | 25 | xx |
| MCC_004833 | 10 | xx |
| MCC_004965 | 10 | xx |
| MCC_004966 | 10 | xxxx |
| MCC_005084 | 10 | xxx |
| MCC_005125 | 10 | xxx |
| MCC_005145 | 25 | xxxx |
| MCC_005145 | 10 | xxxx |
| MCC_005161 | 10 | xxx |
| MCC_005162 | 10 | xxx |
| MCC_005165 | 10 | xxx |
| MCC_005166 | 10 | xxx |
| MCC_005181 | 10 | xx |
| MCC_005200 | 10 | xx |
| MCC_005201 | 10 | xx |
| MCC_005202 | 10 | xx |
| MCC_005203 | 10 | xxx |
| MCC_005223 | 10 | x |
| MCC_005226 | 10 | x |
| MCC_005362 | 50 | xxx |
| MCC_005362 | 10 | x |
| MCC005363 | 50 | xxx |
| MCC005364 | 10 | xx |
| MCC005365 | 50 | xx |
| MCC005481 | 10 | xxx |
| MCC005483 | 10 | xxx |
| MCC005489 | 10 | xxx |
| MCC005530 | 10 | xxx |
| MCC007221 | 10 | x |
| MCC007336 | 10 | xxxx |
| MCC007338 | 10 | xx |
| MCC007407 | 10 | xxx |
| MCC007412 | 10 | x |
| MCC007413 | 10 | x |

Efficacy of Compounds in Murine Lung Infection Survival Model (*S. pneumoniae*)

Groups of 10 male specific-pathogen-free ICR mice weighing 22±2 g were used. Acute pneumonia was induced by intratracheal inoculation with a LD90-100 dose (2.96× $10^6$ CFU/mouse) of *Streptococcus pneumoniae* (ATCC 6301) suspended in 20 μL of BHI. Vehicle (10 mL/kg), vancomycin and test substances at 25 mg/kg were each administered subcutaneously 2 hr post-infection. Mortality was recorded daily for 10 days following inoculation. Increase of 50 percent or more (≥50%) in survival rate relative to the vehicle control group indicates significant anti-infective activity. Results are illustrated in FIG. 4.

The invention claimed is:

1. An antibacterial compound of formula (III):

$$X—W-L-V \tag{III}$$

wherein:
X is a lipophilic group attached to the N-terminus of W, is based on carbon atoms and has the following parameters;
  having from 3 to 60 carbon atoms including those of any alicyclic or aromatic rings, if present;
  being straight or branched, and in the case of the latter containing one to three branch points;
  being saturated or unsaturated, in the case of the latter containing one to eight double or triple bonds;
  optionally having up to six heteroatoms, in addition to those, if present, in aromatic rings, if present, independently selected from S, O or N, not contained in an acidic substituent;
  optionally containing one or more aromatic rings, which may be fused and each of which may contain 1, 2 or 3 heteroatoms which, if present, are independently selected from N, O or S; and
  optionally having from one to six substituents selected from hydroxy, amino, methyl, methylamino and halo;

W is a basic amino acid or a basic peptide consisting of from 2 to 10 amino acids, provided that W is not or does not contain any amino acids with a sulphur-containing side chain;

L is a linking group of the formula —NH—($CR^1R^2$)$_m$—Z—($CR^3R^4$)$_n$—NH— wherein:

Z is oxygen or an optionally substituted moiety selected from the group consisting of —NH—, —CONH—, —NHCO—, —(OCH$_2$CH$_2$)$_p$—, $C_1$-$C_{12}$alkyl, $C_2$-$C_{12}$alkenyl, $C_2$-$C_{12}$alkynyl, $C_1$-$C_{12}$heteroalkyl, $C_1$-$C_{10}$heteroalkenyl, $C_3$-$C_{12}$cycloalkyl, $C_1$-$C_{12}$heterocycle, $C_6$-$C_{18}$aryl, and $C_1$-$C_{18}$heteroaryl; and $R^1$, $R^2$, $R^3$, and $R^4$ are each independently selected from the group consisting of H, halogen, optionally substituted $C_1$-$C_{12}$alkyl, optionally substituted $C_2$-$C_{12}$alkenyl, optionally substituted $C_2$-$C_{12}$alkynyl, optionally substituted $C_1$-$C_{12}$heteroalkyl, optionally substituted $C_1$-$C_{10}$heteroalkenyl, optionally substituted $C_3$-$C_{12}$cycloalkyl, optionally substituted $C_1$-$C_{12}$heterocycle, optionally substituted $C_6$-$C_{18}$aryl, optionally substituted $C_1$-$C_{18}$heteroaryl, optionally substituted carboxy, and optionally substituted carboxamide; and m is an integer selected from the group consisting of 0, 1, 2, and 3; and n is an integer selected from the group consisting of 0, 1, 2, and 3;

provided that both of m and n are not 0; and p is an integer selected from the group consisting of 1-10; or L is selected from one of the formulae:

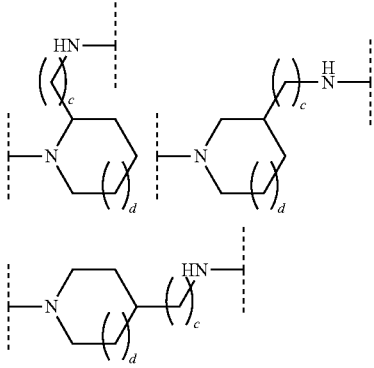

wherein c and d are integers selected from the group consisting of 0, 1, and 2; and the dotted lines show points of attachment to V and W;

and

V is a glycopeptide moiety which inhibits peptidoglycan biosynthesis in bacteria; or a pharmaceutically acceptable salt or prodrug thereof, and wherein X—W-L- is attached to V via an amide linkage to a free carboxyl group in the glycopeptide moiety.

2. The compound according to claim 1 wherein X is of formula $R^{27}$CO— wherein $R^{27}$ is a lipophilic group having from 3 to 15 carbon atoms, wherein said lipophilic group is: straight or branched and may include an alicyclic or aromatic ring, the total number of carbon atoms in the group including those of any such ring;

is saturated or unsaturated, in the case of the latter containing one to four double or triple bonds;

optionally having 1 or 2 heteroatoms, in addition to those, if present, in aromatic rings, if present, independently selected from O or N;

optionally containing one or two aromatic rings, either or both of which may contain 1 nitrogen heteroatom; and optionally having from one to three substituents selected from hydroxyl, amino, methyl, methylamino and halo.

3. The compound according to claim 1 wherein X is of formula (IV):

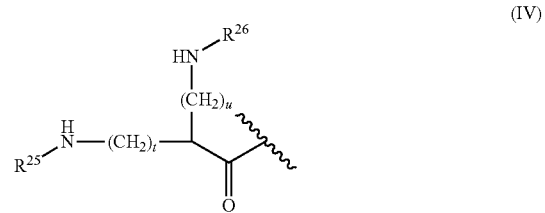

wherein each $R^{25}$ and $R^{26}$ is a lipophilic chain based on carbon atoms having the following parameters:

having from 3 to 30 carbon atoms including those of any alicyclic or aromatic rings, if present;

being straight or branched, and in the case of the latter containing one to three branch points;

being saturated or unsaturated, in the case of the latter containing one to four double or triple bonds;

optionally having 1, 2 or 3 heteroatoms, in addition to those, if present, in aromatic rings, if present, independently selected from O, S or N;

optionally containing one or more aromatic rings, which may be fused and each of which may contain 1, 2 or 3 heteroatoms which, if present, are independently selected from N, O or S; and optionally having from one to three substituents selected from hydroxy, amino, methyl, methylamino and halo;

t is an integer selected from the group consisting of 0, 1, 2, 3, 4, and 5; and u is an integer selected from the group consisting of 0, 1, 2, 3, 4, and 5;

provided that when one of t or u is 0, the other of t or u is not 0.

4. The compound according to claim 1 wherein -L- is of the formula —NH—(CH$_2$)$_m$—Z—(CH$_2$)$_n$—NH—; wherein Z, m and n are as defined in claim 1.

5. The compound according to claim 4 wherein Z is selected from the group consisting of $C_1$-$C_{12}$ alkyl, NH, O, $C_1$-$C_{12}$heterocycle, $C_6$-$C_{18}$aryl, and $C_3$-$C_{12}$cycloalkyl.

6. The compound according to claim 1 wherein -L- is of the formula —NH—(CH$_2$)$_2$—NH—, —NH—(CH$_2$)$_3$—NH—, —NH—(CH$_2$)$_4$—NH—, —NH—(CH$_2$)$_2$—NH—(CH$_2$)$_2$—NH—, —NH—(CH$_2$)$_2$—O—(CH$_2$)$_2$—NH—, —NH—(CH$_2$)$_3$—O—(CH$_2$)$_3$—NH—, —NH-(1,4-Ph)-CH$_2$—NH—, —NH-(1,3-Ph)-CH$_2$—NH—, —NH-(1,4-cHex)-CH$_2$—NH—, or —NH—CH$_2$-(1,4-cHex)-CH$_2$—NH—.

7. The compound according to claim 1 wherein -L- is of the formula —NH—CH($R^1$)—Z—($CH_2$)$_n$—NH— wherein:
$R^1$ is —(CO)OH, —(CO)OMe, —(CO)$NH_2$, —(CO)$NHNH_2$, —(CO)NHMe, —(CO)NHEt, —(CO)N(Me)$_2$, —(CO)NHBn or —(CO)$R^5$ or an optionally substituted $C_1$-$C_{12}$heterocycle or an optionally substituted $C_1$-$C_{18}$heteroaryl moiety; and
$R^5$ is an optionally substituted $C_1$-$C_{12}$heterocycle or an optionally substituted $C_1$-$C_{18}$heteroaryl moiety; and
Z and n are as defined in claim 1.

8. The compound according to claim 1 wherein -L- is of the formula —NH—CH($R^1$)—($CH_2$)$_q$—NH— wherein:
q is an integer selected from the group consisting of 0, 1, 2, 3, 4, and 5; and
$R^1$ is —(CO)OH, —(CO)OMe, —(CO)$NH_2$, —(CO)$NHNH_2$, —(CO)NHMe, —(CO)NHEt, —(CO)N(Me)$_2$, —(CO)NHBn or —(CO)$R^5$ or an optionally substituted $C_1$-$C_{12}$heterocycle or an optionally substituted $C_1$-$C_{18}$heteroaryl moiety, wherein $R^5$ is an optionally substituted $C_1$-$C_{12}$heterocycle or an optionally substituted $C_1$-$C_{18}$heteroaryl moiety.

9. The compound according to claim 1 wherein V is selected from vancomycin, vancomycin aglycon, vancomycin desvancosamine, desmethyl vancomycin, chloroeremomycin, teicoplanain-$A_2$-2, ristocetin A, eremomycin, balhimycin, actinoidin A, complestatin, chloropeptin 1, kistamycin A, avoparcin, telavancin, A40926 and oritavancin, and any one thereof optionally substituted on a primary amine with $R^{17}$, wherein $R^{17}$ is an organic side chain moiety selected from the group consisting of hydrogen, optionally substituted $C_1$-$C_{12}$alkyl, optionally substituted $C_2$-$C_{12}$alkenyl, optionally substituted $C_2$-$C_{12}$alkynyl, optionally substituted $C_1$-$C_{12}$ heteroalkyl, optionally substituted $C_1$-$C_{10}$ heteroalkenyl, optionally substituted $C_3$-$C_{12}$cycloalkyl, optionally substituted $C_2$-$C_{12}$ heterocycloalkyl, optionally substituted $C_6$-$C_{18}$aryl, and optionally substituted $C_1$-$C_{18}$heteroaryl.

10. The compound according to claim 1 wherein X—W-L-V is of formula (VI):

in which:
X, W and L are as defined in claim 1;
$R^7$ is hydrogen, a carbohydrate, or an amino carbohydrate including but not limited to 4-epi-vancosaminyl, actinosaminyl, or ristosaminyl;
$R^8$ is hydrogen, OH, or —O-mannose;
$R^9$ is —$NH_2$, —$NHCH_3$, or —N($CH_3$)$_2$;
$R^{10}$ is —$CH_2$CH($CH_3$)$_2$, [p-OH, m-Cl]phenyl, p-rhamnose-phenyl, [p-rhamnose-galactose]phenyl, [p-galactose-galactose]phenyl, [p-$CH_3$O-rhamnose]phenyl, or is linked to $R^{11}$ via [p-OH,m-(O-{m-OH,m-$R^{11}$}phenyl)]phenyl to form a cyclic ring system;
$R^{11}$ is —$CH_2$—(CO)$NH_2$, benzyl, [p-OH]phenyl, [p-OH, m-Cl]phenyl; [p-OH, m-Cl]phenyl, or is linked to $R^{10}$ via [m-OH,m-(O-{o-OH,m-$R^{10}$}phenyl)]phenyl to form a cyclic ring system;
$R^{12}$ is hydrogen, or mannose;
$R^{13}$ is hydrogen, OH, or $CH_2NHCH_2PO_3H_2$;
$R^{14}$ is hydrogen, beta-D-glucopyranose, beta-D-glucosamine, 2-O-(alpha-L-vancosaminyl)-beta-D-glucopyranose, 2-O-(alpha-L-4-epi-vancosaminyl)-beta-D-glucopyranose, (alpha- actinosaminyl)-beta-D-glucopyranose, (alpha-ristosaminyl)-beta-D-glucopyranose, or (alpha-acosaminyl)-beta-D-glucopyranose; or any one of said glucosamine or glucopyranose groups optionally substituted on a primary amine thereof with $R^{17}$, wherein $R^{17}$ is; and
$R^{15}$ and $R^{16}$ are independently hydrogen or chloro an organic side chain moiety selected from the group consisting of hydrogen, optionally substituted $C_1$-$C_{12}$alkyl, optionally substituted $C_2$-$C_{12}$alkenyl, optionally substituted $C_2$-$C_{12}$alkynyl, optionally substituted $C_1$-$C_{12}$heteroalkyl, optionally substituted $C_1$-$C_{10}$heteroalkenyl, optionally substituted $C_3$-$C_{12}$cycloalkyl, optionally substituted $C_2$-$C_{12}$heterocycloalkyl, optionally substituted $C_6$-$C_{18}$aryl, and optionally substituted $C_1$-$C_{18}$heteroaryl.

11. The compound according to claim 1 wherein W is a basic amino acid or a basic peptide comprising from 2 to 5 amino acids, provided that W is not or does not contain any amino acids with a sulphur-containing side chain.

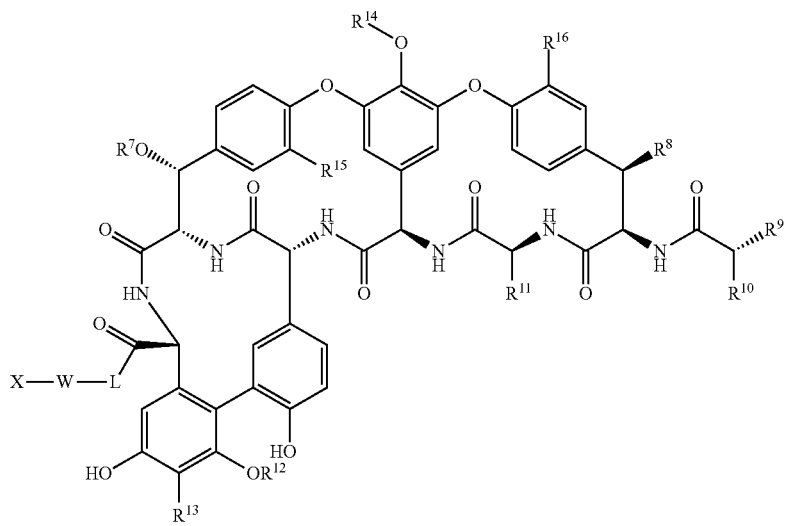

(VI)

12. The compound according to claim 11 wherein W consists of 1 residue or from 2 to 10 contiguous residues of the formula (V):

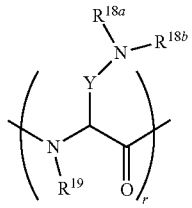

(V)

in which:
Y is a group of formula —(CR$^{20}$R$^{21}$)$_g$—;
R$^{18a}$ is selected from the group consisting of H, optionally substituted C$_1$-C$_{12}$alkyl, optionally substituted C$_2$-C$_{12}$alkenyl, optionally substituted C$_2$-C$_{12}$alkynyl, optionally substituted C$_1$-C$_{12}$heteroalkyl, optionally substituted C$_3$-C$_{12}$cycloalkyl, optionally substituted C$_2$-C$_{12}$heterocycloalkyl, optionally substituted C$_6$-C$_{18}$aryl, optionally substituted C$_1$-C$_{18}$heteroaryl, —C(=NR$^{22}$)—NR$^{23}$R$^{24}$, and OR$^{22}$,
R$^{18b}$ is selected from the group consisting of H, optionally substituted C$_1$-C$_{12}$alkyl, optionally substituted C$_2$-C$_{12}$alkenyl, optionally substituted C$_2$-C$_{12}$alkynyl, optionally substituted C$_1$-C$_{12}$heteroalkyl, optionally substituted C$_3$-C$_{12}$cycloalkyl, optionally substituted C$_2$-C$_{12}$heterocycloalkyl, optionally substituted C$_6$-C$_{18}$aryl, and optionally substituted C$_1$-C$_{18}$heteroaryl, or
R$^{18a}$ and R$^{18b}$ when taken together with the nitrogen atom to which they are attached form an optionally substituted heterocyclic moiety, or
one of R$^{18a}$ and R$^{18b}$ when taken together with any R$^{20}$ or R$^{21}$ and the atoms to which they are attached forms an optionally substituted heterocyclic moiety;
R$^{19}$ is selected from the group consisting of H and optionally substituted C$_1$-C$_{12}$alkyl;
R$^{20}$ and R$^{21}$ are each independently selected from the group consisting of H, halogen, OH, C$_1$-C$_{12}$alkyl, C$_6$-C$_{18}$aryl, C$_1$-C$_{12}$haloalkyl, C$_1$-C$_{12}$hydroxyalkyl, C$_1$-C$_{12}$alkyloxy and C$_1$-C$_{12}$haloalkyloxy, or
when taken together with the carbon to which they are attached R$^{20}$ and R$^{21}$ form an optionally substituted C$_3$-C$_{12}$cycloalkyl, or an optionally substituted C$_1$-C$_{12}$heterocycloalkyl group, or
one of R$^{20}$ and R$^{21}$ when taken together with one of R$^{18a}$ and R$^{18b}$ and the atoms to which they are attached form an optionally substituted heterocyclic moiety;
each R$^{22}$, R$^{23}$, and R$^{24}$ is independently selected from the group consisting of H, optionally substituted C$_1$-C$_{12}$alkyl, optionally substituted C$_1$-C$_{12}$heteroalkyl, optionally substituted C$_3$-C$_{12}$cycloalkyl, optionally substituted C$_6$-C$_{18}$aryl, and optionally substituted C$_1$-C$_{18}$heteroaryl, or
any two of R$^{22}$, R$^{23}$ and R$^{24}$ when taken together with the atoms to which they are attached form an optionally substituted cyclic group;
g is an integer selected from the group consisting of 1, 2, 3, 4, and 5;
r is an integer selected from the group consisting of 1, 2, 3, 4, 5, 6, 7, 8, 9 and 10.

13. The compound according to claim 12 wherein Y is (CH$_2$)$_g$.

14. The compound according to claim 11 wherein W consists of 1 residue or from 2 to 5 contiguous residues of the formula (V):

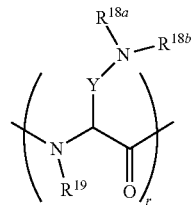

(V)

in which:
Y is a group of formula —(CR$^{20}$R$^{21}$)$_g$—;
R$^{18a}$ is selected from the group consisting of H, optionally substituted C$_1$-C$_{12}$alkyl, optionally substituted C$_2$-C$_{12}$alkenyl, optionally substituted C$_2$-C$_{12}$alkynyl, optionally substituted C$_1$-C$_{12}$heteroalkyl, optionally substituted C$_3$-C$_{12}$cycloalkyl, optionally substituted C$_2$-C$_{12}$heterocycloalkyl, optionally substituted C$_6$-C$_{18}$aryl, optionally substituted C$_1$-C$_{18}$heteroaryl, —C(=NR$^{22}$)—NR$^{23}$R$^{24}$, and OR$^{22}$,
R$^{18b}$ is selected from the group consisting of H, optionally substituted C$_1$-C$_{12}$alkyl, optionally substituted C$_2$-C$_{12}$alkenyl, optionally substituted C$_2$-C$_{12}$alkynyl, optionally substituted C$_1$-C$_{12}$heteroalkyl, optionally substituted C$_3$-C$_{12}$cycloalkyl, optionally substituted C$_2$-C$_{12}$heterocycloalkyl, optionally substituted C$_6$-C$_{18}$aryl, and optionally substituted C$_1$-C$_{18}$heteroaryl, or
R$^{18a}$ and R$^{18b}$ when taken together with the nitrogen atom to which they are attached form an optionally substituted heterocyclic moiety, or
one of R$^{18a}$ and R$^{18b}$ when taken together with any R$^{20}$ or R$^{21}$ and the atoms to which they are attached forms an optionally substituted heterocyclic moiety;
R$^{19}$ is selected from the group consisting of H and optionally substituted C$_1$-C$_{12}$alkyl;
R$^{20}$ and R$^{21}$ are each independently selected from the group consisting of H, halogen, OH, C$_1$-C$_{12}$alkyl, C$_6$-C$_{18}$ aryl, C$_1$-C$_{12}$haloalkyl, C$_1$-C$_{12}$hydroxyalkyl, C$_1$-C$_{12}$alkyloxy and C$_1$-C$_{12}$haloalkyloxy, or
when taken together with the carbon to which they are attached R$^{20}$ and R$^{21}$ form an optionally substituted C$_3$-C$_{12}$cycloalkyl, or an optionally substituted C$_1$-C$_{12}$heterocycloalkyl group, or
one of R$^{20}$ and R$^{21}$ when taken together with one of R$^{18a}$ and R$^{18b}$ and the atoms to which they are attached form an optionally substituted heterocyclic moiety;
each R$^{22}$, R$^{23}$, and R$^{24}$ is independently selected from the group consisting of H, optionally substituted C$_1$-C$_{12}$alkyl, optionally substituted C$_1$-C$_{12}$heteroalkyl, optionally substituted C$_3$-C$_{12}$cycloalkyl, optionally substituted C$_6$-C$_{18}$ aryl, and optionally substituted C$_1$-C$_{18}$heteroaryl, or any two of $R^{22}$, $R^{23}$ and $R^{24}$ when taken together with the atoms to which they are attached form an optionally substituted cyclic group;

g is an integer selected from the group consisting of 1, 2, 3, 4, and 5;

r is an integer selected from the group consisting of 1, 2, 3, 4, 5, 6, 7, 8, 9 and 10.

15. The compound according to claim 14 wherein Y is $(CH_2)_g$.

16. The compound according to claim 12 wherein the basic amino acid or basic peptide are selected from optionally substituted D- or L- lysine, ornithine, 2,4-diaminobutyric acid, 2,3-diaminopropionic acid and arginine.

17. The compound according to claim 1 wherein W is selected from the group consisting of -Lys-, -Lys-Lys-, -Lys-Lys-Lys-, -Orn-, -Orn-Orn-, -Orn-Orn-Orn-, -Lys-Orn-, -Orn-Lys, -Dab-, -Dab-Dab-, -Lys-Dab-, -Dab-Lys-, -Dab-Orn-, -Orn-Dab-, -Dap-, -Dap-Dap-, -Dap-Lys-, -Lys-Dap, -Dap-Orn, -Orn-Dap, -Dap-Dab-, and -Dab-Dap-in which any of the amino acids may be of the -L- or -D- configuration.

18. The compound according to claim 1 wherein each optional substituent in $R^1$, $R^2$, $R^3$, and $R^4$ is independently selected from the group consisting of: of halogen, =O, =S, —CN, —NO$_2$, —CF$_3$, —OCF$_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, cycloalkylalkyl, heterocycloalkylalkyl, heteroarylalkyl, arylalkyl, cycloalkylalkenyl, heterocycloalkylalkenyl, arylalkenyl, heteroarylalkenyl, cycloalkylheteroalkyl, heterocycloalkylheteroalkyl, arylheteroalkyl, heteroarylheteroalkyl, hydroxy, hydroxyalkyl, alkyloxy, alkyloxyalkyl, alkyloxycycloalkyl, alkyloxyheterocycloalkyl, alkyloxyaryl, alkyloxyheteroaryl, alkyloxycarbonyl, alkylaminocarbonyl, alkenyloxy, alkynyloxy, cycloalkyloxy, cycloalkenyloxy, heterocycloalkyloxy, heterocycloalkenyloxy, aryloxy, phenoxy, benzyloxy, heteroaryloxy, arylalkyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, alkylsulfinyl, arylsulfinyl, aminosulfinylaminoalkyl, —C(=O)OH, —C(=O)Ra, C(=O)OR$_a$, C(=O)NR$_a$R$_b$, C(=NOH)R$_a$, C(=NR$_a$)NR$_b$R$_c$, NR$_a$R$_b$, NR$_a$C(=O)R$_b$, NR$_a$C(=O)OR$_b$, NR$_a$C(=O)NR$_b$R$_c$, NR$_a$C(=NR$_b$)NR$_c$R$_d$, NR$_a$SO$_2$R$_b$, —SRa, SO$_2$NRaRb, —OR$_a$, OC(=O)NR$_a$R$_b$, OC(=O)R$_a$ and acyl, wherein R$_a$, R$_b$, R$_c$ and R$_d$ are each independently selected from the group consisting of H, $C_1$-$C_{12}$ alkyl, $C_1$-$C_{12}$ haloalkyl, $C_2$-$C_{12}$ alkenyl, $C_2$-$C_{12}$ alkynyl, $C_1$-$C_{10}$ heteroalkyl, $C_3$-$C_{12}$ cycloalkyl, $C_3$-$C_{12}$ cycloalkenyl, $C_1$-$C_{12}$ heterocycloalkyl, $C_1$-$C_{12}$ heterocycloalkenyl, $C_6$-$C_{18}$aryl, $C_1$-$C_{18}$heteroaryl, and acyl, or any two or more of R$_a$, R$_b$, R$_c$ and R$_d$, when taken together with the atoms to which they are attached form a heterocyclic ring system with 3 to 12 ring atoms.

19. The compound according to claim 1 selected from compounds disclosed in Table 2.

20. A pharmaceutically acceptable salt of any compound described in claim 1.

21. A composition comprising a compound according to claim 1 and a pharmaceutically acceptable carrier, diluent or excipient.

22. A method of treating a bacterial infection in a subject which method comprises administering to a subject an effective amount of the antibacterial agent of claim 1.

23. A method of treating a bacterial infection in a subject which method comprises administering to a subject an effective amount of the composition of claim 21.

* * * * *

SEQUENCE LISTING

```
<160> NUMBER OF SEQ ID NOS: 1

<210> SEQ ID NO 1
<211> LENGTH: 5
<212> TYPE: PRT
<213> ORGANISM: Artificial Sequence
<220> FEATURE:
<223> OTHER INFORMATION: Synthetic Construct

<400> SEQUENCE: 1

Gly Ser Lys Lys Lys
1               5
```